(12) United States Patent
Yonetani et al.

(10) Patent No.: US 6,608,061 B2
(45) Date of Patent: *Aug. 19, 2003

(54) BISARYL COMPOUND AND MEDICAMENT FOR CANCER TREATMENT COMPRISING THE SAME

(75) Inventors: Yoshiyuki Yonetani, Machida (JP); Takeshi Takahashi, Numazu (JP); Yuko Kanda, Machida (JP); Tamio Mizukami, Machida (JP); Tatsuya Tamaoki, Machida (JP); Shun-ichi Ikeda, Sakai (JP); Masanobu Takashima, Minami-ashigara (JP); Naoki Asanuma, Minami-ashigara (JP); Tadashi Inaba, Minami-ashigara (JP); Hiroshi Takeuchi, Minami-ashigara (JP); Hiroshi Kawamoto, Minami-ashigara (JP); Yoshihisa Tsukada, Minami-ashigara (JP); Masato Satomura, Minami-ashigara (JP); Hiroshi Kitaguchi, Minami-ashigara (JP)

(73) Assignees: Kyoma Hakko Kogyo Co., Ltd., Tokyo (JP); Fuji Photo Film Co., Ltd., Kanagawa (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/424,352

(22) PCT Filed: May 21, 1998

(86) PCT No.: PCT/JP98/02242

§ 371 (c)(1),
(2), (4) Date: Feb. 14, 2000

(87) PCT Pub. No.: WO98/52551

PCT Pub. Date: Nov. 26, 1998

(65) Prior Publication Data

US 2003/0018070 A1 Jan. 23, 2003

(30) Foreign Application Priority Data

May 22, 1997 (JP) .............................................. 9/132398
Dec. 17, 1997 (JP) .............................................. 9/347989

(51) Int. Cl.$^7$ ...................... A61K 31/10; A61K 31/135; A61K 31/165; A61K 31/445; A61K 31/495; A61K 31/53; A61K 31/535; A61K 31/47; A61P 35/00

(52) U.S. Cl. ...................... 514/241; 514/710; 514/711; 514/712; 514/713; 514/513; 514/532; 514/544; 514/570; 514/679; 514/709; 514/602; 514/472; 514/618; 514/438; 514/616; 514/269; 514/277514/274; 514/252.1; 514/351; 514/311; ; 514/354; 514/355; 514/237.8; 514/238.2; 514/460; 514/451; 514/452; 514/467; 514/400; 514/465; 514/255.01; 560/125; 568/39; 568/47; 568/29; 562/26; 562/512; 546/232; 546/226; 546/316; 546/165; 546/176; 544/159; 544/387; 544/408; 544/216; 549/78; 549/480; 549/453; 549/439; 549/417; 549/373; 549/340.1

(58) Field of Search ............................ 514/710–3, 513, 514/602, 532, 472, 544, 618, 570, 438, 679, 709, 616, 241, 269, 277, 274, 252.1, 351, 311, 354, 355, 237.8, 238.2, 460, 451, 452, 467, 400, 465, 255.01; 568/39, 47, 29; 562/26, 512; 560/125

(56) References Cited

U.S. PATENT DOCUMENTS

| | | | |
|---|---|---|---|
| 4,282,242 A | | 8/1981 | Holland |
| 4,448,730 A | * | 5/1984 | Van't Riet ............ 260/500.5 H |
| 4,612,393 A | | 9/1986 | Ravichandran |
| 5,183,828 A | * | 2/1993 | Van't Riet ................... 514/508 |
| 5,932,553 A | * | 8/1999 | McMorris .................... 514/23 |

FOREIGN PATENT DOCUMENTS

| | | |
|---|---|---|
| CA | 1157774 | 11/1983 |
| DE | 3541234 | 5/1986 |

(List continued on next page.)

OTHER PUBLICATIONS

Zarkovic M et al. Carcinogenesis. 16(10), 2599–2601, 1995.*

Cai, Jun Chao, et al., "Synthesis and antitumor properties of N1–(acyloxy)methyl derivatives of bis(2,6–dioxopiperazines)," Chem. Pharm. Bull., 1989, vol. 37, No. 11, pp. 2976 to 2983, especially, No. VI–16, VI–17 in TABLE I. of p. 2977 (Copy submitted to USPTO by WIPO).

(List continued on next page.)

Primary Examiner—Evelyn Mei Huang
(74) Attorney, Agent, or Firm—Sughrue Mion, PLLC

(57) ABSTRACT

A medicament for treatment of cancer comprising a compound represented by the following general formula (I) or a physiologically acceptable salt thereof:

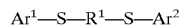

Ar$^1$—S—R$^1$—S—Ar$^2$ wherein R$^1$ represents a nonmetal bridging group; Ar$^1$ and Ar$^2$ independently represent a group selected from the group consisting of an aryl group which has, on its ring, one to three hydroxyl groups optionally substituted with a monovalent group and said aryl group may have one to three substituents other than hydroxyl group on its ring; and a heteroaryl group which has, on its ring, one to three hydroxyl groups optionally substituted with a monovalent group, and said heteroaryl group may have one to three substituents other than hydroxyl group on its ring.

4 Claims, No Drawings

FOREIGN PATENT DOCUMENTS

| | | |
|---|---|---|
| EP | 119160 | 9/1984 |
| EP | 140297 | 5/1985 |
| FR | 1507899 | 12/1967 |
| JP | 3-182393 | 8/1991 |
| WO | 96/04275 | 2/1996 |
| WO | 98/03458 | 1/1998 |

OTHER PUBLICATIONS

Motohashi, Noboru, "Antitumor activities of phenothiazines and phenoxazines". Yakugaku Zasshi, 1983, vol. 103, No. 3, pp. 364 to 371, especially, Compd. No. 41 to 44 in TABLE IV. of p. 369 (Copy submitted to USPTO by WIPO).

Kricheldorf, Hans R., et al., "New polymer syntheses. 55. Aromatic poly(ether sulfides) of pyridine and pyridazine". Polym. Bull., 1992, vol. 28, No. 4, pp. 411 to 418 & Database CAPLUS on STN, American Chemical Society (ACS), Columbus, OH, USA), AN.117=112193, especially, compounds to Registry No. 143232–42–2, 143232–44–4, 143277–03–6, 143277–05–8, 143277–06–9, 143277–16–1, 143277–17–2, 143277–21–8, 143277–22–9, 143277–23–0, 143231–98–5, 143231–99–6 (Copy submitted to USPTO by WIPO).

International Search Report.

* cited by examiner

BISARYL COMPOUND AND MEDICAMENT FOR CANCER TREATMENT COMPRISING THE SAME

This application is a 371 of PCT/JP98/02242, filed May 21, 1998.

TECHNICAL FIELD

The present invention relates to a novel bisaryl compound and a medicament for treatment of cancer which comprises said compound or a known bisaryl compound as an active ingredient.

BACKGROUND ART

In the cell proliferation process, DNA replication process is regulated by a family of enzymes relating to nucleic acid synthesis. Among these enzymes, it has been reported that ribonucleotide reductase (occasionally referred to as "RNR" hereinafter in this specification) is a particularly important enzyme involved in the biosynthesis of dNTPs, which are precursors of DNA (Ann. Rev. Biochem, 57, pp.349–374).

In cancer cells, endless cell proliferation continues due to over-expression of certain families of enzymes and the like, which leads to death of the host. It has been reported that RNR is over-expressed in cancer cells to maintain high ability of cell proliferation of cancer cells (Cancer Research, 43, pp.3466–3492). Moreover, there has also been reported a possibility that malignant alteration of cancer is caused with accompanying expression of RNR (Proc. Natl. Acad. Sci. USA, 93, pp.14036–14040). Therefore, an agent selectively inhibiting RNR is expected to be able to exert highly selective toxicity to cancer cells, and accordingly, expected to be useful as a medicament for cancer treatment that selectively inhibits the proliferation of cancer cells.

Hydroxyurea has been known as a compound exhibiting antitumor activity by inhibiting RNR, and the compound is used clinically as an anti-leukemia agent. However, the drug only has weak inhibitory activity, and therefore a high blood concentration need to be maintained for a long period of time to successfully inhibit RNR. In addition, the drug causes strong side effects such as bone marrow toxicity, and hence is not a satisfactory therapeutic agent. For these reasons, it has been desired to develop an RNR inhibitor which has potent RNR inhibitory activity as well as reduced side effects including bone marrow toxicity, and has a wide range of effective dosage.

As low molecular RNR inhibitors, there have so far been reported polyhydroxybenzoic acid derivatives (Published Japanese translation of PCT international publication (Kohyo) No. 60-501409/1985), alkoxyphenol compounds (Mol. Pharmacol., 45, pp.792–796), thiosemicarbazone derivatives (Biochem. Pharmacol., 48, pp.335–344), bipyridyl derivatives (Cancer Research, 53, pp.19–26) and the like. However, RNR inhibitory activity and anticancer activity of bisaryl derivatives have not been reported. As for usefulness of bisaryl compounds composed of aryl groups linked by means of plural sulfur atoms as anticancer agents, derivatives comprising aromatic benzenesulfonamide groups as the bisaryl moieties (Japanese Patent Publication (Kokoku) No. 42-10857/1967) have been reported, and the synthesis of an anthramycin dimer has also been reported (Tetrahedron Lett., 129, p.5105). It has also been known that certain bisaryl compounds have antiviral activity (Japanese Patent Unexamined Publication (Kokai) No. 5-501860/1993).

DISCLOSURE OF THE INVENTION

An object of the present invention is to provide a novel bisphenol compound useful as an active ingredient of a medicament.

Another object of the present invention is to provide an medicament for treatment of cancer which comprises a bisphenol compound having inhibitory activity against RNR as an active ingredient.

A still further object of the present invention is to provide a novel bisaryl compound useful as an active ingredient of a medicament.

The inventors of the present invention found that the compounds of the present invention represented by the following formula have inhibitory activity against RNR and anticancer activity, and thus they are useful as an active ingredient of a medicament for treatment of cancer. The present invention was achieved on the basis of these findings.

The present invention provides a medicament for treatment of cancer which comprises a compound represented by the following general formula (I):

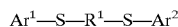

$Ar^1$—S—$R^1$—S—$Ar^2$ or a physiologically acceptable salt thereof,
wherein $R^1$ represents a nonmetal bridging group, $Ar^1$ and $Ar^2$ independently represent a group selected from the group consisting of an aryl group which has, on its ring, one or more hydroxyl groups optionally substituted with a monovalent group (the aryl group may have one to three substituents other than a hydroxyl group on its ring), and a heteroaryl group which has, on its ring, one or more hydroxyl groups optionally substituted with a monovalent group (the heteroaryl group may have one to three substituents other than a hydroxyl group on its ring).

Preferred embodiments of the aforementioned invention provided are as follows:
the above medicament for treatment of cancer which comprises a compound represented by the aforementioned general formula (I) or a physiologically acceptable salt thereof, wherein $R^1$ is represented by the general formula (II):

—$R^2$—N($R^4$)—$R^3$—         (II)

wherein $R^2$ and $R^3$ independently represent a divalent group, $R^4$ represents a monovalent group, and $R^4$ may bind to $R^2$ or $R^3$ to form a cyclic structure; the above medicament for treatment of cancer which comprises the aforementioned compound or a physiologically acceptable salt thereof, wherein $R^1$ is represented by the general formula (III):

—$R^5$—$X^1$—$R^6$—         (III)

wherein $R^5$ and $R^6$ independently represent a single bond or a divalent group not containing a nitrogen atom, $X^1$ represents an oxygen atom, $S(O)_k$ wherein k represents an integer of from 0 to 2, or $[(R^9X^2)_m(R^{10}X^3)_n(R^{11}X^4)_p]_q$ wherein $R^9$, $R^{10}$, and $R^{11}$ independently represent a single bond or a divalent group not containing a nitrogen atom, and wherein any groups selected from $R^5$, $R^6$, $R^9$, $R^{10}$ and $R^{11}$ may bind together to form a cyclic structure, $X^2$, $X^3$ and $X^4$ independently represent an oxygen atom, $S(O)_r$ wherein r represents an integer of from 0 to 2, or a single bond, and m, n, p and q independently represent an integer of from 1 to 3;
the above medicament for treatment of cancer which comprises the aforementioned compound or a physiologically acceptable salt thereof, wherein $R^1$ is 2,6-pyridinediyldimethyl group (the pyridinediyldimethyl group may have one to three substituents other than a hydrogen atom on its ring);
the above medicament for treatment of cancer which comprises the aforementioned compound or a physiologically acceptable salt thereof, wherein $R^2$ and $R^3$ are the same divalent groups, and $R^4$ is a $C_{1-4}$ alkyl group which may have one to three substituents other than a hydrogen atom; the above medicament for treatment of cancer which comprises the aforementioned compound or a physiologically acceptable salt thereof, wherein $R^2$ and $R^3$ are the same divalent groups, $R^4$ is represented as $COR^{25}$ wherein $R^{25}$ represents a hydrogen atom, a $C_{1-4}$ alkyl group, an aryl group, a heteroaryl group, a heterocyclic group, an aralkyl group, or $NR^{26}R^{27}$ wherein $R^{26}$ and $R^{27}$ each represent a hydrogen atom, a $C_{1-4}$ alkyl group, an aryl group, a heteroaryl group, a heterocyclic group, or an aralkyl group, and said alkyl group, aryl group, heteroaryl group, heterocyclic group, and aralkyl group including those for $R^{26}$ and $R^{27}$ may have one to three substituents other than a hydrogen atom; and the above medicament for treatment of cancer which comprises the aforementioned compound or a physiologically acceptable salt thereof, wherein $R^1$ is represented as $R^{1A}-R^{1B}CO-R^{1C}-R^{1D}-R^{1C}-COR^{1B}-R^{1A}$ wherein $R^{1A}$ represents a $C_{1-4}$ lower alkylene group, $R^{1B}$ represents NH or a methylene group, $R^{1C}$ represents a single bond or a methylene group, $R^{1D}$ represent a divalent bridging cyclic hydrocarbon group, a monocyclic hydrocarbon group, or a heterocyclic group, and said bridging cyclic hydrocarbon group, monocyclic hydrocarbon group, and heterocyclic group may have one to three substituents other than a hydrogen atom.

According to further preferred embodiments of the aforementioned each invention provided are the above medicament for treatment of cancer which comprises the aforementioned compound or a physiologically acceptable salt thereof, wherein $Ar^1$ and $Ar^2$ independently represent the aforementioned aryl group; the above medicament for treatment of cancer which comprises the aforementioned compound or a physiologically acceptable salt thereof, wherein both of $Ar^1$ and $Ar^2$ are 4-hydroxyphenyl groups; the above medicament for treatment of cancer which comprises the aforementioned compound or a physiologically acceptable salt thereof, wherein $R^2$ and $R^3$ are the same groups, and the minimum number of bridge-forming atoms thereof is from 1 to 10, preferably 1 to 4; the above medicament for treatment of cancer which comprises the aforementioned compound or a physiologically acceptable salt thereof, wherein $R^2$ and $R^3$ are the same divalent groups optionally having a branched chain (said divalent groups may contain 1 to 3 oxygen atoms); the above medicament for treatment of cancer which comprises the aforementioned compound or a physiologically acceptable salt thereof, wherein the total number of carbon atoms is 35 or less; and the above medicament for treatment of cancer which comprises the aforementioned compound or a physiologically acceptable salt thereof, which is used as a medicament for preventive and/or therapeutic treatment of a disease caused by overexpression of ribonucleotide reductase.

As another aspect of the present invention, provided is a ribonucleotide reductase inhibitor or a selective cancer cell proliferation inhibitor which comprises a compound represented by the aforementioned general formula (I) or (II).

As further aspects of the present invention, provided are use of the aforementioned compound or a physiologically acceptable salt thereof for the manufacture of the medicaments for treatment of cancer which comprise a compound represented by the aforementioned general formula (I) or (II), or a physiologically acceptable salt thereof as an active ingredient, preferably the medicaments for treatment of cancer in the form of a pharmaceutical composition comprising the aforementioned compound or a physiologically acceptable salt thereof together with an additive for pharmaceutical preparations; and a method for treatment of cancer which comprises the step of administering a therapeutically effective amount of a substance selected form the aforementioned compound and a physiologically acceptable salt thereof to a patient.

The present invention further provides a compound represented by the general formula (XII):

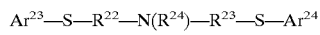

or a salt thereof, wherein, $R^{22}$ and $R^{23}$ independently represent a divalent group, $R^{24}$ represents a monovalent group or a monovalent atom, and $R^{24}$ may bind to $R^{22}$ and/or $R^{23}$ to form a cyclic structure, and may further bind to one or two $C_{1-4}$ alkylene groups to form a divalent group, and $Ar^{23}$ and $Ar^{24}$ independently represent a group selected from the group consisting of an aryl group which has, on its ring, one to three hydroxyl groups optionally substituted with a monovalent group (the aryl group may have one to three substituents other than a hydroxyl group on its ring), and a heteroaryl group which has, on its ring, one to three hydroxyl groups optionally substituted with a monovalent group (the heteroaryl group may have one to three substituents other than a hydroxyl group on its ring), provided that $R^{22}-N(R^{24})-R^{23}$ except for the part of $R^{24}$ does not contain an amide bond when $R^{22}$ and $R^{23}$ do not form a ring, and provided that when each of $Ar^{23}$ and $Ar^{24}$ is a phenyl group having one hydroxyl group on the ring, not all of said phenyl groups have a tertiary alkyl group at a position on the ring adjacent to the hydroxyl group.

As a preferred embodiment of the above invention, provided is the aforementioned compound or a salt thereof, wherein two or three groups selected from the group consisting of $R^{22}$, $R^{23}$ and $R^{24}$ form a ring or rings.

Further preferred embodiments provided are as follows: the above compound or a salt thereof wherein $R^{22}$ and $R^{23}$ are the same divalent groups, and $R^{24}$ is a $C_1$–4 alkyl group which may have one to three substituents other than a hydrogen atom;

the above compound or a salt thereof wherein $R^{22}$ and $R^{23}$ are the same divalent groups, $R^{24}$ is represented by $COR^{125}$ wherein $R^{125}$ represents a hydrogen atom, a $C_{1-4}$ alkyl group, an aryl group, a heteroaryl group, a heterocyclic group, an aralkyl group, or $NR^{126}R^{127}$ wherein $R^{126}$ and $R^{127}$ each represent a hydrogen atom, a $C_{1-4}$ alkyl group, an aryl group, a heteroaryl group, a heterocyclic group, or an aralkyl group, and said alkyl group, aryl group, heteroaryl group, heterocyclic group, and aralkyl group including those for $R^{126}$ and $R^{127}$ may have one to three substituents other than a hydrogen atom; and the above compound or a salt thereof wherein $R^{22}-N(R^{24})-R^{23}$ is represented by $R^{101A}-R^{101B}CO-R^{101C}-R^{101D}-R^{101C}-COR^{101B}-R^{101A}$ wherein $R^{101A}$ represents a $C_{1-4}$ lower alkylene group, $R^{101B}$ represents NH or methylene group, $R^{101C}$ represents a single bond or a methylene group, $R^{101D}$ represent a divalent bridging cyclic hydrocarbon group, a monocyclic hydrocarbon group, or a heterocyclic group, and said bridging cyclic hydrocarbon group, monocyclic hydrocarbon group, and heterocyclic group may have one to three substituents other than a hydrogen atom.

Further preferred embodiments provided are as follows: the above compound or a salt thereof wherein $Ar^{23}$ and $Ar^{24}$ independently represents an aryl group which has, on its ring, one to three hydroxyl groups optionally substituted with a monovalent group (the aryl group may have one to three substituents other than a hydroxyl group on its ring);

the above compound or a salt thereof wherein both of $Ar^{23}$ and $Ar^{24}$ independently represent a hydroxy-substituted phenyl group;

the above compound or a salt thereof wherein $Ar^{23}$ and $Ar^{24}$ independently represent a monohydroxy-substituted phenyl group;

the above compound or a salt thereof wherein both of $Ar^{23}$ and $Ar^{24}$ are 4-hydroxyphenyl groups;

the above compound or a salt thereof wherein the minimum number of bridge-forming atoms of $R^{22}$ and $R^{23}$ are independently from 1 to 10 [The term "minimum number of bridge-forming atoms" used herein means a minimum number of atoms that connect one atom and the other atom to be bridged. For example, the minimum number of bridge-forming atoms is 3 for 1,3-propenylene group, 2 for 1,2-propenylene group, and 5 for 1,5-(4-butoxy-3-pentenylene) group. Also for example, the number is 3 for 1,3-phenylene group, 2 for 1,2-phenylene group, 3 for 2,4-quinolinediyl group, and 4 for 1,5-naphthylene, as well as 4 for ethylenedioxy group, 3 for malonyl group, and 4 for phthaloyl group.];

the above compound or a salt thereof wherein $R^{22}$ and $R^{23}$ are the same groups and each of the minimum numbers of bridge-forming atoms thereof is 1 to 10, preferably 1 to 4;

the above compound or a salt thereof wherein $R^{22}$ and $R^{23}$ independently represent methylene group, ethylene group, propylene group or butylene group;

the above compound or a salt thereof wherein $R^{22}$ and $R^{23}$ are the same groups, and represent methylene group, ethylene group, propylene group or butylene group; and the above compound or a salt thereof wherein the total number of carbon atoms is 35 or less.

BEST MODE FOR CARRYING OUT THE INVENTION

The groups that constitute the general formulas (I) and (II) will be explained specifically.

The aryl group represented by $Ar^1$ and $Ar^2$ in the general formula (I) may be, for example, an aryl group having 6 to 12 carbon atoms, preferably phenyl group, naphthyl group or the like. The term "aryl group" has the same meaning in the following description unless otherwise indicated. The heteroaryl group may be, for example, a heteroaryl group having 5 to 12 ring-constituting atoms, such as pyridyl group, pyrrolyl group, imidazolyl group, quinolinyl group, thienyl group, and furyl group. As the heteroaryl group, for example, a group comprising a 5- or 6-membered nitrogen-containing or oxygen-containing heteroaryl ring having an enol type hydroxyl group and an active methine or active methylene group, such as pyrazolone ring and pyridone ring, may preferably used. The term "heteroaryl group" has the same meaning in the following description unless otherwise indicated. It is preferred that both of $Ar^1$ and $Ar^2$ are aryl groups, and it is more preferred that both of $Ar^1$ and $Ar^2$ are phenyl groups.

The number and the substituting position of the hydroxyl group or the hydroxyl group substituted with a monovalent group on the ring of the aryl group or the heteroaryl group are not particularly limited, and they preferably have one hydroxyl group. For example, when the aryl group is phenyl group, phenyl group substituted with one hydroxyl group at the p-position (4-position) may be exemplified. Examples of the monovalent group in the one to three hydroxyl groups substituted with a monovalent group present independently on the ring of the aryl group or the heteroaryl group include, but not limited thereto, linear or branched $C_{1-6}$ alkyl groups such as methyl group, ethyl group, n-propyl group, isopropyl group, n-butyl group, sec-butyl group and tert-butyl group; aryl groups such as phenyl group and naphthyl group; $C_{1-12}$ alkanoyl groups which may be substituted; hydroxy ($C_{2-6}$)alkyl groups such as hydroxyethyl group; $C_{7-15}$ aralkyl groups such as benzyl group and phenethyl group; $C_{6-12}$ aroyl groups; $C_{1-6}$ alkylsulfonyl groups; $C_{6-12}$ arylsulfonyl groups; $C_{1-6}$ alkoxycarbonyl groups; aryloxycarbonyl groups; hydroxyphenylthio($C_{1-6}$) alkyl groups; aminocarbonyl groups substituted with 0 to two $C_{1-6}$ alkyl groups or $C_{6-12}$ aryl groups; aminoalkylcarbonyl groups substituted with 0 to two $C_{1-6}$ alkyl groups or $C_{6-12}$ aryl groups; $C_{1-6}$ alkoxy-substituted $C_{1-6}$ alkanoyl groups, $C_{1-6}$ alkylamino-substituted $C_{1-6}$ alkanoyl groups, piperidinocarbonyl group, 4-piperidinopiperidinocarbonyl group, N-t-butoxycarbonyl-N-methylglycyl group and the like.

On the ring of the aforementioned aryl group or the heteroaryl group, one to three substituents other than a hydroxyl group or a hydroxyl group substituted with a monovalent group may be present. As such a substituent, examples which can be used are as follows: a halogen atom selected from fluorine atom, chlorine atom, bromine atom, and iodine atom; a $C_{1-6}$ alkyl group such as methyl group, ethyl group, n-propyl group, isopropyl group, n-butyl group, sec-butyl group and tert-butyl group; a halogenated $C_{1-6}$ alkyl group such as trifluoromethyl group; a $C_{1-6}$ alkoxyl group such as methoxy group, ethoxy group, n-propoxy group, isopropoxy group, n-butoxy group, sec-butoxy group and tert-butoxy group; a $C_{1-6}$ alkylenedioxy group such as methylenedioxy group and ethylenedioxy group; carboxyl group; a $C_{1-6}$ alkoxycarbonyl group; non-substituted amino group; a $C_{1-6}$ alkyl-substituted amino group such as methylamino group, dimethylamino group and ethylamino group; cyano group or the like. Among them, halogen atoms, $C_{1-6}$ alkyl groups, $C_{1-6}$ alkoxyl groups and the like are preferred.

In the specification, the term "bridging group" means a group or an atom that can form two independent covalent bonds. In the specification, the term "divalent group" means the bridging group which can form two independent covalent bonds, and contains at least one carbon atom. The divalent group may have a chain-like or a cyclic structure, or may have a combination of portions of a chain-like structure and a cyclic structure.

$R^1$ in the general formula (I) represents a divalent group consisting of a nonmetal bridging group, which preferably comprising atoms selected from the group consisting of carbon atom, hydrogen atom, oxygen atom, nitrogen atom, sulfur atom, and phosphorus atom, and has atoms excluding hydrogen the number of which is 1 to 80. $R^1$ may further contain one to three halogen atoms.

These divalent groups may contain one to three unsaturated bonds, such as a double bond consisting of a carbon-carbon bond, carbon-oxygen bond, sulfur-oxygen bond, carbon-nitrogen bond, or nitrogen-nitrogen bond, or triple bond consisting of a carbon-carbon bond. Furthermore, they may contain one to three covalent bonds including any hetero atoms such as carbamoyl bond, sulfamoyl bond, ether bond, and disulfide bond as a partial structure. For example, they may contain one to three cyclic structures selected from monocyclic structures such as those consisting of benzene ring, cyclohexane ring, tetrahydrofuran ring, and pyranone ring, condensed rings such as naphthalene ring, indole ring, and quinoline ring, and bicyclo structures such as bicyclooctane ring. Furthermore, examples also include pyrrole ring, piperidine ring, indole ring, pyridine ring, triazine ring, pyrimidine ring, quinoline ring, oxazine ring, indazole ring, thiazole ring and the like. When the divalent group is a cyclic group or chain-like group, or when it contains a partial chain-like structure, it may contain a branched chain.

The aforementioned ring that constitutes the divalent group, and carbon atoms and/or hetero atoms constituting the backbone of the divalent group may have one or more substituents thereon, for example, those selected from the group consisting of a halogen atom such as fluorine atom, chlorine atom, and bromine atom; a linear or branched $C_{1-6}$ alkyl group such as methyl group, ethyl group, n-propyl group, isopropyl group, n-butyl group, sec-butyl group, and tert-butyl group; a linear or branched $C_{1-6}$ alkoxyl group such as methoxy group, ethoxy group, n-propoxy group, isopropoxy group, n-butoxy group, sec-butoxy group and tert-butoxy group (those alkyl and alkoxyl groups may have a substituent such as hydroxyl group, a $C_{1-6}$ alkoxyl group, a $C_{1-6}$ alkyl-substituted or non-substituted carbamoyl group, non-substituted amino group, a $C_{1-6}$ alkyl-substituted amino group such as methylamino group, dimethylamino group, and ethylamino group, a $C_{1-6}$ cyclic amino group such as morpholino group and piperidino group, and a $C_{1-6}$ cyclic aminocarbonyl group such as morpholino group and piperidino group); a $C_{1-6}$ alkylenedioxy group such as methylenedioxy group and ethylenedioxy group; carboxyl group; a $C_{1-6}$ alkoxycarbonyl group; non-substituted amino group or a $C_{1-6}$ alkyl-substituted amino group such as methylamino group, dimethylamino group and ethylamino group; hydroxyl group; an aryl group such as phenyl group; a $C_{1-6}$ alkyl-substituted sulfonyl group; a $C_{1-6}$ alkanoyl group such as acetyl group and propionyl group; a halogenated $C_{1-6}$ alkanoyl group such as trifluoroacetyl group and monochloroacetyl group; an alkoxy-substituted $C_{1-6}$ alkanoyl group such as methoxymethylcarbonyl group; cyano group; a $C_{1-6}$ alkyl-substituted or non-substituted carbamoyl group; sulfamoyl group; carboxyl group; sulfo group; a lactone ring or a lactam ring consisting of 4 to 8 ring-constituting atoms; and a halogen atom.

Preferred examples of the divalent group represented by $R^1$ include, for example, linear or branched $C_{1-6}$ alkylene groups such as methylene group, ethylene group, propylene group, butylene group, and pentylene group; arylene groups such as p-phenylene group, m-phenylene group, 1,4-naphthylene group, and 1,5-naphthylene group; heteroarylene groups such as 2,6-pyridinediyl group; vinylene group; ethynylene group; propenylene group; propynylene group; $C_{2-6}$ alkenylene groups such as 1-butenylene group, and cis- and trans-2-butenylene group, $C_{2-6}$ alkynylene groups and the like. These divalent groups may have one to three substituents selected from the aforementioned substituents. Preferred examples of the alkylene group having one or more substituents include, for example, oxo($C_{1-6}$) alkylene groups such as 1-oxoethylene group, 1-oxo-2-methylethylene group, and 1-oxopropylene group; and oxy ($C_{1-6}$)alkylene groups such as 1-oxypropylene group, and 2-oxypropylene group and the like. Divalent groups consisting of a suitable combination of groups selected from alkylene groups, arylene groups and heteroarylene groups are also preferred.

Those wherein $R^1$ represents $R^{1A}$—$R^{1B}$CO—$R^{1C}$—$R^{1D}$—$R^{1C}$—COR$^{1B}$R$^{1A}$, wherein $R^{1A}$ represents a $C_{1-4}$ lower alkylene group, $R^{1B}$ represents NH or a methylene group, $R^{1C}$ represents a single bond or a methylene group, $R^{1D}$ represents a divalent bridging cyclic hydrocarbon group, a monocyclic hydrocarbon group, or a heterocyclic group, and said bridging cyclic hydrocarbon group, monocyclic hydrocarbon group, and heterocyclic group may have one to three substituents other than a hydrogen atom, are also preferred examples of the divalent group. Examples of the divalent bridging cyclic hydrocarbon group and monocyclic hydrocarbon group include, for example, 1,1-cyclopentylene, 5,6-norbornenylene, 1,1-cyclopropylene, 1,1-cyclobutylene, 1,2-cyclobutylene, 1,2-cyclopentylene, 2,2-dimethyl-1,3-cyclopentylene, 1,1-cyclohexylene, 1,2-cyclohexylene, 1,3-cyclohexylene, 1,4-cyclohexylene, 1,3-adamantylene, 1,1-phenylene, 1,2-phenylene, 1,3-phenylene, 1,4-phenylene, 1,4-naphthylene, 2,3-naphthylene, 2,6-naphthylene, 1,8-naphthylene and the like. Examples of the divalent heterocyclic group include, for example, 1,4-piperazinylene, 4-oxo-2,6-pyranylene, 2,3-pyrrolylene, 3,5-pyrazolylene, 2,3-indolylene, 2,6-pyridylene, 2,3-pyridylene, 2,4-pyridylene, 3,4-pyridylene, 2,5-pyridylene, 3,5-pyridylene, 2,3-pyrazinylene, 3,4-furylene, 4,5-imidazolylene, 1,2,3-triazol-4, 5-ylene, 7-oxabicyclo[2.2.1]heptynyl-2,3-ylene, tricyclo[4.2.1.0$^{2,5}$] nona-3,7-dien-3,4-ylene, 2,2-dimethyldioxolan-4,5-ylene and the like. As preferred substituents on the divalent bridging cyclic hydrocarbon group, monocyclic hydrocarbon group, and heterocyclic group, those exemplified for the substituents on the rings of the aforementioned aryl group and heteroaryl group may be used.

The minimum number of bridging group-forming atoms of $R^1$ is preferably in the range of 1 to 20, more preferably 1 to 9, and most preferably 3 to 7. The total atom number of the whole compound of the general formula (I) is preferably 50 or less.

The groups that constitute the compounds represented by the general formula (II) will be specifically explained below.

The definition of the divalent group represented by $R^2$ and $R^3$ is the same as that of the divalent group represented by $R^1$ in the general formula (I), provided that particularly preferred minimum number of bridge-forming atoms of $R^2$ and $R^3$ is in a range of from 1 to 3.

In the formula (II), $R^4$ represents a monovalent group or a monovalent atom. $R^4$ may be, for example, a hydrogen atom, hydroxyl group, amidino group, amino group, an alkyl group which may be substituted, an aryl group which may be substituted, a heteroaryl group which may be substituted, an aralkyl group which may be substituted, an alkyl group substituted with a heteroaryl group which may be substituted, or a group represented by any one of the following formulas (XIII) to (XVI):

—CO—R$^{25}$       (XIII)

wherein $R^{25}$ represents a hydrogen atom, a $C_{1-4}$ alkyl group which may be substituted, an aryl group which may be substituted, a heteroaryl group which may be substituted, a heterocyclic group which may be substituted, or an aralkyl group which may be substituted;

—CO—NR$^{26}$R$^{27}$       (XIV)

wherein $R^{26}$ and $R^{27}$ independently represent a hydrogen atom, a $C_{1-4}$ alkyl group which may be substituted, an aryl group which may be substituted, a heteroaryl group which may be substituted, a heterocyclic group which may be substituted, or an aralkyl group which may be substituted;

—SO$_2$—R$^{25}$       (XV)

wherein $R^{25}$ has the same meaning as that defined above; and

—SO$_2$—NR$^{26}$R$^{27}$       (XVI)

wherein $R^{26}$ and $R^{27}$ have the same meanings as those defined above.

Where $R^4$ is an alkyl group which may be substituted, the alkyl group may be linear or branched, and it may contain one or more cyclic structures or one or more unsaturated bonds. The number of carbon atoms thereof may preferably be 20 or less including its substituent(s). Particularly preferred group may contain 1 to 4 carbon atoms. Preferred examples of the substituent include, but not limited thereto, halogen atoms such as fluorine atom, chlorine atom, bromine atom, and iodine atom, hydroxyl group, carboxyl group, vinyl group, ethynyl group, $C_{3-8}$ cycloalkyl groups, carbamoyl group which may have a substituent on the nitrogen atom (one or two substituents selected from a $C_{1-6}$ alkyl group, a halogenated $C_{1-6}$ alkyl group, a hydroxy-substituted $C_{1-6}$ alkyl group, an aryl group, a sulfonyl group, a $C_{1-6}$ alkyl-substituted sulfonyl group, a $C_{1-6}$ alkanoyl group, a halogenated $C_{1-6}$ alkanoyl group, a hydroxy-substituted $C_{1-6}$ alkanoyl group, an alkoxy-substituted $C_{1-6}$ alkanoyl group and the like), a sulfamoyl group which may have a substituent on the nitrogen atom (one or two substituents selected from those exemplified for the aforementioned carbamoyl group), $C_{1-20}$ alkanoyl groups, aroyl groups, heteroarylcarbonyl groups, $C_{1-20}$ alkanoylamino groups, aroylamino groups, heteroarylcarbonylamino groups, $C_{1-20}$ alkylsulfonyl groups, arylsulfonyl groups, heteroarysulfonyl groups, $C_{1-20}$ alkylsulfonylamino groups, arylsulfonylamino groups, heteroarylsulfonylamino groups, an ureido group which may have a substituent on the nitrogen atom (one or two substituents selected from those exemplified for the aforementioned carbamoyl group), a cyano group, an amino group which may have a substituent on the nitrogen atom (one or two substituents selected from those exemplified for the aforementioned carbamoyl group), $C_{1-20}$ alkylthio groups, $C_{1-20}$ alkoxyl groups, aryloxy groups, heteroaryloxy groups, arylthio groups, arylthio groups substituted with one to three hydroxyl groups, $C_{1-20}$ alkoxycarbonyl groups, aryloxycarbonyl groups, heteroaryloxycarbonyl groups, a 2-hydroxyethoxy group, polyether groups (2-methoxyethoxy group, 2-(2-methoxyethoxy) ethoxy group etc.), a succinimido group, a guanidino group, aryl groups, aryl groups which are substituted with one or two hydroxyl groups, aryl groups which are substituted with 1 to 5 independently selected halogen atoms (a halogen atom has the same meaning as that defined above), heteroaryl groups, heterocyclic groups and the like.

The aryl group of the aforementioned aryl group, aroyl group, aroylamino group, arylsulfonyl group, arylsulfonylamino group, aryloxy group, and aryloxycarbonyl group, and the heteroaryl group of the aforementioned heteroaryl group, heteroarylcarbonyl group, heteroarylsulfonyl group, heteroarylsulfonylamino group, heteroaryloxy group, and heteroaryloxycarbonyl group have the same meanings as those defined above. Examples of the heterocyclic group include, for example, dioxolanyl group, morpholino group, morpholyl group, piperidyl group, dioxanyl group, imidazolyl group, thiazolyl group, pyrimidinyl group, 2,2-dimethyl-1,3-dioxolanyl group and the like.

Preferred examples of $R^4$ include, but not limited thereto, methyl group, ethyl group, propyl group, sec-butyl group, cyclopropylmethyl group, allyl group, propargyl group, 2-fluoroethyl group, 2,2,2-trifluoroethyl group, 2-hydroxyethyl group, 3-hydroxypropyl group, carbamoylmethyl group, 2-carbamoylethyl group, 2-(N,N-dimethylcarbamoyl)ethyl group, 2-(N-morpholinocarbonyl) ethyl group, 2-(N-piperidinocarbonyl)ethyl group, sulfamoylmethyl group, acetylmethyl group, 2-(N-acetylamino)ethyl group, cyanomethyl group, 2-(N,N-diethylamino)ethyl group, 2-(N-morpholino)ethyl group, 2-(N-piperidino)ethyl group, 2-methylthioethyl group, 2-methoxyethyl group, hydroxyethoxyethyl group, methoxycarbonylmethyl group and the like.

When $R^4$ is an aryl group which may be substituted, the number of carbon atom is preferably 20 or less including its substituent(s). Preferred examples include, for example, phenyl group which may be substituted and naphthyl group which may be substituted. When these groups have a substituent, they may have one to three substituents. Preferred examples of the substituent are those exemplified as preferred substituents for $R^4$ when it represents the alkyl group. Among them, halogen atoms, hydroxyl group, carbamoyl group and the like are particularly preferred. When $R^4$ is a heteroaryl group which may be substituted, the number of carbon atoms is preferably 20 or less including its substituent(s). Preferred examples include, for example, pyridyl group, thienyl group, furyl group, imidazolyl group, quinolyl group and the like. These groups may have one to three substituents selected from those exemplified as preferred substituents for $R^4$ when it represents the alkyl group.

Where $R^4$ is an aralkyl group which may be substituted or an alkyl group substituted with a heteroaryl group which may be substituted, the number of carbon atoms thereof is preferably 20 or less including their substituent(s). Preferred examples include, for example, benzyl group, 2-phenylethyl group, naphthylmethyl group, 2-picolyl group, 3-picolyl group, (2-furyl)methyl group, (2-thienyl)methyl group, (2-quinolyl)methyl group, 2-(2-pyridyl)ethyl group, 2-(N-imidazolyl)ethyl group and the like. These groups may have one to three substituents selected from those exemplified as preferred substituents for $R^4$ when it represents the alkyl group. Among them, halogen atoms, hydroxyl group, carbamoyl group and the like are particularly preferred substituents.

Where $R^4$ is a group represented by the formula (XIII) or the formula (XV), the group represented by $R^{25}$ preferably has 15 or less carbon atoms, and it may have one to three substituents selected from those exemplified as preferred substituents for $R^4$ when it represents the alkyl group. The aryl group, heteroaryl group, heterocyclic group and aralkyl group for $R^{25}$ have the same meanings as those defined above. Preferred examples of $R^4$ include, for example, acetyl group, propionyl group, benzoyl group, 2-pyridylcarbonyl group, 3-pyridylcarbonyl group, 4-pyridylcarbonyl group, benzylcarbonyl group, methanesulfonyl group, benzenesulfonyl group and the like.

Where $R^4$ is a group represented by the formula (XIV) or the formula (XVI), those groups represented by $R^{26}$ and $R^{27}$ preferably have 15 or less carbon atoms, and they may have one to three substituents selected from those exemplified as preferred substituents for $R^4$ when it represents the alkyl group. In addition, $R^{26}$ and $R^{27}$ may bind to each other to form a ring structure. Preferred examples of $R^4$ include, for example, aminocarbonyl group, N-methylaminocarbonyl group, N-phenylaminocarbonyl group, N-(2-pyridylamino)

carbonyl group, N,N-dimethylaminocarbonyl group, N,N-diethylaminocarbonyl group, N-morpholinocarbonyl group, N-piperidinocarbonyl group, aminosulfonyl group, N,N-dimethylaminosulfonyl group, N,N-diethylaminosulfonyl group, N-morpholinosulfonyl group, N-piperidinosulfonyl group and the like.

The ring structure which is formed by $R^4$ together with $R^2$ or $R^3$ includes saturated and unsaturated ring structures. Examples of the ring include, for example, saturated or unsaturated 3- to 18-membered monocyclic rings or condensed rings, such as pyrrole ring, piperidine ring, indole ring, pyridine ring, triazine ring, pyrimidine ring, quinoline ring, oxazine ring, indazole ring, and thiazole ring. These rings may be partially or fully reduced or oxidized. Furthermore, they may further bind to one or two $C_{1-4}$ alkylene groups to form a divalent group.

A compound in which one monovalent group such as an alkyl group further bind to a nitrogen atom in the general formula (II) to form a quaternary salt of the nitrogen atom may also be used as an active ingredient of the medicament for treatment of cancer of the present invention. As a counter ion of the quaternary salt, for example, iodine ion, bromine ion, chloride ion, perchlorate ion, sulfate ion, phosphate ion, sulfamate ion, acetate ion, lactate ion, citrate ion, tartrate ion, malonate ion, methanesulfonate ion, ethanesulfonate ion, hydroxyethanesulfonate ion, benzenesulfonate ion, p-toluenesulfonate ion, and cyclohexylsulfamate ion may be used. Iodine ion, bromine ion, chloride ion, and perchlorate ion can be preferably used. As the monovalent group, $C_{1-6}$ alkyl groups such as methyl group are preferred.

Divalent groups preferred as $R^1$, $R^2$, and $R^3$ in the general formula (I) and (II) will be exemplified blow. However, the divalent group which can be used for the compound as the active ingredient of the medicament for treatment of cancer of the present invention is not limited to these examples (in the structures, Me represents methyl group).

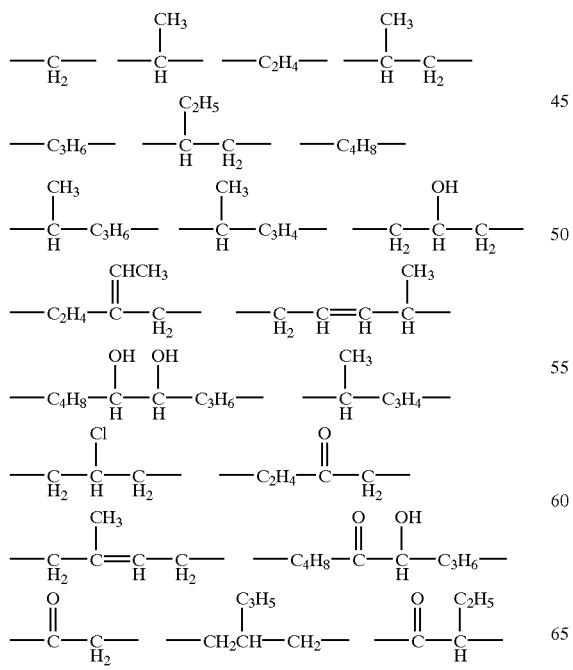

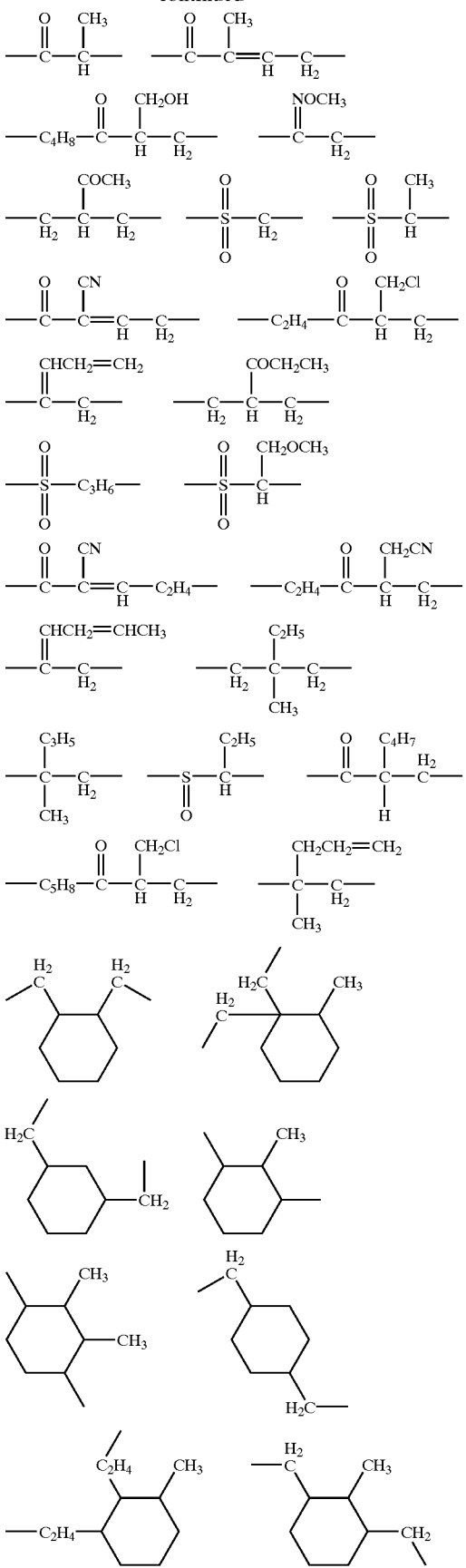

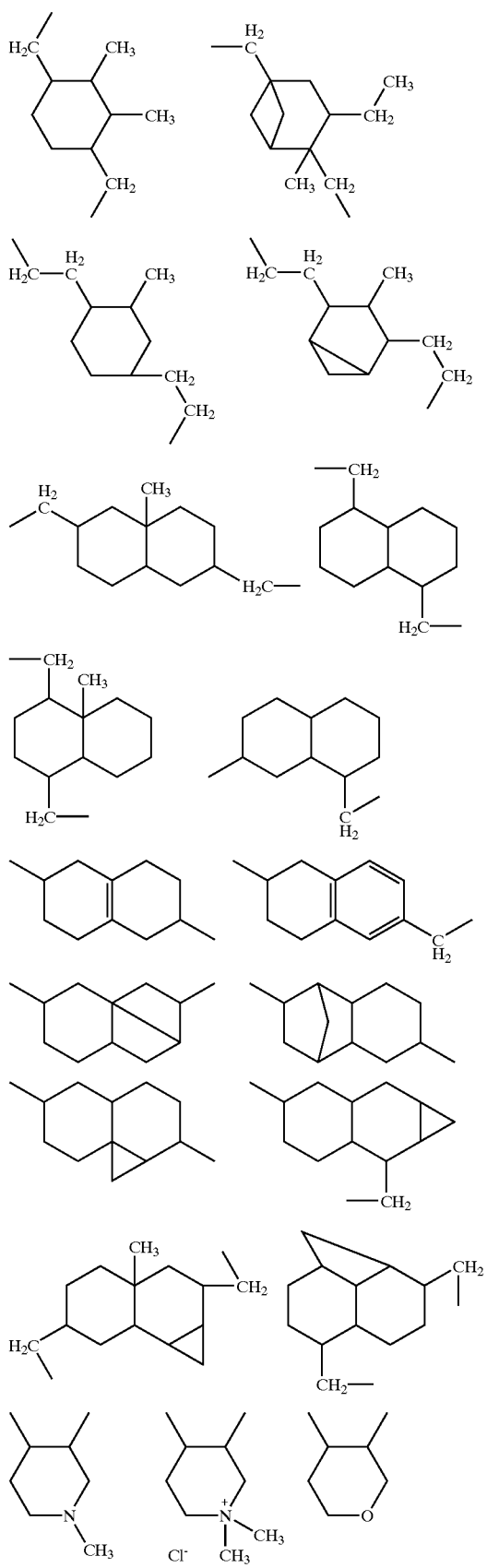
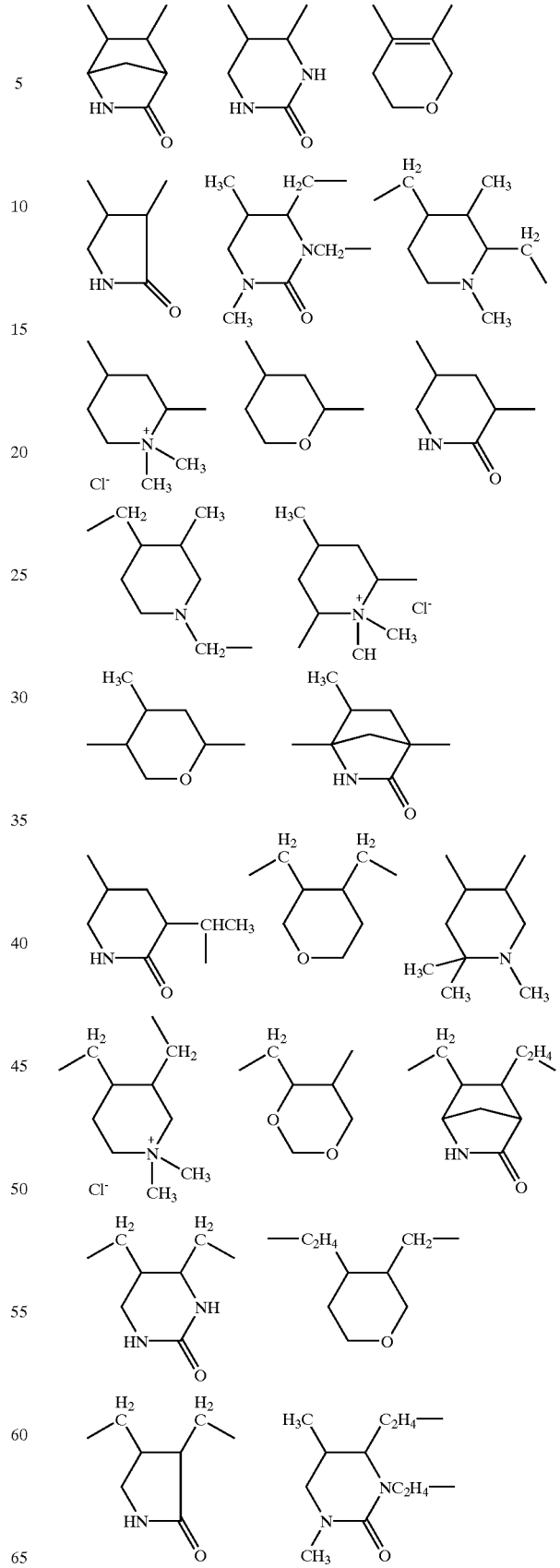

-continued
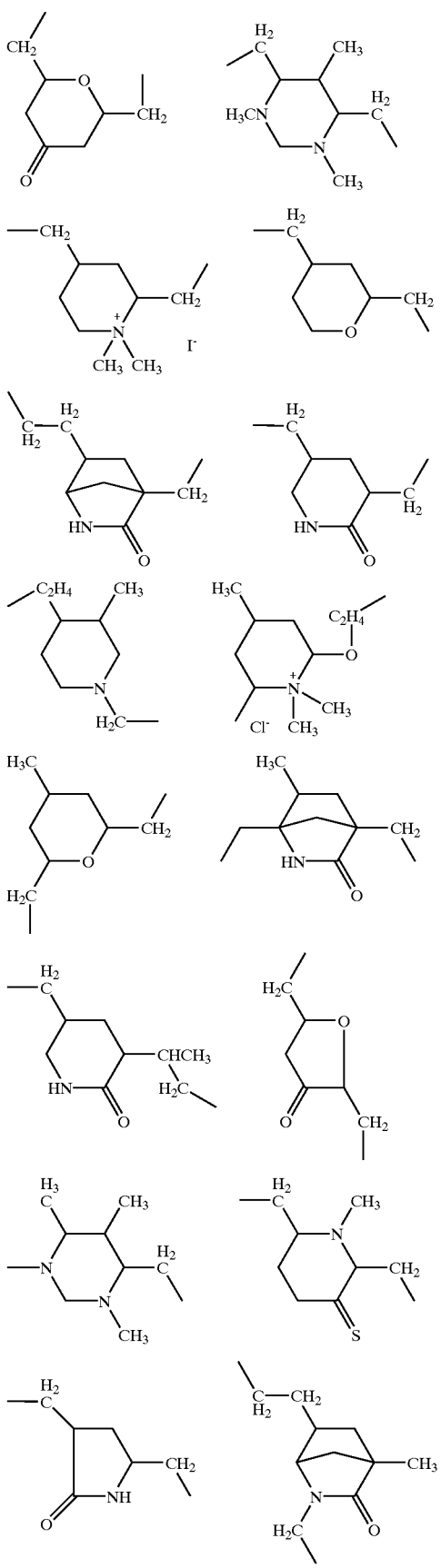
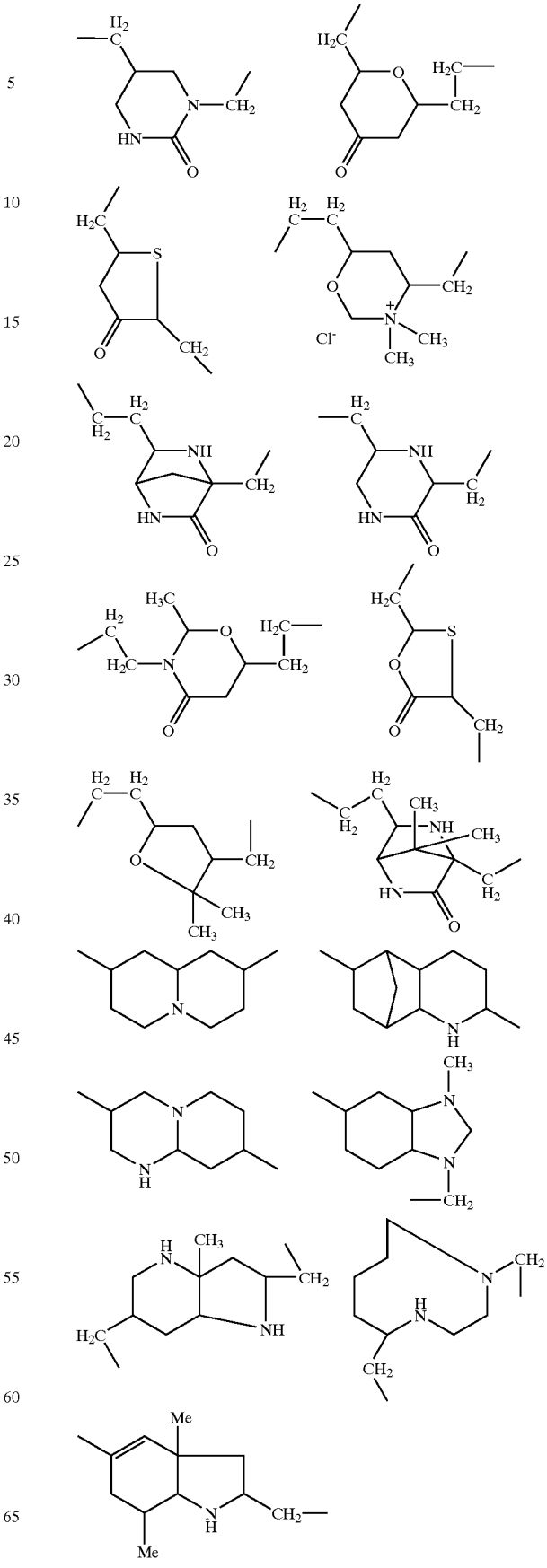

-continued
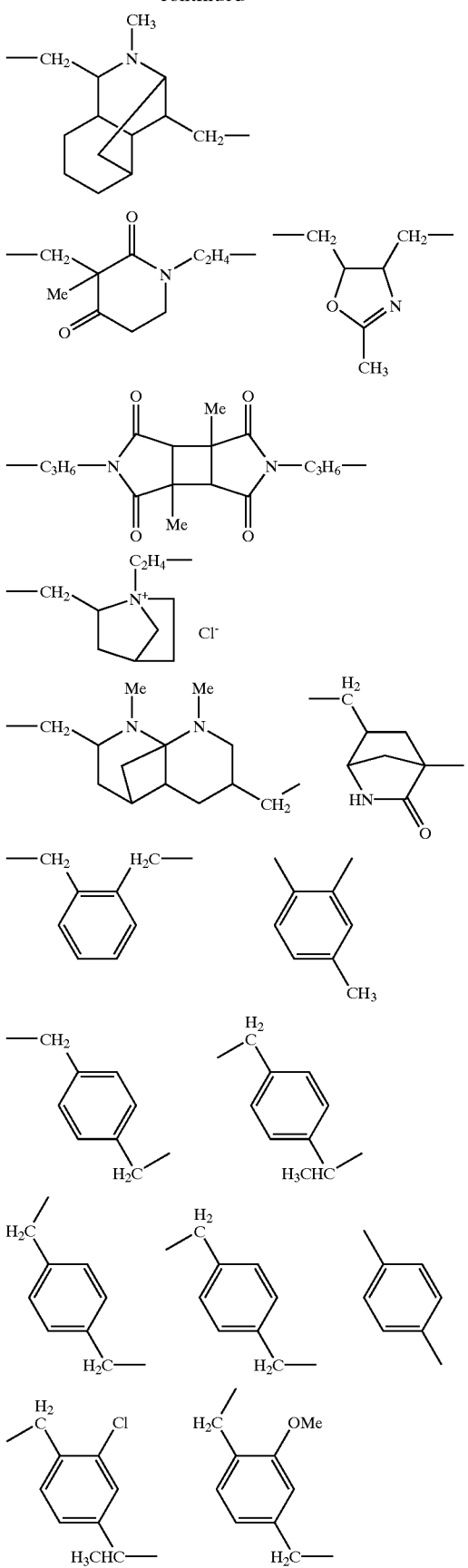
-continued
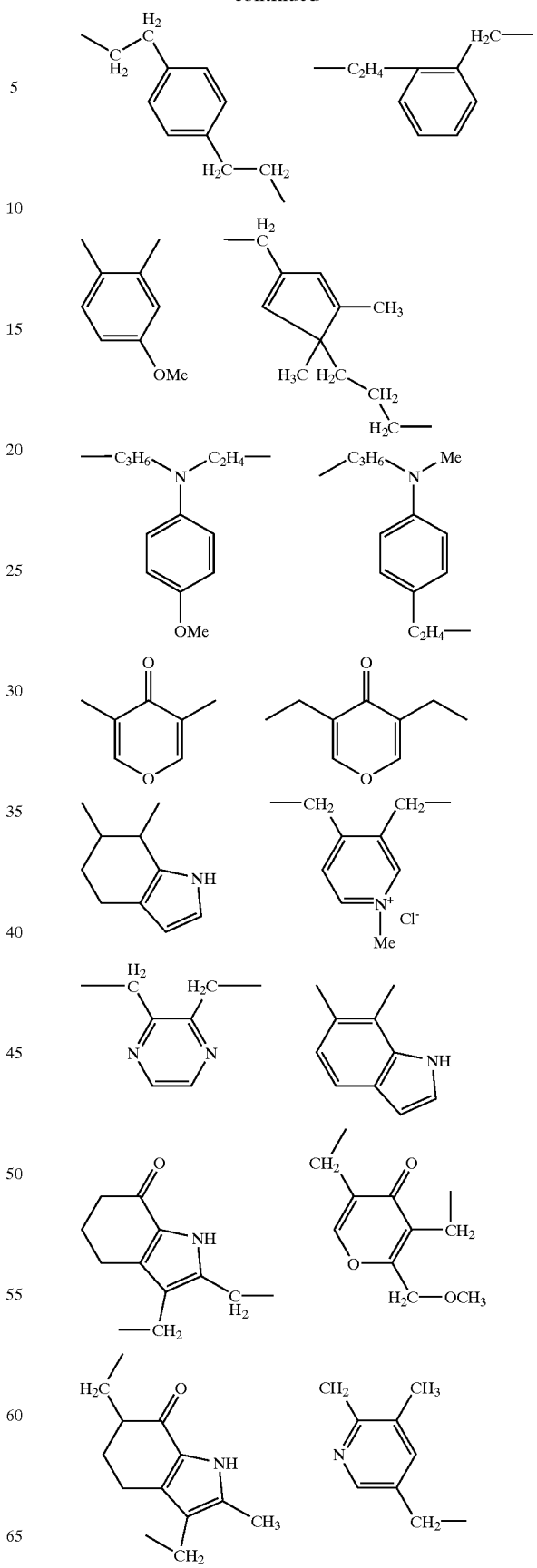

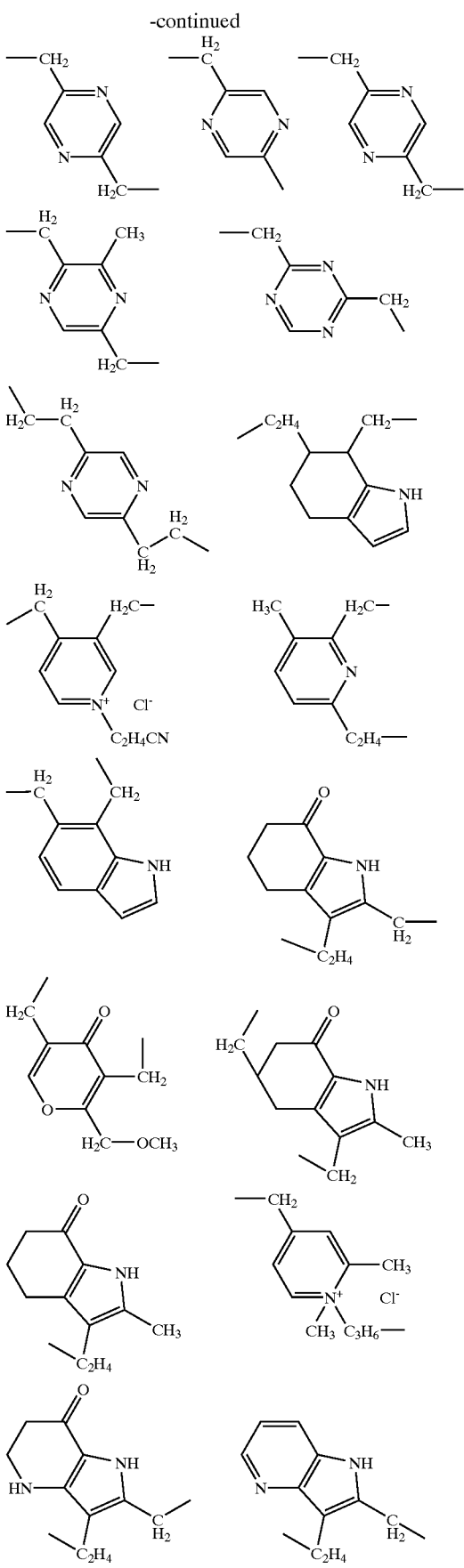
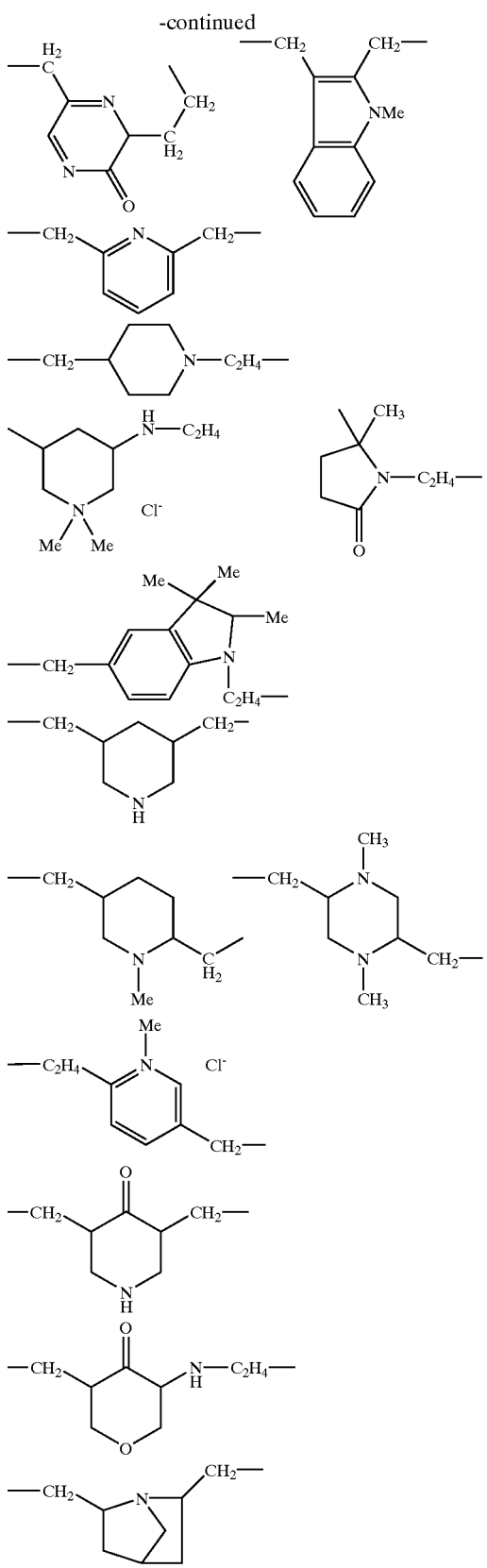
The bisaryl compounds represented by the aforementioned general formula (I) have inhibitory activity against ribonucleotide reductase, and can selectively inhibit cancer cell proliferation. Therefore, they can be used as an active ingredient of a medicament for treatment of cancer, which can be administered to mammals including human. Types of cancers to be treated by the medicament of the present invention are not particularly limited, and the medicament can be applied to solid cancers such as stomach cancer, lung cancer, colon cancer, liver cancer, kidney cancer, breast cancer, uterus cancer, skin cancer and brain tumor, as well as non-solid cancers such as leukemia and lymphoma.

In addition, they are also useful as an active ingredient of medicaments for preventive and/or therapeutic treatment of various diseases in mammals including human accompanied by unusual expression of ribonucleotide reductases deriving from host mammals themselves, viruses, bacteria and the like, for example, herpes syndrome caused by unusual proliferation of herpes simplex virus, acquired immune deficiency syndrome caused by unusual proliferation of AIDS virus and the like. Furthermore, the aforementioned compounds, per se, can also be used as ribonucleotide reductase inhibitors such as reagents in the fields of biochemistry, pharmacology, genetic engineering and the like. As the active ingredient of the medicament of the present invention, a substance selected from the group consisting of the compounds of the aforementioned general formula (I) and salts thereof, and hydrates thereof and solvates thereof can be used, as well as any combinations of two or more of substances selected from said group.

Although the aforementioned substances, per se, may be used as the medicament of the present invention, it is generally preferred that the medicament is provided for administration as a pharmaceutical composition that can be prepared by using one or more pharmaceutically acceptable additives. Administration route of the medicament of the present invention is not particularly limited, and oral or parenteral administration may be selected. Examples of the pharmaceutical compositions suitable for parenteral administration include, for example, injections suitable for intravenous, intraarterial, intraperitoneal or intrapleural injection, drip infusions, preparations for intrarectal administration (suppositories) and the like. Examples of the pharmaceutical compositions suitable for oral administration include, for example, tablets, capsules, granules, powders, syrups and the like. However, applicable pharmaceutical compositions are not limited to these examples, and those skilled in the art can select a suitable form of composition from available pharmaceutical compositions.

For example, for the manufacture of injections, the aforementioned substances as an active ingredient may be dissolved in a diluent available to those skilled in the art (for example, physiological saline, glucose solution for injection, lactose solution for injection, mannitol solution for injection and the like), and then the solution may be subjected to an appropriate sterilization treatment such as filtration sterilization, and filled in hermetic containers such as ampoules. Preparation for injection in a lyophilized form or powder for injection mixed with sodium chloride may also be prepared according to the Japanese Pharmacopoeia. As the pharmaceutical additives, for example, carriers such as auxiliaries such as polyethylene glycol and HCO-60 (surfactant; Nikko Chemical Co. Ltd.), ethanol and/or liposome and cyclodextrin may be incorporated. Pharmaceutical compositions suitable for oral administration or intrarectal administration can be prepared by mixing the aforementioned substances with appropriate pharmaceutical additives such as excipients, disintegrating agents, binders, lubricants, suspending agents, isotonic agents, and emulsifiers in a conventional manner, and formulating the mixture into an appropriate form.

Dosage and administration frequency of the medicament of the present invention are not particularly limited. When the medicament of the present invention is used for treatment of cancer, it can be administered, for example, via intravenous route in an amount of 0.01 to 100 mg/kg (based on the weight of the active ingredient) at intervals of every week to every 3 weeks. It is desirable to suitably adjust the dosage and administration frequency depending on various conditions, for example, route of administration, a kind of an active ingredient, i.e., the compound of the aforementioned formulas (I) to (III), the age and body weight of patients, the condition, and frequency and severity of side effects such as bone marrow suppression.

The bisaryl compounds represented by the aforementioned general formula (I) may have one to three asymmetric carbons depending on the kind of the substituents. Furthermore, a sulfur atom may also serve as an asymmetric center. Any optical isomers in an optically pure form based on one to three asymmetric carbons, any mixtures of the aforementioned optical isomers, and racemates, as well as diastereomers based on two or more asymmetric carbons, any mixtures of such diastereomers and the like may be used as the active ingredient of the medicament of the present invention. As the active ingredient of the medicament of the present invention, those in free form encompassed by the aforementioned formula as well as physiologically acceptable salts thereof may be used.

Examples of such salts include, for example, hydrochlorides, sulfates, phosphates, sulfamates, acetates, lactates, citrates, tartrates, malonates, methanesulfonates, ethanesulfonates, hydroxyethanesulfonates, benzenesulfonates, p-toluenesulfonates, cyclohexylsulfamates and the like. These salts can be prepared by dissolving the aforementioned compound as free base in water, an aqueous organic solvent such as alcoholic solvent or a suitable organic solvent containing a corresponding acid to form a uniform solution, and isolating a salt after evaporation of water or the organic solvent, or allowing the compound in free form to react with an acid in an organic solvent. In the latter case, for example, the resulting salt can be directly isolated, or recovered by evaporation of the solvent. As the active ingredient of the medicament of the present invention, the aforementioned compounds in free form and salts thereof, and in addition, hydrates thereof and solvates thereof can be used. Examples of the organic solvent for forming the solvates include, for example, physiologically acceptable solvents such as ethanol and ethylene glycol.

Specific examples of the compounds most suitably used for the medicament of the present invention will be listed below. However, the active ingredient of the medicament of the present invention is not limited to the following compounds (in the tables, the serial numbers in the first left column indicate the compound numbers, Ph represents phenyl group, and p-HO-Ph represents p-hydroxyphenyl group. In Table 3, "B" represents p-hydroxyphenylthio group, Me represents methyl group, Et represents ethyl group, and Ac represents acetyl group).

TABLE 1
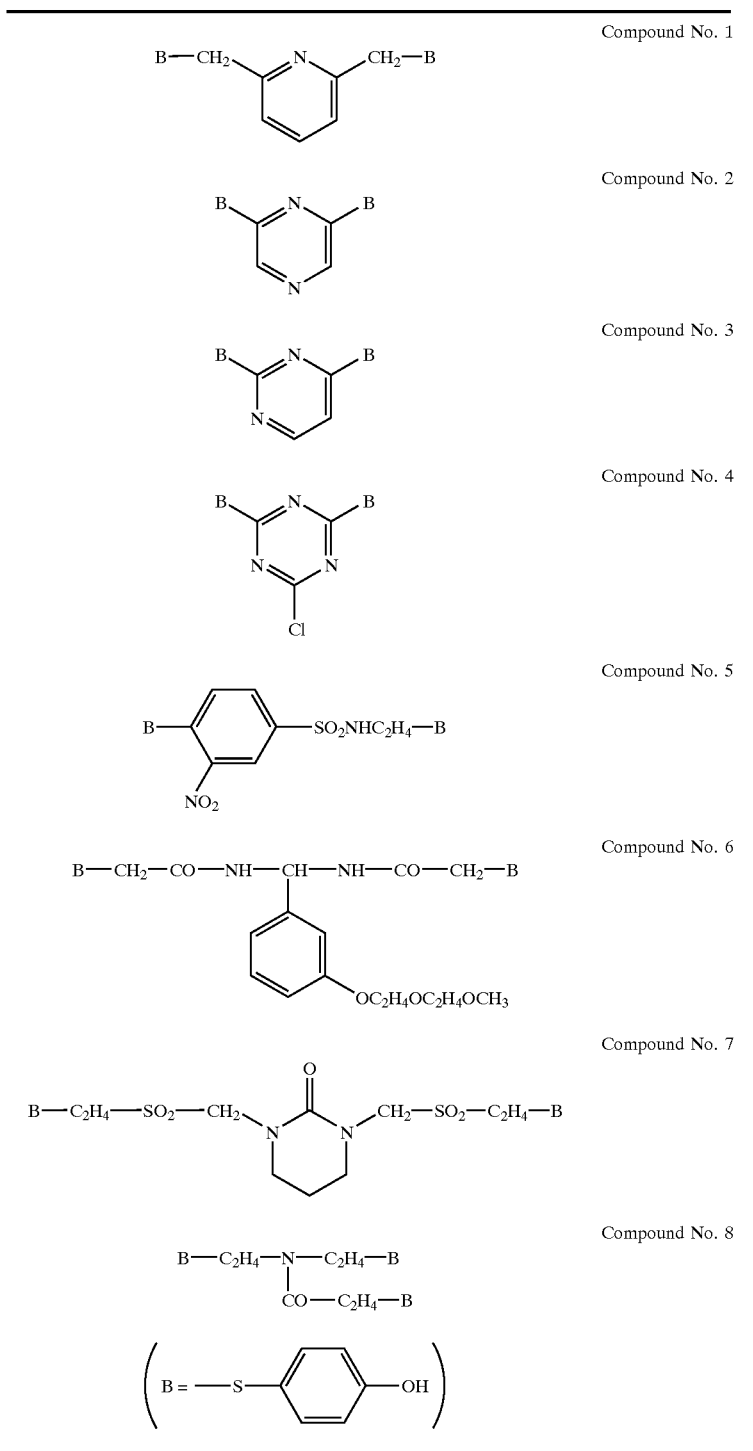
| Compound No. | Ar¹ | R¹ | Ar¹ |
|---|---|---|---|
| 9 | p-HO—Ph— | —$C_2H_4$—S—$C_2H_4$— | p-HO—Ph— |
| 10 | p-HO—Ph— | —$C_2H_4$—S—$C_3H_6$— | p-HO—Ph— |
| 11 | p-HO—Ph— | —$C_2H_4$—S—$C_4H_4$— | p-HO—Ph— |
| 12 | p-HO—Ph— | —$C_2H_4$—S—$C_4H_6$— | p-HO—Ph— |
| 13 | p-HO—Ph— | —$C_2H_4$—S—$C_4H_8$— | p-HO—Ph— |
| 14 | p-HO—Ph— | —$C_3H_6$—S—$C_3H_6$— | p-HO—Ph— |
| 15 | p-HO—Ph— | —$C_3H_6$—S—$C_4H_6$— | p-HO—Ph— |
| 16 | p-HO—Ph— | —$C_3H_6$—S—$C_4H_8$— | p-HO—Ph— |

TABLE 1-continued

| | | | | |
|---|---|---|---|---|
| 17 | p-HO—Ph— | —C$_4$H$_8$—S—C$_4$H$_8$— | | p-HO—Ph— |
| 18 | p-HO—Ph— | —CH$_2$CO—S—C$_2$H$_4$— | | p-HO—Ph— |
| 19 | p-HO—Ph— | —CH$_2$CO—S—C$_3$H$_6$— | | p-HO—Ph— |
| 20 | p-HO—Ph— | —CH$_2$CO—S—C$_4$H$_8$— | | p-HO—Ph— |
| 21 | p-HO—Ph— | —CH$_2$CO—S—C$_4$H$_6$— | | p-HO—Ph— |
| 22 | p-HO—Ph— | —CH$_2$CO—S—C$_4$H$_4$— | | p-HO—Ph— |
| 23 | p-HO—Ph— | —CH(CH$_3$)CO—S—C$_2$H$_4$— | | p-HO—Ph— |
| 24 | p-HO—Ph— | —C$_2$H$_4$CO—S—CH$_2$CH(OH)CH$_2$— | | p-HO—Ph— |
| 25 | p-HO—Ph— | —CH$_2$CO—S—C$_2$H$_4$NHCOCH$_2$— | | p-HO—Ph— |
| 26 | p-HO—Ph— | —C$_2$H$_4$CO—S—C$_2$H$_4$NHCOC$_2$H$_4$— | | p-HO—Ph— |
| 27 | p-HO—Ph— | —C$_2$H$_4$—O—C$_2$H$_4$— | | p-HO—Ph— |
| 28 | p-HO—Ph— | —C$_2$H$_4$—O—C$_3$H$_6$— | | p-HO—Ph— |
| 29 | p-HO—Ph— | —C$_2$H$_4$—O—C$_4$H$_4$— | | p-HO—Ph— |
| 30 | p-HO—Ph— | —C$_2$H$_4$—O—C$_4$H$_6$— | | p-HO—Ph— |
| 31 | p-HO—Ph— | —C$_2$H$_4$—O—C$_4$H$_8$— | | p-HO—Ph— |
| 32 | p-HO—Ph— | —C$_3$H$_6$—O—C$_3$H$_6$— | | p-HO—Ph— |
| 33 | p-HO—Ph— | —C$_3$H$_6$—O—C$_4$H$_6$— | | p-HO—Ph— |
| 34 | p-HO—Ph— | —C$_3$H$_6$—O—C$_4$H$_8$— | | p-HO—Ph— |
| 35 | p-HO—Ph— | —C$_4$H$_8$—O—C$_4$H$_8$— | | p-HO—Ph— |
| 36 | p-HO—Ph— | —CH$_2$CO—O—C$_2$H$_4$— | | p-HO—Ph— |
| 37 | p-HO—Ph— | —CH$_2$CO—O—C$_3$H$_6$— | | p-HO—Ph— |
| 38 | p-HO—Ph— | —CH$_2$CO—O—C$_4$H$_8$— | | p-HO—Ph— |
| 39 | p-HO—Ph— | —CH$_2$CO—O—C$_4$H$_6$— | | p-HO—Ph— |
| 40 | p-HO—Ph— | —CH$_2$CO—O—C$_4$H$_4$— | | p-HO—Ph— |
| 41 | p-HO—Ph— | —CH(CH$_3$)CO—O—C$_2$H$_4$— | | p-HO—Ph— |
| 42 | p-HO—Ph— | —C$_2$H$_4$CO—O—CH$_2$CH(OH)CH$_2$— | | p-HO—Ph— |
| 43 | p-HO—Ph— | —CH$_2$CO—O—C$_2$H$_4$NHCOCH$_2$— | | p-HO—Ph— |
| 44 | p-HO—Ph— | —C$_2$H$_4$CO—O—C$_2$H$_4$NHCOC$_2$H$_4$— | | p-HO—Ph— |

TABLE 2

| Compound No. | Ar$^1$ | R$^2$ | R$^3$ | R$^4$ | Ar$^2$ |
|---|---|---|---|---|---|
| 45 | p-HO—Ph— | —C$_2$H$_4$— | —C$_2$H$_4$— | —H | p-HO—Ph— |
| 46 | p-HO—Ph— | —C$_3$H$_6$— | —C$_3$H$_6$— | —H | p-HO—Ph— |
| 47 | p-HO—Ph— | —C$_4$H$_8$— | —C$_4$H$_8$— | —H | p-HO—Ph— |
| 48 | p-HO—Ph— | —C$_2$H$_4$— | —C$_2$H$_4$— | —OH | p-HO—Ph— |
| 49 | p-HO—Ph— | —C$_2$H$_4$— | —C$_2$H$_4$— | —C(=NH)NH$_2$ | p-HO—Ph— |
| 50 | p-HO—Ph— | —C$_2$H$_4$— | —C$_2$H$_4$— | —COC$_3$H$_7$ | p-HO—Ph— |
| 51 | p-HO—Ph— | —C$_2$H$_4$— | —C$_2$H$_4$— | —COCH$_2$CH$_2$CO$_2$H | p-HO—Ph— |
| 52 | p-HO—Ph— | —C$_2$H$_4$— | —C$_2$H$_4$— | —COCH$_2$CH$_2$S—Ph—OH-p | p-HO—Ph— |
| 53 | p-HO—Ph— | —C$_2$H$_4$— | —C$_2$H$_4$— | —CHO | p-HO—Ph— |
| 54 | p-HO—Ph— | —C$_2$H$_4$— | —C$_2$H$_4$— | —COCH$_3$ | p-HO—Ph— |
| 55 | p-HO—Ph— | —C$_2$H$_4$— | —C$_2$H$_4$— | —SO$_2$CH$_3$ | p-HO—Ph— |
| 56 | p-HO—Ph— | —C$_3$H$_6$— | —C$_3$H$_6$— | —CHO | p-HO—Ph— |
| 59 | p-HO—Ph— | —C$_2$H$_4$— | —C$_2$H$_4$— | —CH$_2$CH$_2$NH$_2$ | p-HO—Ph— |
| 60 | p-HO—Ph— | —CH$_2$CO— | —C$_2$H$_4$— | —H | p-HO—Ph— |
| 61 | p-HO—Ph— | —CH$_2$CO— | —C$_3$H$_6$— | —H | p-HO—Ph— |
| 62 | p-HO—Ph— | —CH$_2$CO— | —C$_4$H$_8$— | —H | p-HO—Ph— |
| 63 | p-HO—Ph— | —CH$_2$CO— | —C$_4$H$_6$— | —H | p-HO—Ph— |
| 64 | p-HO—Ph— | —CH$_2$CO— | —C$_4$H$_4$— | —H | p-HO—Ph— |
| 65 | p-HO—Ph— | —CH$_2$CO— | —C$_4$H$_4$— | —CHO | p-HO—Ph— |
| 66 | p-HO—Ph— | —CH(CH$_3$)CO— | —C$_2$H$_4$— | —H | p-HO—Ph— |
| 67 | p-HO—Ph— | —CH(CH$_3$)CO— | —C$_2$H$_4$— | —C$_2$H$_4$OH | p-HO—Ph— |
| 68 | p-HO—Ph— | —C$_2$H$_4$CO— | —CH$_2$CH(OH)CH$_2$— | —C$_2$H$_4$OH | p-HO—Ph— |
| 69 | p-HO—Ph— | —CH$_2$CO— | —C$_2$H$_4$NHCOCH$_2$— | —H | p-HO—Ph— |
| 70 | p-HO—Ph— | —C$_2$H$_4$CO— | —C$_2$H$_4$NHCOC$_2$H$_4$— | —H | p-HO—Ph— |
| 71 | p-HO—Ph— | —C$_2$H$_4$— | —C$_2$H$_4$— | —C$_2$H$_5$ | p-HO—Ph— |
| 72 | p-HO—Ph— | —C$_2$H$_4$— | —C$_2$H$_4$— | —C$_3$H$_7$ | p-HO—Ph— |
| 73 | p-HO—Ph— | —C$_2$H$_4$— | —C$_2$H$_4$— | —CH$_2$—C≡CH | p-HO—Ph— |
| 74 | p-HO—Ph— | —C$_2$H$_4$— | —C$_2$H$_4$— | —CH$_2$—CH=CH$_2$ | p-HO—Ph— |
| 75 | p-HO—Ph— | —C$_2$H$_4$— | —C$_2$H$_4$— | —CH$_2$-cyclopropyl | p-HO—Ph— |
| 76 | p-HO—Ph— | —C$_2$H$_4$— | —C$_2$H$_4$— | —CH$_2$—SO$_2$NH$_2$ | p-HO—Ph— |
| 77 | p-HO—Ph— | —C$_2$H$_4$— | —C$_2$H$_4$— | —CH$_2$—CN | p-HO—Ph— |
| 78 | p-HO—Ph— | —C$_2$H$_4$— | —C$_2$H$_4$— | —C$_2$H$_4$—CO—NH$_2$ | p-HO—Ph— |
| 79 | p-HO—Ph— | —C$_2$H$_4$— | —C$_2$H$_4$— | —C$_2$H$_4$—CO—N(CH$_3$)$_2$ | p-HO—Ph— |
| 80 | p-HO—Ph— | —C$_2$H$_4$— | —C$_2$H$_4$— | —C$_2$H$_4$—CO—N(C$_2$H$_5$)$_2$ | p-HO—Ph— |
| 81 | p-HO—Ph— | —C$_2$H$_4$— | —C$_2$H$_4$— | —CH$_2$—CO—CH$_3$ | p-HO—Ph— |
| 82 | p-HO—Ph— | —C$_2$H$_4$— | —C$_2$H$_4$— | —C$_2$H$_4$—NH—CO—NH$_2$ | p-HO—Ph— |
| 83 | p-HO—Ph— | —C$_2$H$_4$— | —C$_2$H$_4$— | —C$_2$H$_4$—NH—CO—CH$_3$ | p-HO—Ph— |
| 84 | p-HO—Ph— | —C$_2$H$_4$— | —C$_2$H$_4$— | —CH$_2$F | p-HO—Ph— |
| 85 | p-HO—Ph— | —C$_2$H$_4$— | —C$_2$H$_4$— | —CF$_3$ | p-HO—Ph— |
| 86 | p-HO—Ph— | —C$_2$H$_4$— | —C$_2$H$_4$— | —C$_2$H$_4$—(N-succinimido) | p-HO—Ph— |

TABLE 2-continued

| Compound No. | Ar$^1$ | R$^2$ | R$^3$ | R$^4$ | Ar$^2$ |
|---|---|---|---|---|---|
| 87 | p-HO—Ph— | —C$_2$H$_4$— | —C$_2$H$_4$— | —C$_2$H$_4$—S—CH$_3$ | p-HO—Ph— |
| 88 | p-HO—Ph— | —C$_2$H$_4$— | —C$_2$H$_4$— | —CH$_2$-ethyleneacetal | p-HO—Ph— |
| 89 | p-HO—Ph— | —C$_2$H$_4$— | —C$_2$H$_4$— | —CH$_2$-(2-thienyl) | p-HO—Ph— |
| 90 | p-HO—Ph— | —C$_2$H$_4$— | —C$_2$H$_4$— | -furfuryl | p-HO—Ph— |
| 91 | p-HO—Ph— | —C$_2$H$_4$— | —C$_2$H$_4$— | —CH$_2$-(4-pyridyl) | p-HO—Ph— |
| 92 | p-HO—Ph— | —C$_2$H$_4$— | —C$_2$H$_4$— | -o-hydroxybenzyl | p-HO—Ph— |
| 93 | p-HO—Ph— | —C$_2$H$_4$— | —C$_2$H$_4$— | -m-hydroxybenzyl | p-HO—Ph— |
| 94 | p-HO—Ph— | —C$_2$H$_4$— | —C$_2$H$_4$— | -p-hydroxybenzyl | p-HO—Ph— |
| 95 | p-HO—Ph— | —C$_2$H$_4$— | —C$_2$H$_4$— | —(CH$_2$)$_3$—OH | p-HO—Ph— |
| 96 | p-HO—Ph— | —C$_2$H$_4$— | —C$_2$H$_4$— | —CH$_2$—NH—CO—CH$_3$ | p-HO—Ph— |
| 97 | p-HO—Ph— | —C$_2$H$_4$— | —C$_2$H$_4$— | —CH$_2$—CO—NH$_2$ | p-HO—Ph— |
| 98 | p-HO—Ph— | —C$_2$H$_4$— | —C$_2$H$_4$— | -benzyl | p-HO—Ph— |
| 99 | p-HO—Ph— | —C$_2$H$_4$— | —C$_2$H$_4$— | —CH$_2$-(3-pyridyl) | p-HO—Ph— |
| 100 | p-HO—Ph— | —C$_2$H$_4$— | —C$_2$H$_4$— | —CH$_2$-(2-pyridyl) | p-HO—Ph— |
| 101 | p-HO—Ph— | —C$_2$H$_4$— | —C$_2$H$_4$— | —CH$_2$-(2-quinolinyl) | p-HO—Ph— |
| 102 | p-HO—Ph— | —C$_2$H$_4$— | —C$_2$H$_4$— | —C$_2$H$_4$—OH | p-HO—Ph— |
| 103 | p-HO—Ph— | —C$_2$H$_4$— | —C$_2$H$_4$— | —(CH$_2$)$_3$—OCH$_3$ | p-HO—Ph— |
| 104 | p-HO—Ph— | —C$_2$H$_4$— | —C$_2$H$_4$— | —C$_2$H$_4$—OCH$_3$ | p-HO—Ph— |
| 105 | p-HO—Ph— | —C$_2$H$_4$— | —C$_2$H$_4$— | -o-fluorobenzyl | p-HO—Ph— |
| 106 | p-HO—Ph— | —C$_2$H$_4$— | —C$_2$H$_4$— | -p-fluorobenzyl | p-HO—Ph— |
| 107 | p-HO—Ph— | —C$_2$H$_4$— | —C$_2$H$_4$— | —C$_2$H$_4$—CO—(N-morpholino) | p-HO—Ph— |
| 108 | p-HO—Ph— | —C$_2$H$_4$— | —C$_2$H$_4$— | —C$_2$H$_4$—CO-(1-piperidyl) | p-HO—Ph— |
| 109 | p-HO—Ph— | —C$_2$H$_4$— | —C$_2$H$_4$— | —C$_2$H$_4$—N(C$_2$H$_5$)$_2$ | p-HO—Ph— |
| 110 | p-HO—Ph— | —C$_2$H$_4$— | —C$_2$H$_4$— | —C$_2$H$_4$—(N-morpholino) | p-HO—Ph— |
| 111 | p-HO—Ph— | —C$_2$H$_4$— | —C$_2$H$_4$— | —C$_2$H$_4$-(1-piperidyl) | p-HO—Ph— |
| 112 | p-HO—Ph— | —C$_2$H$_4$— | —C$_2$H$_4$— | —CO—CH$_3$ | p-HO—Ph— |
| 113 | p-HO—Ph— | —C$_2$H$_4$— | —C$_2$H$_4$— | —CO—C$_2$H$_5$ | p-HO—Ph— |
| 114 | p-HO—Ph— | —C$_2$H$_4$— | —C$_2$H$_4$— | —CO—C$_6$H$_5$ | p-HO—Ph— |
| 115 | p-HO—Ph— | —C$_2$H$_4$— | —C$_2$H$_4$— | —CO-(2-pyridyl) | p-HO—Ph— |
| 116 | p-HO—Ph— | —C$_2$H$_4$— | —C$_2$H$_4$— | —CO-(3-pyridyl) | p-HO—Ph— |
| 117 | p-HO—Ph— | —C$_2$H$_4$— | —C$_2$H$_4$— | —CO-(4-pyridyl) | p-HO—Ph— |
| 118 | p-HO—Ph— | —C$_2$H$_4$— | —C$_2$H$_4$— | —SO$_2$—CH$_3$ | p-HO—Ph— |
| 119 | p-HO—Ph— | —C$_2$H$_4$— | —C$_2$H$_4$— | —SO$_2$—C$_6$H$_5$ | p-HO—Ph— |
| 120 | p-HO—Ph— | —C$_2$H$_4$— | —C$_2$H$_4$— | —CO—NH$_2$ | p-HO—Ph— |
| 121 | p-HO—Ph— | —C$_2$H$_4$— | —C$_2$H$_4$— | —CO—NH(CH$_3$) | p-HO—Ph— |
| 122 | p-HO—Ph— | —C$_2$H$_4$— | —C$_2$H$_4$— | —CO—N(CH$_3$)$_2$ | p-HO—Ph— |
| 123 | p-HO—Ph— | —C$_2$H$_4$— | —C$_2$H$_4$— | —CO—N(C$_2$H$_5$)$_2$ | p-HO—Ph— |
| 124 | p-HO—Ph— | —C$_2$H$_4$— | —C$_2$H$_4$— | —CO-(N-morpholino) | p-HO—Ph— |
| 125 | p-HO—Ph— | —C$_2$H$_4$— | —C$_2$H$_4$— | —CO-(1-piperidyl) | p-HO—Ph— |
| 126 | p-HO—Ph— | —C$_2$H$_4$— | —C$_2$H$_4$— | —CO—NH—C$_6$H$_5$ | p-HO—Ph— |
| 127 | p-HO—Ph— | —C$_2$H$_4$— | —C$_2$H$_4$— | —CO—NH-(2-pyridyl) | p-HO—Ph— |
| 128 | p-HO—Ph— | —C$_2$H$_4$— | —C$_2$H$_4$— | —SO$_2$—NH$_2$ | p-HO—Ph— |
| 129 | p-HO—Ph— | —C$_2$H$_4$— | —C$_2$H$_4$— | —SO$_2$—N(C$_2$H$_5$)$_2$ | p-HO—Ph— |
| 130 | p-HO—Ph— | —C$_2$H$_4$— | —C$_2$H$_4$— | —SO$_2$-(N-morpholino) | p-HO—Ph— |

Compound No. 57

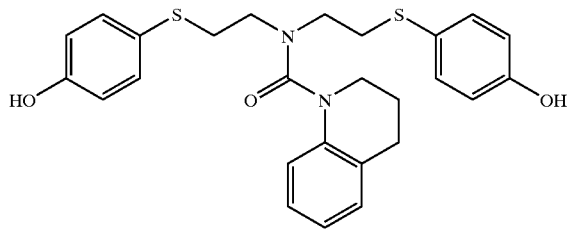

Compound No. 58

TABLE 2-continued

| Compound No. | Ar¹ | R² | R³ | R⁴ | Ar² |
|---|---|---|---|---|---|

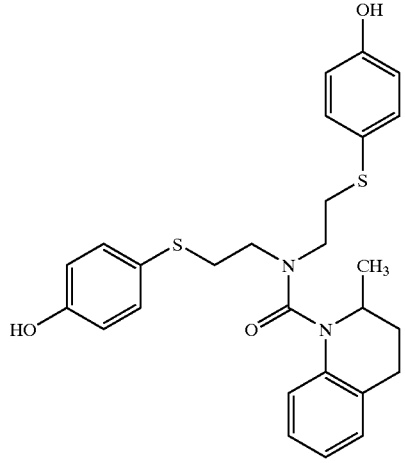

TABLE 3

| | |
|---|---|
| 131 | B—B |
| 132 | B—CH₂—B |
| 133 | B—C₂H₄—B |
| 134 | B—C₃H₆—B |
| 135 | B—C₄H₈—B |
| 136 | B—C₅H₁₀—B |
| 137 | B—C₆H₁₂—B |
| 138 | B—C₇H₁₄—B |
| 139 | B—C₈H₁₆—B |
| 140 | B—C₉H₁₈—B |
| 141 | B—C₁₀H₂₀—B |
| 142 | B—C₁₁H₂₂—B |
| 143 | B-C₂H₄—SO₂—C₂H₄—SO₂—C₂H₄—B |
| 144 | B—CH(CH₃)—B |
| 145 | B—CH(C₂H₅)—B |
| 146 | B—CH(n-C₃H₇)—B |
| 147 | B—CH(C₆H₅)—B |
| 148 | B—CH(B)(p-HOC₂H₄O—C₆H₄—) |
| 149 | B—C(CH₃)₂—B |
| 150 | B—CH(COOH)—B |
| 151 | B—CH(C₂H₄OH)—B |
| 152 | B—CH(CH₃)—CH₂—B |
| 153 | B—CH(C₂H₄OH)—CH₂—B |
| 154 | B—CH(COOH)—CH₂—B |
| 155 | B—CH(C₂H₅)—CH₂—B |
| 156 | B—CH₂—CH(OH)—CH₂—B |
| 157 | B—CH₂—C(CH₂B)₂—CH₂—B |
| 158 | B—CH₂—S—CH₂—B |
| 159 | B—CH₂—CH=CH—CH₂—B |
| 160 | B—CH₂—C≡C—CH₂—B |
| 161 | B—CH₂—C₆H₄—CH₂—B(—C₆H₄— is a o-phenylene group) |
| 162 | B—C₂H₄—O—CH₂—O—C₂H₄—B |
| 163 | B—C₂H₄—O—C₂H₄—O—C₂H₄—B |
| 164 | B—CH₂—COO—C₂H₄—OCOCH₂—B |
| 165 | B—CH₂—COO—C₃H₆—OCOCH₂—B |
| 166 | B—CH₂CH(OH)CH₂—O—C₂H₄—O—CH₂CH(OH)CH₂—B |
| 167 | B—(C₂H₄O)₂—CO—CH₂—CO—(C₂H₄O)₂—B |
| 168 | B—(C₂H₄O)₂—CO-(trans)CH=CH—CO—(C₂H₄O)₂—B |
| 169 | B—CH₂—COO—(C₂H₄O)₃—CO—CH₂—B |
| 170 | B—CH₂—COO—(C₂H₄O)4-CO—CH₂—B |
| 171 | B—(C₂H₄O)₃—C₂H₄—B |
| 172 | B—(C₂H₄O)₄—C₂H₄—B |
| 173 | B—(C₂H₄O)₅—C₂H₄—B |
| 174 | B—(C₂H₄O)₃—CO—(C₂H₄O)₃—B |
| 175 | B—(C₂H₄O)₂—CO—C₂H₄—CO—(C₂H₄O)₂—B |

TABLE 3-continued
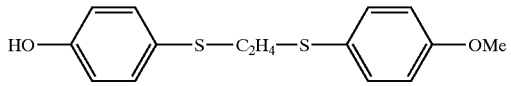 Compound No. 176
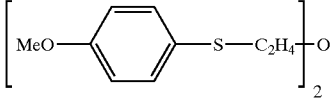 Compound No. 177
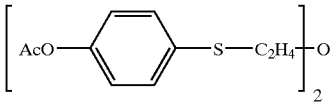 Compound No. 178
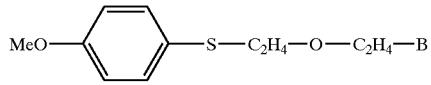 Compound No. 179
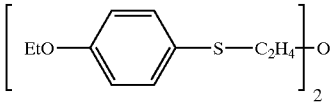 Compound No. 180
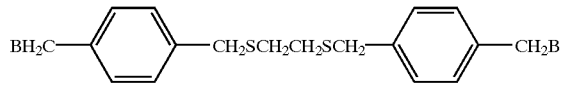 Compound No. 181
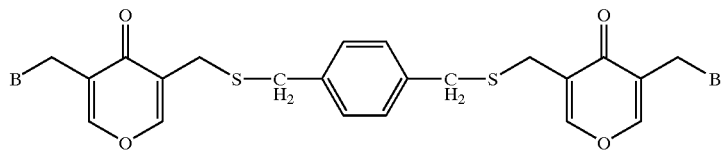 Compound No. 182
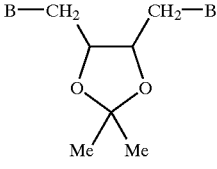 Compound No. 183
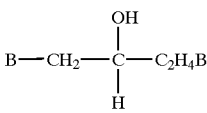 Compound No. 184
 Compound No. 185
[B—CH$_2$—CO—]$_2$  Compound No. 186
B—CO—CH$_2$—CO—B  Compound No. 187

TABLE 3-continued
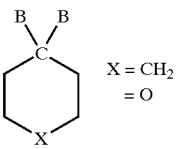
Compound No. 188
Compound No. 189
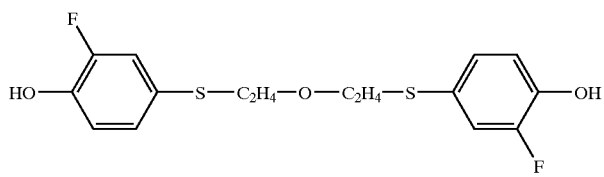
Compound No. 190
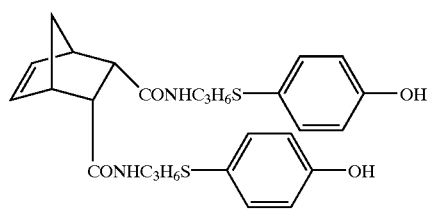
Compound No. 191
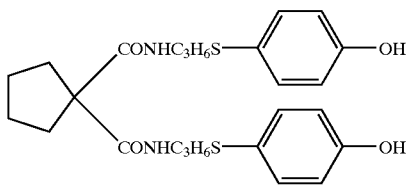
Compound No. 192
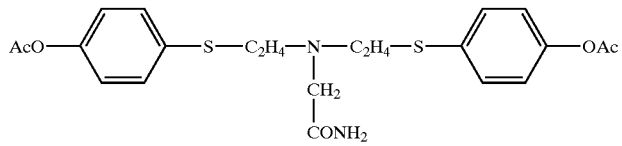
Compound No. 193
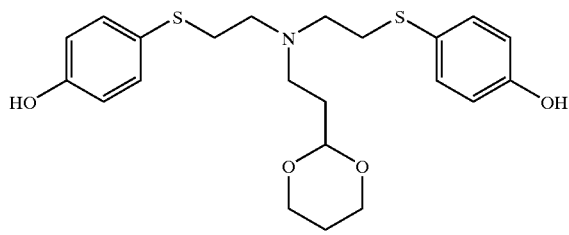
Compound No. 194
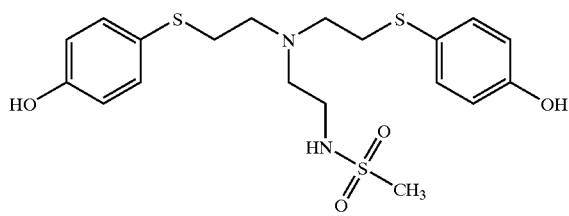
Compound No. 195
Compound No. 196

TABLE 3-continued
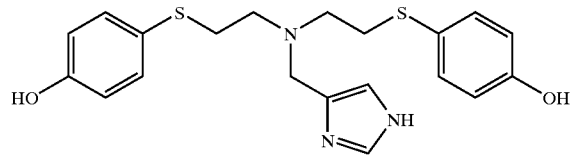
Compound No. 197
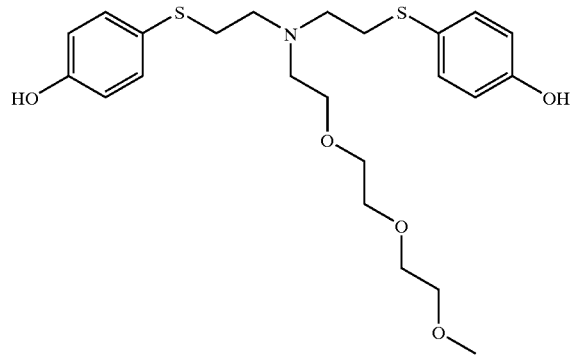
Compound No. 198
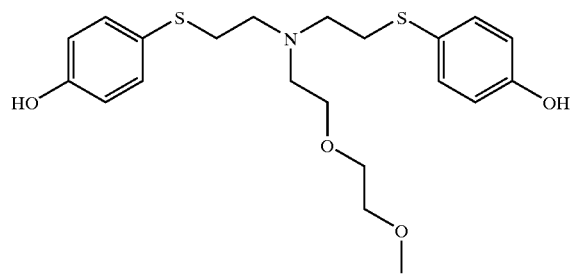
Compound No. 199
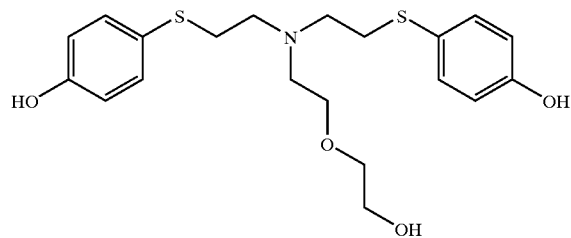
Compound No. 200
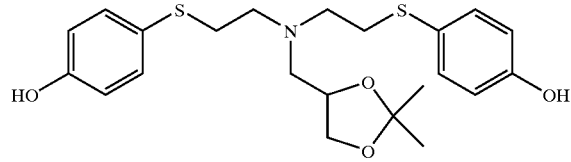
Compound No. 201
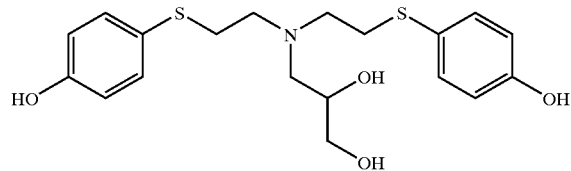
Compound No. 202

TABLE 3-continued
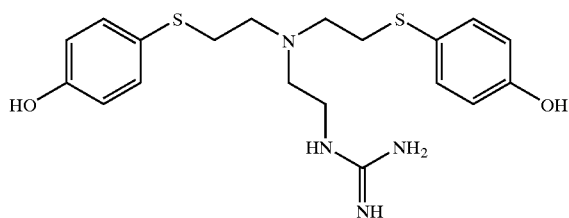
Compound No. 203
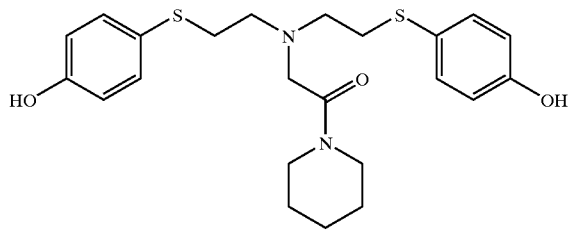
Compound No. 204
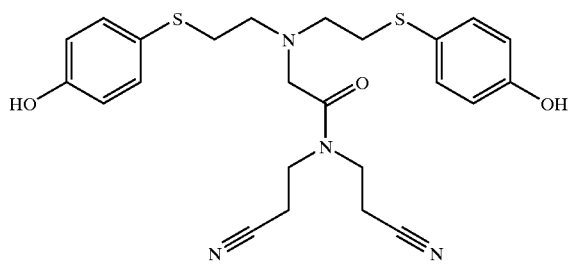
Compound No. 205
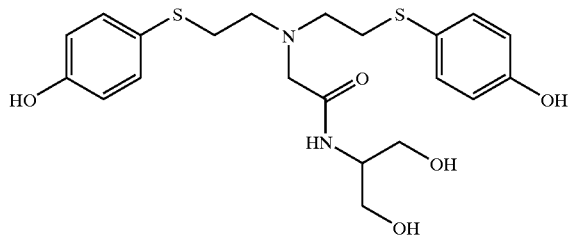
Compound No. 206
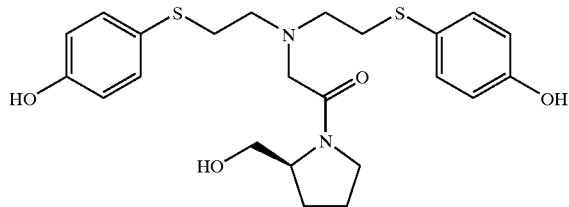
Compound No. 207
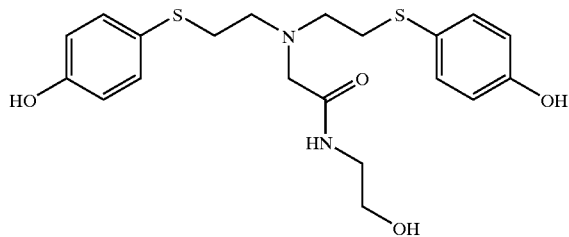
Compound No. 208

TABLE 3-continued
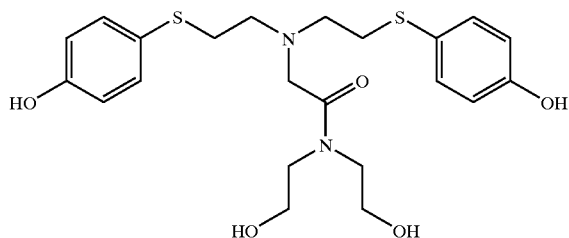
Compound No. 209
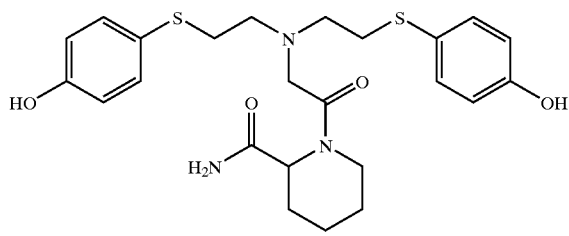
Compound No. 210
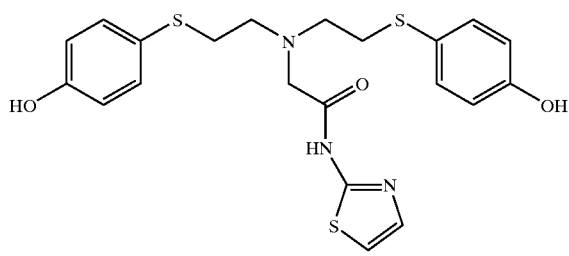
Compound No. 211
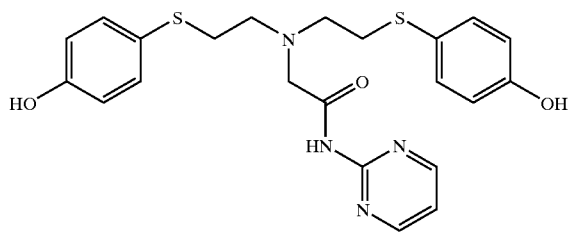
Compound No. 212
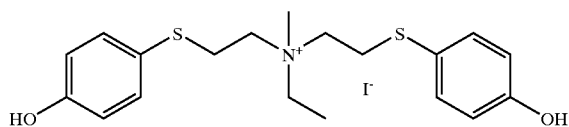
Compound No. 213
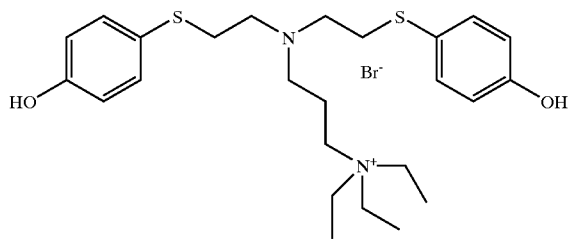
Compound No. 214

TABLE 3-continued
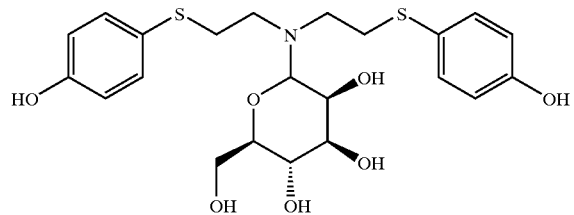
Compound No. 215
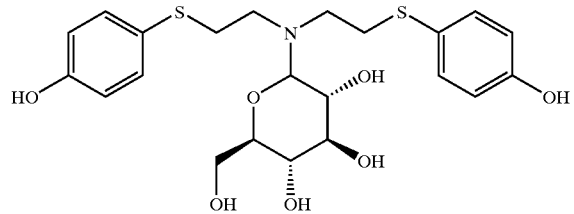
Compound No. 216
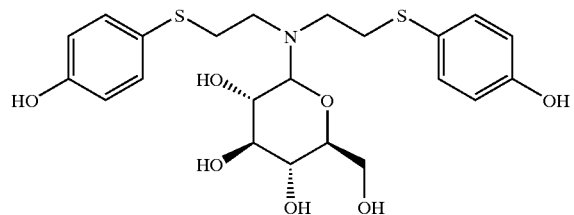
Compound No. 217
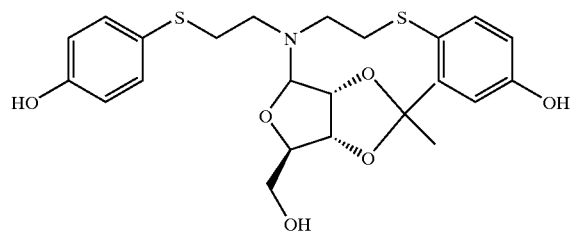
Compound No. 218
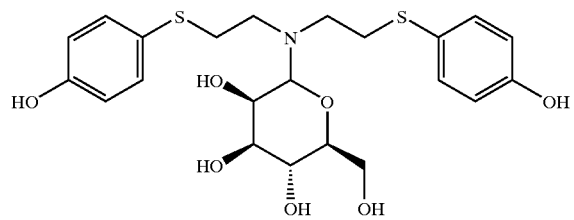
Compound No. 219
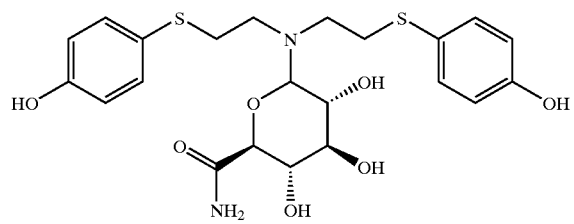
Compound No. 220

TABLE 3-continued
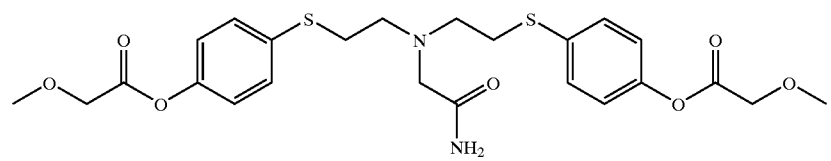
Compound No. 221
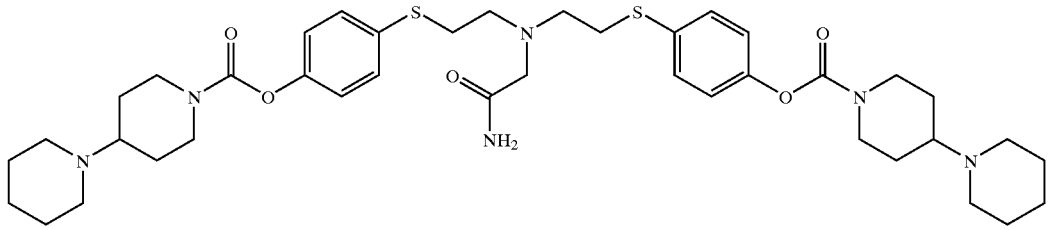
Compound No. 222
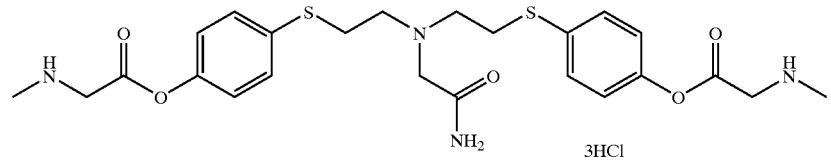
3HCl
Compound No. 223
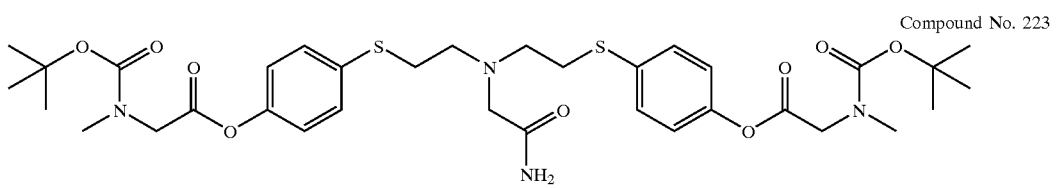
Compound No. 224
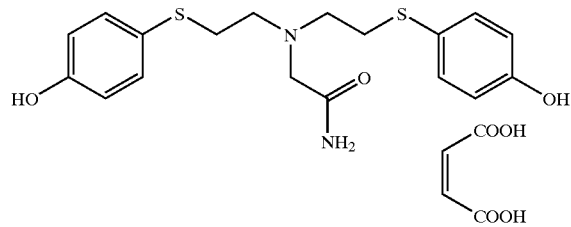
Compound No. 225
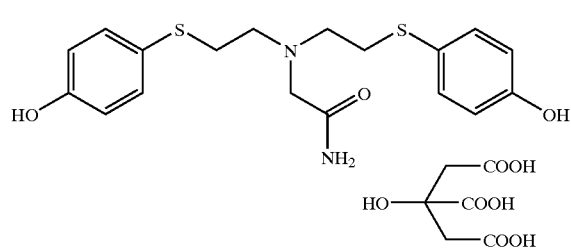
Compound No. 226
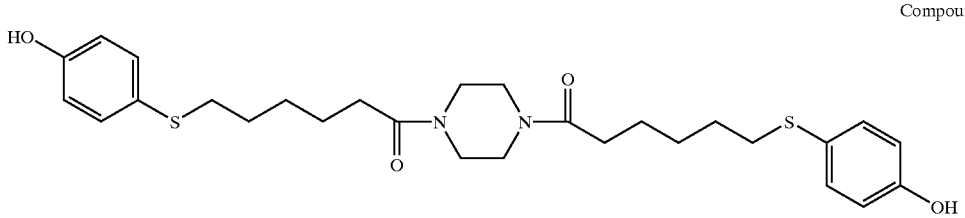
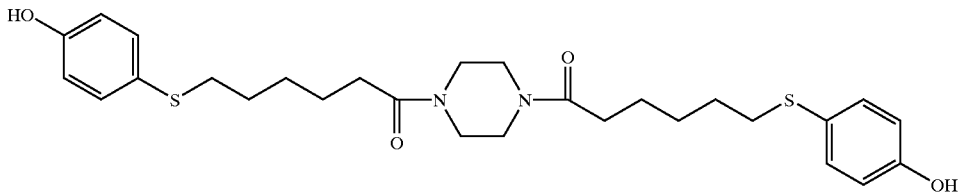
Compound No. 227

TABLE 3-continued

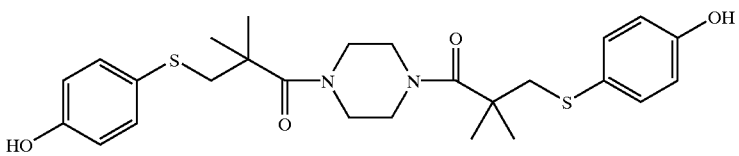

Compound No. 228

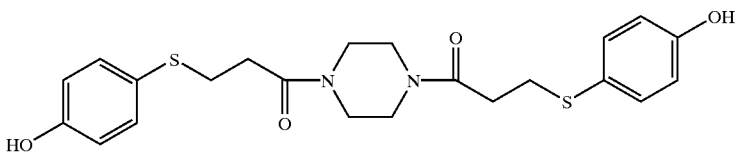

According to the present invention, there are provided novel compounds represented by the general formula (XII):

$$Ar^{23}-S-R^{22}-N(R^{24})-R^{23}-S-Ar^{24}.$$

$Ar^{23}$ and $Ar^{24}$ in the general formula (XII) have the same meanings as the aforementioned $Ar^1$ and $Ar^2$. However, those wherein each of $Ar^{23}$ and $Ar^{24}$ is a phenyl group having one hydroxyl group on the ring, and both of these phenyl groups have a tertiary alkyl group at a position on the ring adjacent to the hydroxyl group are excluded from the scope of the invention concerning the novel compounds of the present invention. $R^{22}$, $R^{23}$ and $R^{24}$ in the general formula (XII) have the same meanings as the aforementioned $R^2$, $R^3$, and $R^4$, provided that, when $R^{22}$ and $R^{23}$ do not form a ring. $R^{22}-N(R^{24})-R^{23}$ except for the part of $R^{24}$ does not contain an amide bond. Furthermore, in the above definitions, $R^{125}$, $R^{126}$, $R^{127}$, $R^{101A}$, $R^{101B}$, $R^{101C}$, and $R^{101D}$ have the same meanings as $R^{25}$, $R^{26}$, $R^{27}$, $R^{1A}$, $R^{1B}$, $R^{1C}$ and $R^{1D}$, respectively.

Examples of the divalent group suitable as $R^{22}$, $R^{23}$, or $R^{22}-N(R^{24})-R^{23}$ will be exemplified below. However, the divalent group which can be used for the compound of the present invention is not limited to these examples.

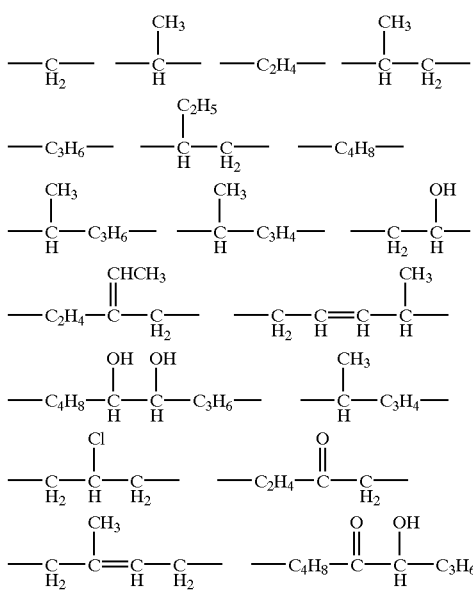

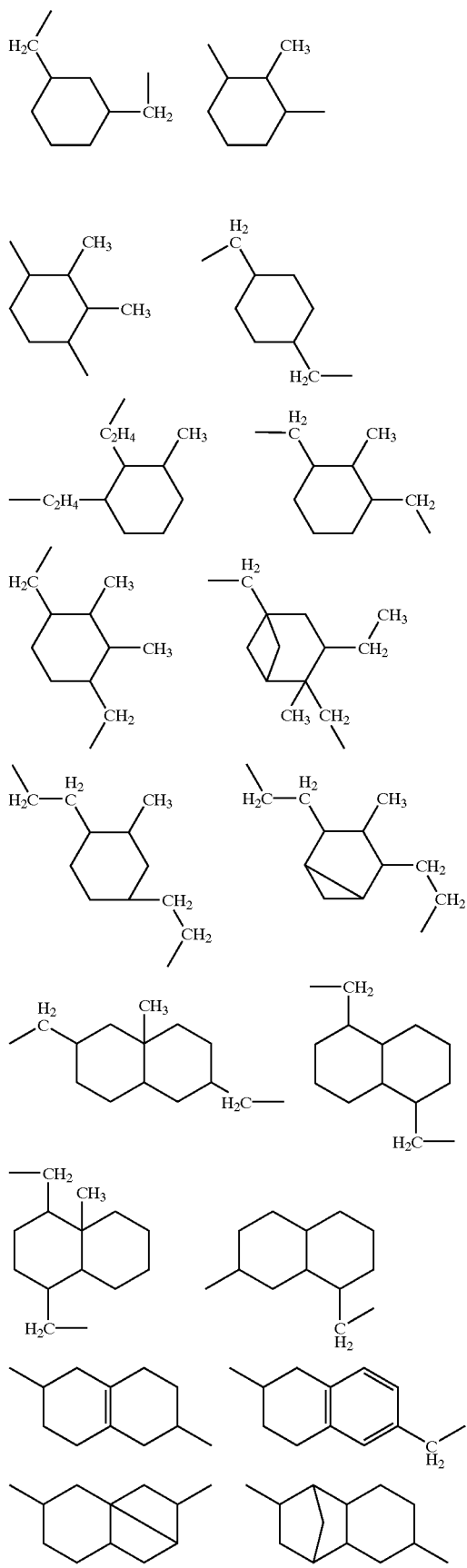
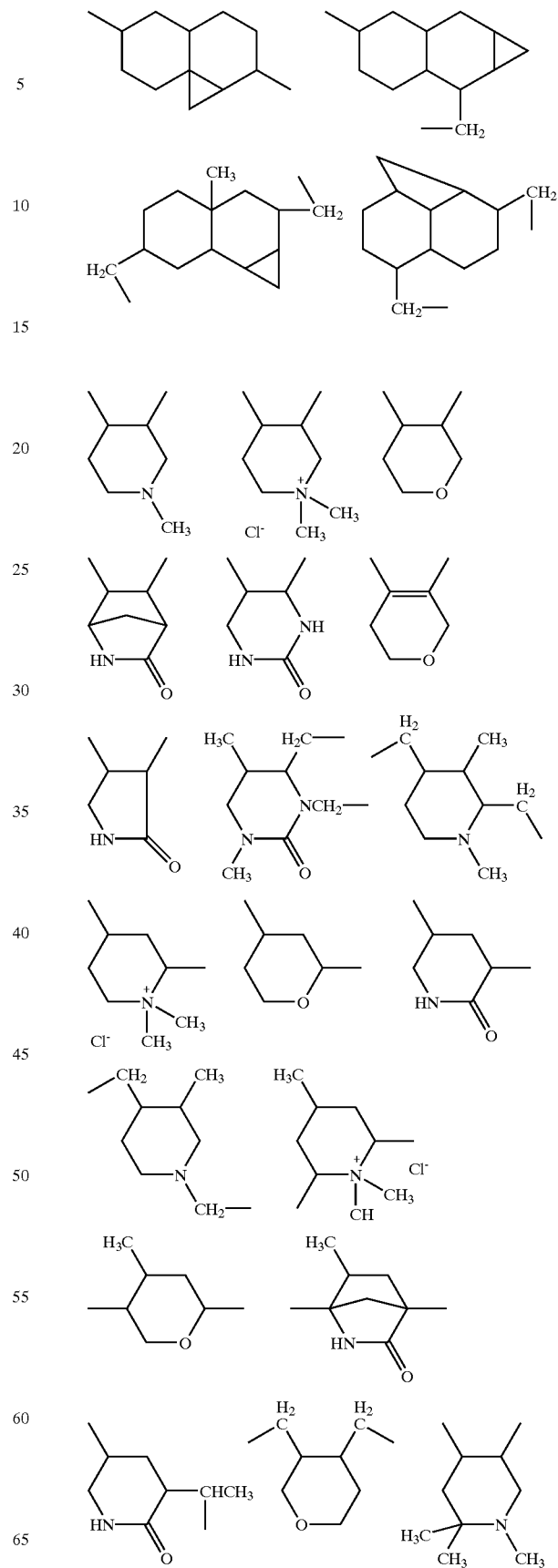

-continued
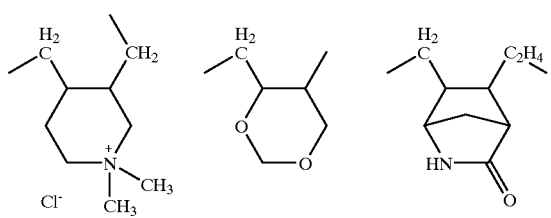
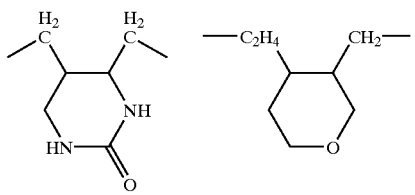
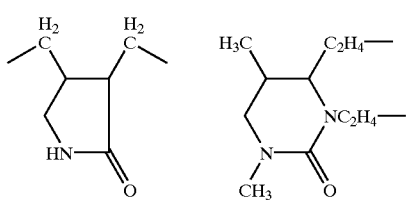
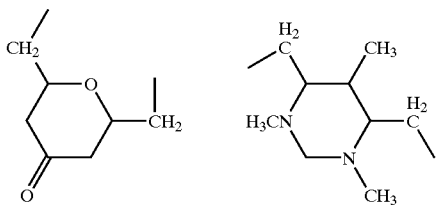
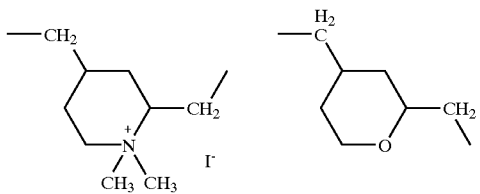
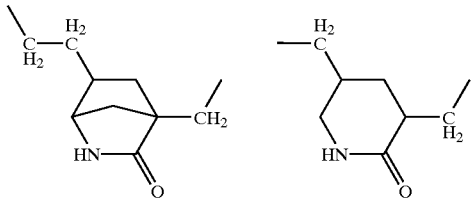
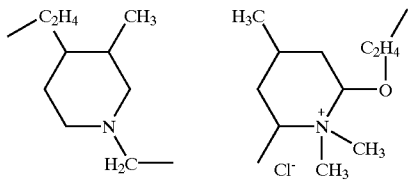
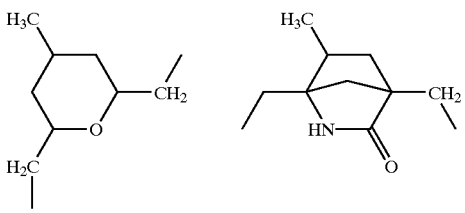
-continued
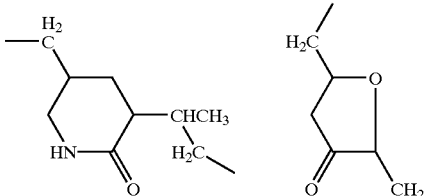
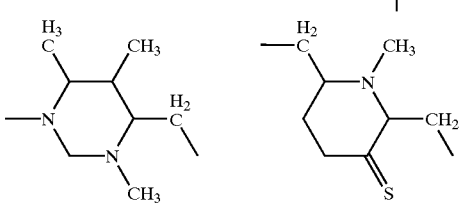
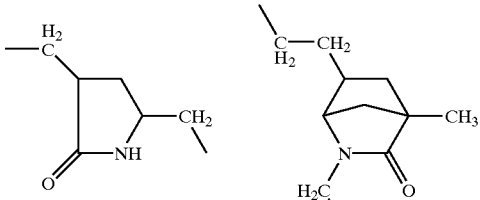
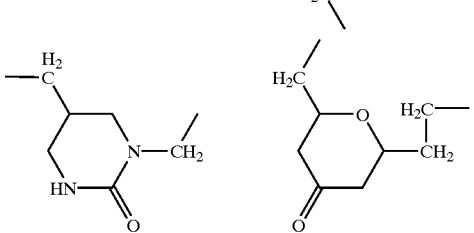
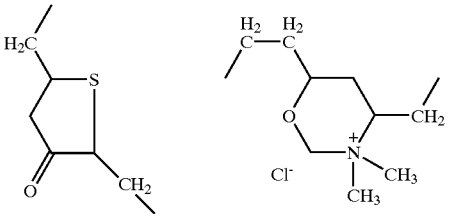
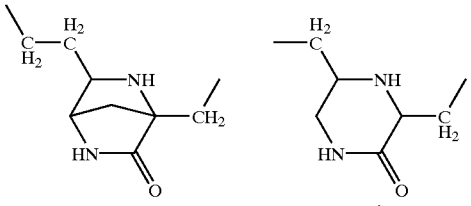
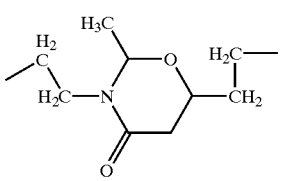
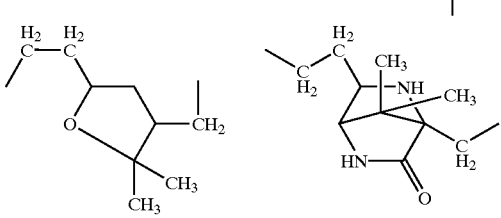

-continued
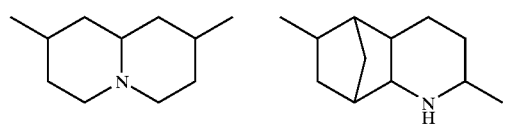
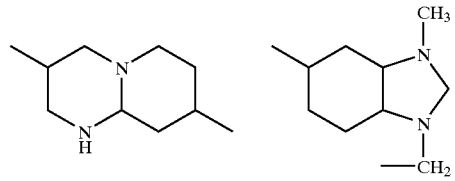
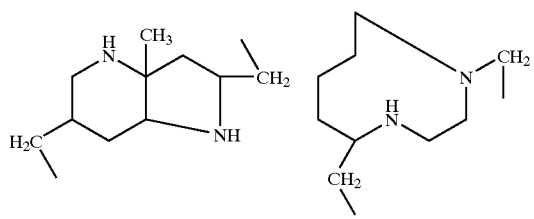
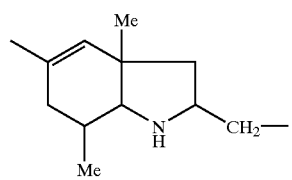
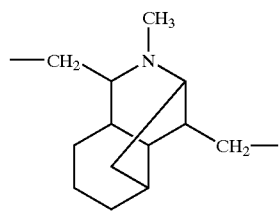
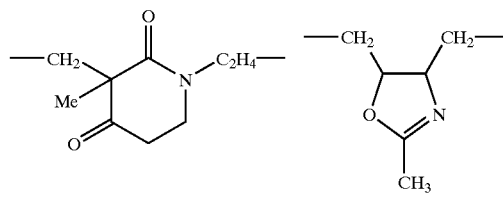
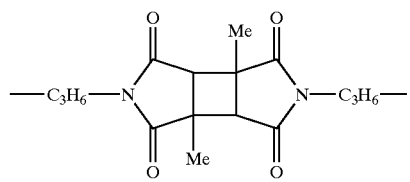
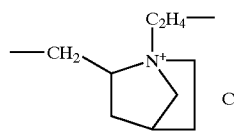
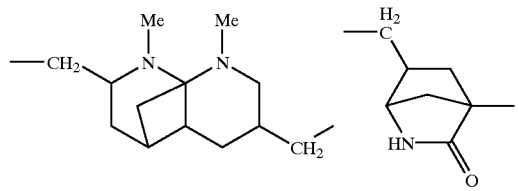
-continued
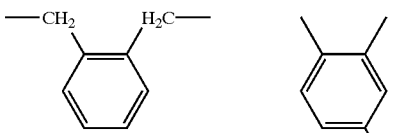
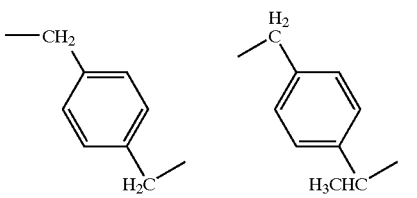
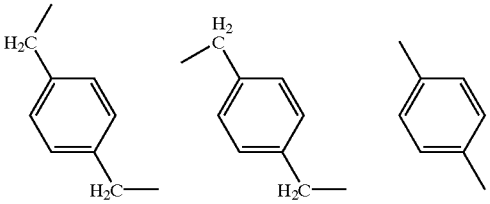
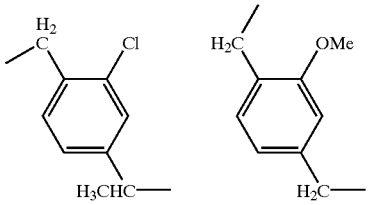
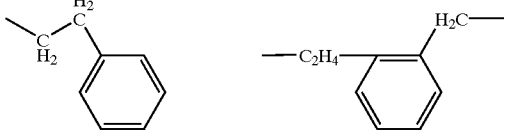
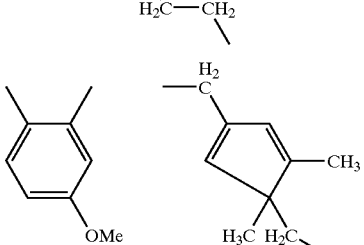
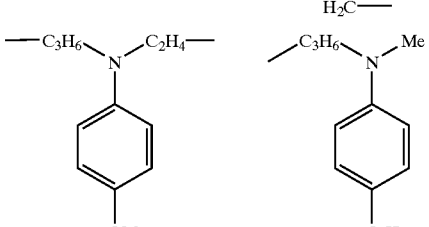
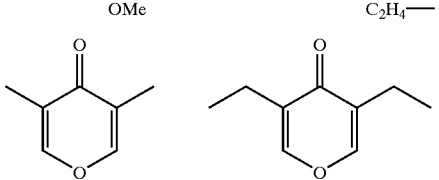

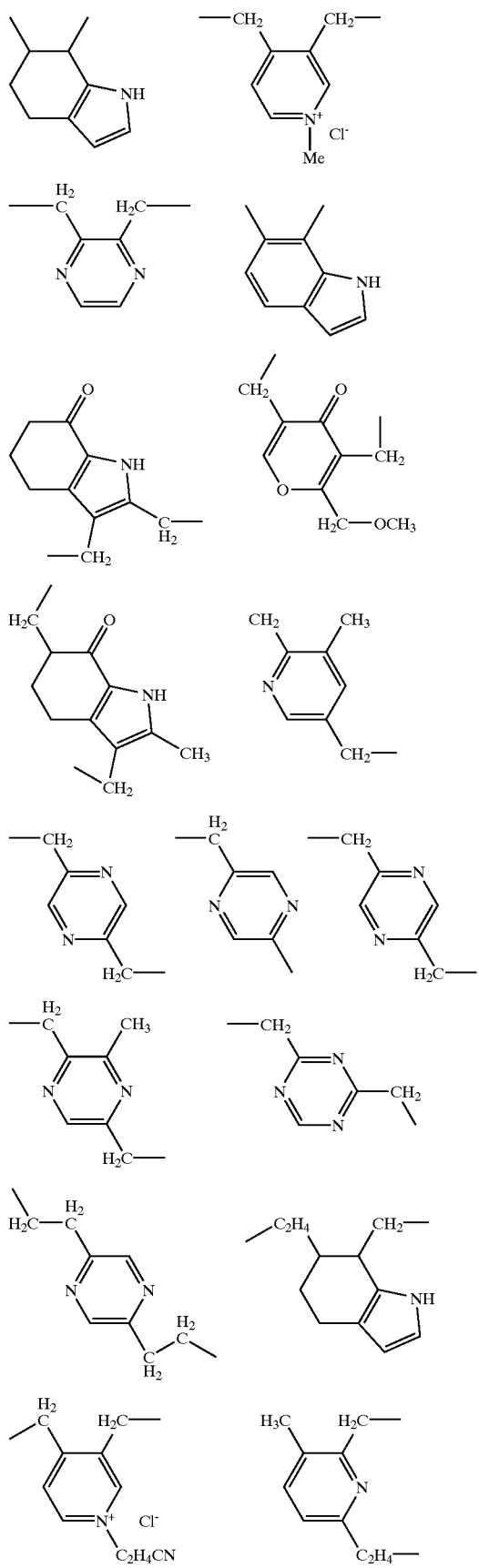

-continued

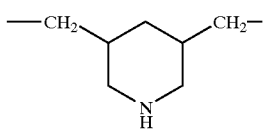
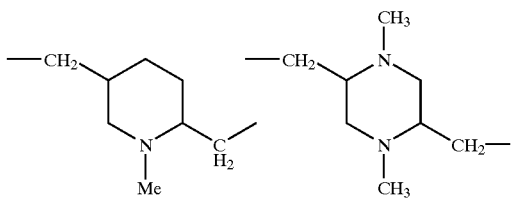
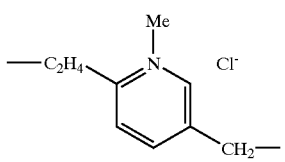
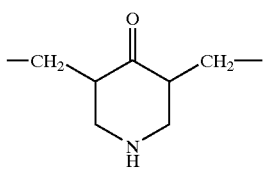

-continued

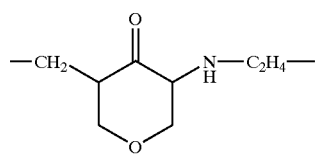
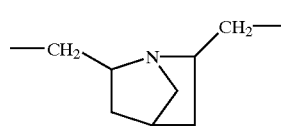

Particularly preferred compounds of the present invention represented by the formula (XII) will be specifically exemplified below. However, the compounds of the present invention are not limited to the following exemplary compounds.

TABLE 4

| Compound No. | $Ar^{23}$ | $R^{22}$ | $R^{23}$ | $R^{24}$ | $Ar^{24}$ |
|---|---|---|---|---|---|
| 45 | p-HO—Ph— | —$C_2H_4$— | —$C_2H_4$— | —H | p-HO—Ph— |
| 46 | p-HO—Ph— | —$C_3H_6$— | —$C_3H_6$— | —H | p-HO—Ph— |
| 47 | p-HO—Ph— | —$C_4H_8$— | —$C_4H_8$— | —H | p-HO—Ph— |
| 48 | p-HO—Ph— | —$C_2H_4$— | —$C_2H_4$— | —OH | p-HO—Ph— |
| 49 | p-HO—Ph— | —$C_2H_4$— | —$C_2H_4$— | —C(=NH)$NH_2$ | p-HO—Ph— |
| 50 | p-HO—Ph— | —$C_2H_4$— | —$C_2H_4$— | —CO$C_3H_7$ | p-HO—Ph— |
| 51 | p-HO—Ph— | —$C_2H_4$— | —$C_2H_4$— | —CO$CH_2$$CH_2$$CO_2$H | p-HO—Ph— |
| 52 | p-HO—Ph— | —$C_2H_4$— | —$C_2H_4$— | —CO$CH_2$$CH_2$S—Ph—OH-p | p-HO—Ph— |
| 53 | p-HO—Ph— | —$C_2H_4$— | —$C_2H_4$— | —CHO | p-HO—Ph— |
| 54 | p-HO—Ph— | —$C_2H_4$— | —$C_2H_4$— | —CO$CH_3$ | p-HO—Ph— |
| 55 | p-HO—Ph— | —$C_3H_6$— | —$C_3H_6$— | —CHO | p-HO—Ph— |
| 56 | p-HO—Ph— | —$C_3H_6$— | —$C_3H_6$— | —CO$CH_2$Cl | p-HO—Ph— |
| 59 | p-HO—Ph— | —$C_2H_4$— | —$C_2H_4$— | —$CH_2$$CH_2$$NH_2$ | p-HO—Ph— |
| 71 | p-HO—Ph— | —$C_2H_4$— | —$C_2H_4$— | —$C_2H_5$ | p-HO—Ph— |
| 72 | p-HO—Ph— | —$C_2H_4$— | —$C_2H_4$— | —$C_3H_7$ | p-HO—Ph— |
| 73 | p-HO—Ph— | —$C_2H_4$— | —$C_2H_4$— | —$CH_2$—C≡CH | p-HO—Ph— |
| 74 | p-HO—Ph— | —$C_2H_4$— | —$C_2H_4$— | —$CH_2$—CH=$CH_2$ | p-HO—Ph— |
| 75 | p-HO—Ph— | —$C_2H_4$— | —$C_2H_4$— | —$CH_2$-cyclopropyl | p-HO—Ph— |
| 76 | p-HO—Ph— | —$C_2H_4$— | —$C_2H_4$— | —$CH_2$—$SO_2$$NH_2$ | p-HO—Ph— |
| 77 | p-HO—Ph— | —$C_2H_4$— | —$C_2H_4$— | —$CH_2$—CN | p-HO—Ph— |
| 78 | p-HO—Ph— | —$C_2H_4$— | —$C_2H_4$— | —$C_2H_4$—CO—$NH_2$ | p-HO—Ph— |
| 79 | p-HO—Ph— | —$C_2H_4$— | —$C_2H_4$— | —$C_2H_4$—CO—N($CH_3$)$_2$ | p-HO—Ph— |
| 80 | p-HO—Ph— | —$C_2H_4$— | —$C_2H_4$— | —$C_2H_4$—CO—N($C_2H_5$)$_2$ | p-HO—Ph— |
| 81 | p-HO—Ph— | —$C_2H_4$— | —$C_2H_4$— | —$CH_2$—CO—$CH_3$ | p-HO—Ph— |
| 82 | p-HO—Ph— | —$C_2H_4$— | —$C_2H_4$— | —$C_2H_4$—NH—CO—$NH_2$ | p-HO—Ph— |
| 83 | p-HO—Ph— | —$C_2H_4$— | —$C_2H_4$— | —$C_2H_4$—NH—CO—$CH_3$ | p-HO—Ph— |
| 84 | p-HO—Ph— | —$C_2H_4$— | —$C_2H_4$— | —$CH_2$F | p-HO—Ph— |
| 85 | p-HO—Ph— | —$C_2H_4$— | —$C_2H_4$— | —$CF_3$ | p-HO—Ph— |
| 86 | p-HO—Ph— | —$C_2H_4$— | —$C_2H_4$— | —$C_2H_4$-(N-succinimido) | p-HO—Ph— |
| 87 | p-HO—Ph— | —$C_2H_4$— | —$C_2H_4$— | —$C_2H_4$—S—$CH_3$ | p-HO—Ph— |
| 88 | p-HO—Ph— | —$C_2H_4$— | —$C_2H_4$— | —$CH_2$-ethyleneacetal | p-HO—Ph— |
| 89 | p-HO—Ph— | —$C_2H_4$— | —$C_2H_4$— | —$CH_2$-(2-thienyl) | p-HO—Ph— |
| 90 | p-HO—Ph— | —$C_2H_4$— | —$C_2H_4$— | -furfuryl | p-HO—Ph— |
| 91 | p-HO—Ph— | —$C_2H_4$— | —$C_2H_4$— | —$CH_2$-(4-pyridyl) | p-HO—Ph— |
| 92 | p-HO—Ph— | —$C_2H_4$— | —$C_2H_4$— | -o-hydroxybenzyl | p-HO—Ph— |
| 93 | p-HO—Ph— | —$C_2H_4$— | —$C_2H_4$— | -m-hydroxybenzyl | p-HO—Ph— |
| 94 | p-HO—Ph— | —$C_2H_4$— | —$C_2H_4$— | -p-hydroxybenzyl | p-HO—Ph— |
| 95 | p-HO—Ph— | —$C_2H_4$— | —$C_2H_4$— | —($CH_2$)$_3$—OH | p-HO—Ph— |
| 96 | p-HO—Ph— | —$C_2H_4$— | —$C_2H_4$— | —$CH_2$—NH—CO—$CH_3$ | p-HO—Ph— |

TABLE 4-continued

| Compound No. | $Ar^{23}$ | $R^{22}$ | $R^{23}$ | $R^{24}$ | $Ar^{24}$ |
|---|---|---|---|---|---|
| 97 | p-HO—Ph— | —$C_2H_4$— | —$C_2H_4$— | —$CH_2$—CO—$NH_2$ | p-HO—Ph— |
| 98 | p-HO—Ph— | —$C_2H_4$— | —$C_2H_4$— | -benzyl | p-HO—Ph— |
| 99 | p-HO—Ph— | —$C_2H_4$— | —$C_2H_4$— | —$CH_2$-(3-pyridyl) | p-HO—Ph— |
| 100 | p-HO—Ph— | —$C_2H_4$— | —$C_2H_4$— | —$CH_2$-(2-pyridyl) | p-HO—Ph— |
| 101 | p-HO—Ph— | —$C_2H_4$— | —$C_2H_4$— | —$CH_2$-(2-quinolinyl) | p-HO—Ph— |
| 102 | p-HO—Ph— | —$C_2H_4$— | —$C_2H_4$— | —$C_2H_4$—OH | p-HO—Ph— |
| 103 | p-HO—Ph— | —$C_2H_4$— | —$C_2H_4$— | —$(CH_2)_3$—$OCH_3$ | p-HO—Ph— |
| 104 | p-HO—Ph— | —$C_2H_4$— | —$C_2H_4$— | —$C_2H_4$—$OCH_3$ | p-HO—Ph— |
| 105 | p-HO—Ph— | —$C_2H_4$— | —$C_2H_4$— | -o-fluorobenzyl | p-HO—Ph— |
| 106 | p-HO—Ph— | —$C_2H_4$— | —$C_2H_4$— | -p-fluorobenzyl | p-HO—Ph— |
| 107 | p-HO—Ph— | —$C_2H_4$— | —$C_2H_4$— | —$C_2H_4$—CO—(N-morpholino) | p-HO—Ph— |
| 108 | p-HO—Ph— | —$C_2H_4$— | —$C_2H_4$— | —$C_2H_4$—CO-(1-piperidyl) | p-HO—Ph— |
| 109 | p-HO—Ph— | —$C_2H_4$— | —$C_2H_4$— | —$C_2H_4$—$N(C_2H_5)_2$ | p-HO—Ph— |
| 110 | p-HO—Ph— | —$C_2H_4$— | —$C_2H_4$— | —$C_2H_4$—(N-morpholino) | p-HO—Ph— |
| 111 | p-HO—Ph— | —$C_2H_4$— | —$C_2H_4$— | —$C_2H_4$-(1-piperidyl) | p-HO—Ph— |
| 112 | p-HO—Ph— | —$C_2H_4$— | —$C_2H_4$— | —CO—$CH_3$ | p-HO—Ph— |
| 113 | p-HO—Ph— | —$C_2H_4$— | —$C_2H_4$— | —CO—$C_2H_5$ | p-HO—Ph— |
| 114 | p-HO—Ph— | —$C_2H_4$— | —$C_2H_4$— | —CO—$C_6H_5$ | p-HO—Ph— |
| 115 | p-HO—Ph— | —$C_2H_4$— | —$C_2H_4$— | —CO-(2-pyridyl) | p-HO—Ph— |
| 116 | p-HO—Ph— | —$C_2H_4$— | —$C_2H_4$— | —CO-(3-pyridyl) | p-HO—Ph— |
| 117 | p-HO—Ph— | —$C_2H_4$— | —$C_2H_4$— | —CO-(4-pyridyl) | p-HO—Ph— |
| 118 | p-HO—Ph— | —$C_2H_4$— | —$C_2H_4$— | —$SO_2$—$CH_3$ | p-HO—Ph— |
| 119 | p-HO—Ph— | —$C_2H_4$— | —$C_2H_4$— | —$SO_2$—$C_6H_5$ | p-HO—Ph— |
| 120 | p-HO—Ph— | —$C_2H_4$— | —$C_2H_4$— | —CO—$NH_2$ | p-HO—Ph— |
| 121 | p-HO—Ph— | —$C_2H_4$— | —$C_2H_4$— | —CO—$NH(CH_3)$ | p-HO—Ph— |
| 122 | p-HO—Ph— | —$C_2H_4$— | —$C_2H_4$— | —CO—$N(CH_3)_2$ | p-HO—Ph— |
| 123 | p-HO—Ph— | —$C_2H_4$— | —$C_2H_4$— | —CO—$N(C_2H_5)_2$ | p-HO—Ph— |
| 124 | p-HO—Ph— | —$C_2H_4$— | —$C_2H_4$— | —CO-(N-morpholino) | p-HO—Ph— |
| 125 | p-HO—Ph— | —$C_2H_4$— | —$C_2H_4$— | —CO-(1-piperidyl) | p-HO—Ph— |
| 126 | p-HO—Ph— | —$C_2H_4$— | —$C_2H_4$— | —CO—NH—$C_6H_5$ | p-HO—Ph— |
| 127 | p-HO—Ph— | —$C_2H_4$— | —$C_2H_4$— | —CO—NH-(2-pyridyl) | p-HO—Ph— |
| 128 | p-HO—Ph— | —$C_2H_4$— | —$C_2H_4$— | —$SO_2$—$NH_2$ | p-HO—Ph— |
| 129 | p-HO—Ph— | —$C_2H_4$— | —$C_2H_4$— | —$SO_2$—$N(C_2H_5)_2$ | p-HO—Ph— |
| 130 | p-HO—Ph— | —$C_2H_4$— | —$C_2H_4$— | —$SO_2$-(N-morpholino) | p-HO—Ph— |

Compound No. 57

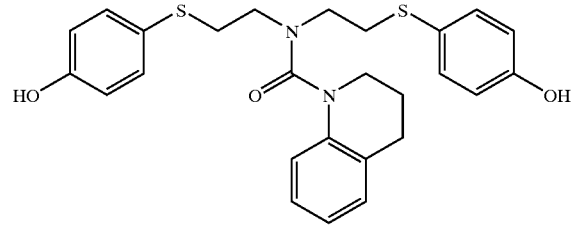

Compound No. 58

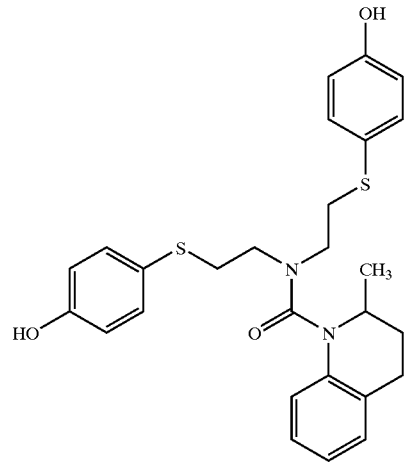

Compound No. 191

TABLE 4-continued
| Compound No. | Ar²³ | R²² | R²³ | R²⁴ | Ar²⁴ |
|---|---|---|---|---|---|
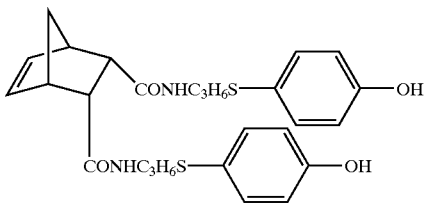
Compound No. 192
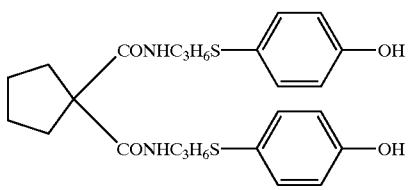
Compound No. 193
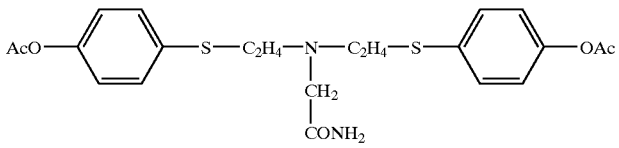
Compound No. 194
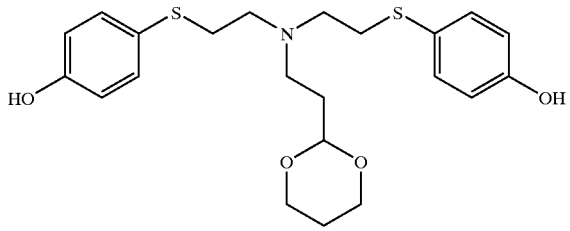
Compound No. 195
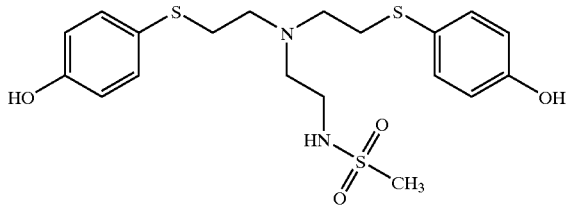
Compound No. 196
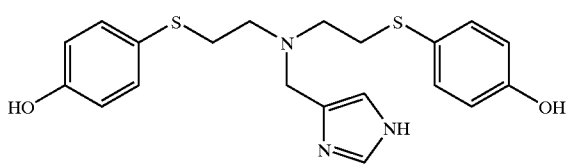
Compound No. 197

TABLE 4-continued
| Compound No. | Ar²³ | R²² | R²³ | R²⁴ | Ar²⁴ |
|---|---|---|---|---|---|
Compound No. 198
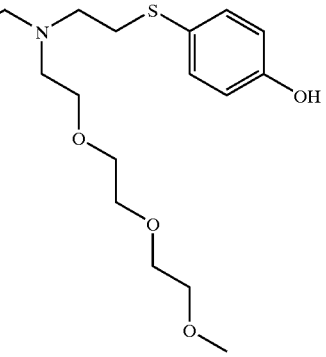
Compound No. 199
Compound No. 200
Compound No. 201
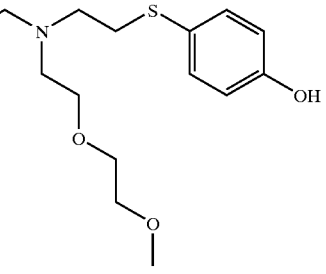
Compound No. 202

TABLE 4-continued
| Compound No. | Ar²³ | R²² | R²³ | R²⁴ | Ar²⁴ |
|---|---|---|---|---|---|
| | 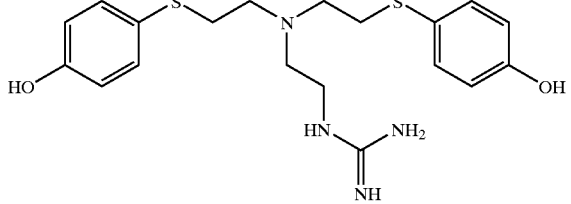 | | | | |
| Compound No. 203 | 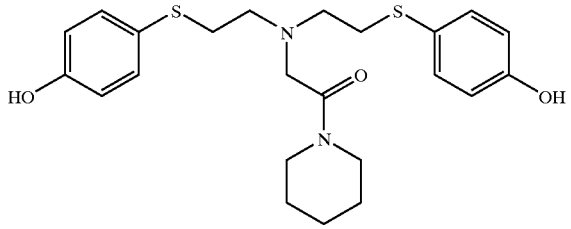 | | | | |
| Compound No. 204 | 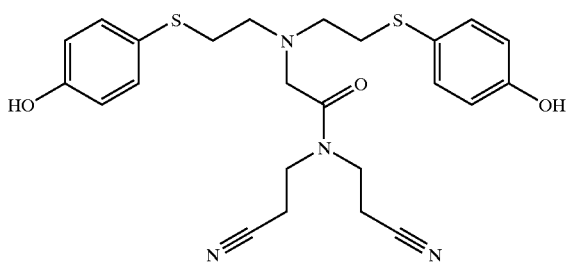 | | | | |
| Compound No. 205 | 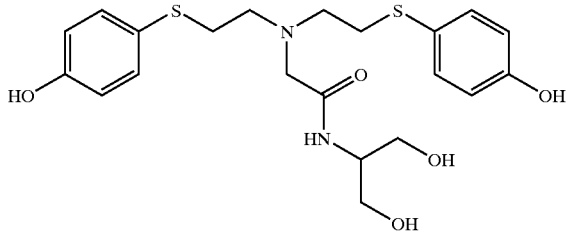 | | | | |
| Compound No. 206 | 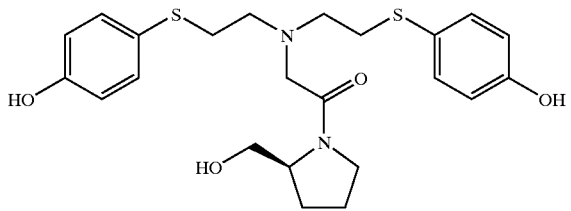 | | | | |
| Compound No. 207 | 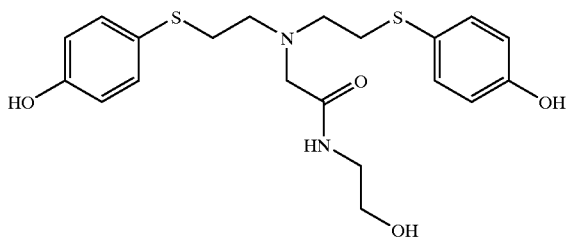 | | | | |

TABLE 4-continued
| Compound No. | Ar²³ | R²² | R²³ | R²⁴ | Ar²⁴ |
|---|---|---|---|---|---|
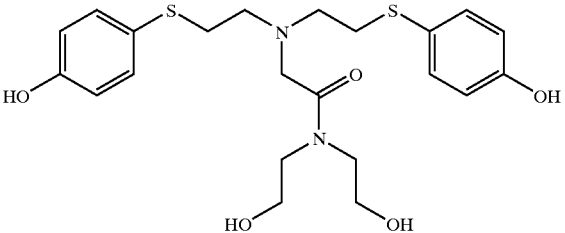
Compound No. 208
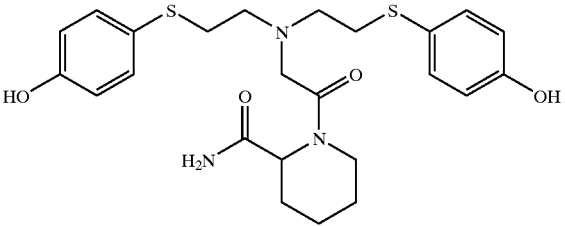
Compound No. 209
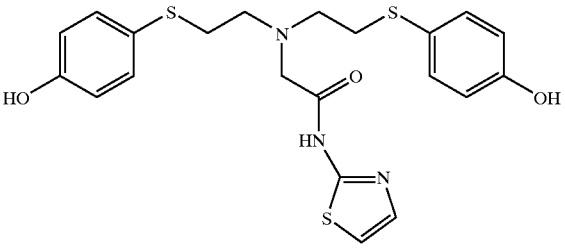
Compound No. 210
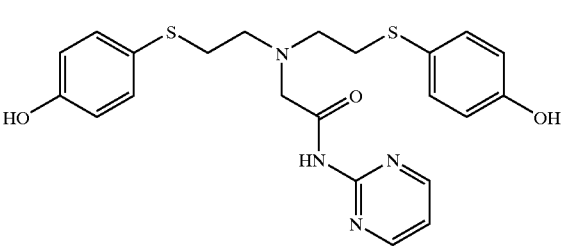
Compound No. 211
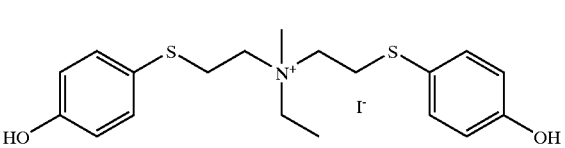
Compound No. 212
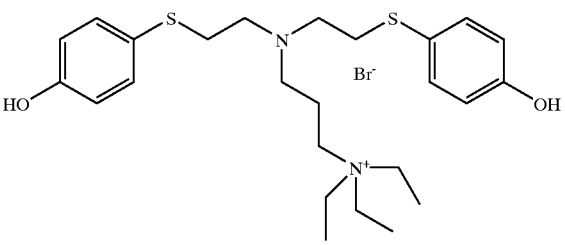
Compound No. 213
Compound No. 214

TABLE 4-continued
| Compound No. | Ar²³ | R²² | R²³ | R²⁴ | Ar²⁴ |
|---|---|---|---|---|---|
| Compound No. 215 |  | | | | |
| Compound No. 216 |  | | | | |
| Compound No. 217 |  | | | | |
| Compound No. 218 | 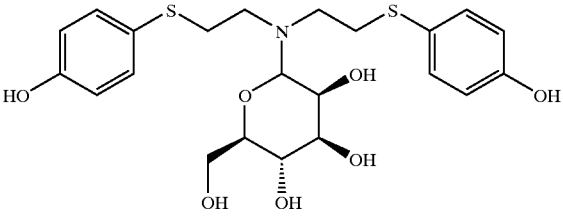 | | | | |
| Compound No. 219 | 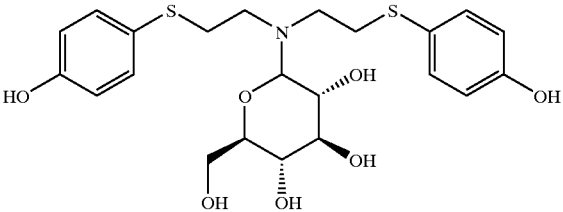 | | | | |
| Compound No. 220 | 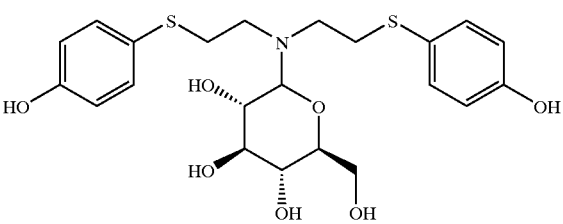 | | | | |

TABLE 4-continued

| Compound No. | Ar²³ | R²² | R²³ | R²⁴ | Ar²⁴ |
|---|---|---|---|---|---|

Compound No. 221

Compound No. 222

Compound No. 223

3HCl

Compound No. 224

Compound No. 225

Compound No. 226

TABLE 4-continued

| Compound No. | Ar²³ | R²² | R²³ | R²⁴ | Ar²⁴ |
|---|---|---|---|---|---|

Compound No. 227

Compound No. 228

The compounds of the present invention may form an acid addition salt, and may also form a base addition salt depending on the types of substituents. Examples of the acid addition salt include, but not limited thereto, mineral acid salts such as hydrochlorides, sulfates and nitrates, and organic acid salts such as p-toluenesulfonates, methanesulfonates, acetates, chloroacetates, oxalates, trifluoromethanesulfonates, and quinolinesulfonates. When they form a base addition salt, metal salts such as sodium salts and potassium salts, ammonium salts such as ammonium salts and triethylammonium salts and the like may be used. The compounds of the present invention may also form intramolecular zwitter ions based on a phenolic hydroxyl group and a basic group, which also fall within the scope of the present invention. Furthermore, the compounds of the aforementioned formula (XI) and formula (XII) in free form or any salts thereof, and any hydrates or any solvates of the compounds in free form or salts thereof fall within the scope of the present invention. Solvents that can form solvates are not particularly limited. For example, the solvate may be formed with methanol, ethanol, acetone, tetrahydrofuran, dichloromethane, chloroform, dimethylformamide or the like.

The compounds of the present invention may have one or more asymmetric carbons depending on the types of the substituents. Furthermore, a sulfur atom may also serve as an asymmetric center. Any optical isomers in optically pure form based on one or more asymmetric carbons, mixtures of the optical isomers, racemates, diastereomers based on two or more asymmetric carbons, mixtures of the diastereomers and the like all fall within the scope of the present invention.

Two or three groups selected from $R^{22}$, $R^{23}$, and $R^{24}$ may bind to each other, via a divalent group if required, to form a saturated or unsaturated cyclic structure. In that case, the nitrogen atom to which $R^{24}$ binds may be an atom that constitutes the ring. Examples of the ring include, for example, pyrrole ring, piperidine ring, indole ring, pyridine ring, triazine ring, pyrimidine ring, quinoline ring, oxazine ring, indazole ring, thiazole ring and the like. These rings may have a partially or completely reduced ring structure. Furthermore, those wherein one more monovalent group such as an alkyl group further binds to the nitrogen atom to which $R^{24}$ binds to form a quaternary salt also fall within the scope of the present invention. The counter ion of the quaternary salt may be, for example, iodide ion, bromide ion, chloride ion, perchlorate ion and the like. As the monovalent group, $C_{1-6}$ alkyl groups such as methyl group and the like are preferred.

The methods for preparing the bisaryl compounds represented by the aforementioned general formulas (I), (II) and (XII) are not particularly limited, and they can be synthesized via various synthetic routes. Methods for preparing typical compounds of the present invention are specifically disclosed in Examples set out below, and accordingly, those skilled in the art will readily prepare bisaryl compounds falling within the scopes of the aforementioned general formulas by referring to the method described in Examples, adding suitable alterations and modifications to the methods, if required, and suitably choosing starting materials and reagents. For the preparation, one step, or several combined steps selected from various condensation, addition, oxidation, and reduction reactions and the like can be used. These reactions are detailed in literature. For example, various methods mentioned as unit operations and starting materials disclosed in "Jikken Kagaku Koza" (Maruzen Co., Ltd., each separate volume of the first to the 4th edition are available) can be preferably used.

For example, it may be preferable to use a mercapto compound, an amine compound and the like for a starting material from viewpoints of a reaction operation and an yield. For example, unit operations such as synthesis of thioether (sulfide) and synthesis of ester; reactions of mercapto group with reactive functional groups such as vinyl group, halogen atoms (including haloalkyl groups), epoxy group, aziridine ring, acyl halide groups, and isocyanate group; and amination reaction, amidation reaction, alkylation reaction and the like are well known to those skilled in the art. Therefore, it is possible to chose suitable methods from the conventional methods considering an yield, easiness of reaction and the like.

For example, in these production methods, when any of the defined groups are changed under the condition of the reaction steps, or unsuitable to proceed the reaction steps, desired steps may be efficiently performed by using techniques commonly used in the synthetic organic chemistry, for example, protection and deprotection of functional groups, or treatments including oxidation, reduction, and hydrolysis. Isolation and purification of synthetic intermediates and target compounds in the aforementioned steps can be performed by common techniques in the field of synthetic organic chemistry, for example, filtration, extraction, washing, drying, concentration, recrystallization, various chromatography methods and the like. In addition, synthetic intermediates may be used in subsequent steps without isolation.

EXAMPLES

The present invention will be more specifically explained with reference to the following examples. However, the scope of the present invention is not limited to these examples. The compound numbers used in the examples correspond to the compound numbers shown in the aforementioned tables.

Example 1

Synthesis of Compound 45

Bis(2-chloroethyl)amine hydrochloride (17.8 g) and thiohydroquinone (25.2 g) were added to a 1,000 ml flask provided with a stirrer and a condenser, and methanol (300 ml) was added thereto for dissolution. To this solution, a 28% solution (57.9 g) of sodium methoxide in methanol was added dropwise at room temperature. After the addition was completed, the reaction mixture was stirred under reflux by heating for 3 hours, and then left standing for one day. The reaction mixture was transferred to a 3 liter-beaker, 1,500 ml of water was added, and the deposited product was separated. The crude product was recrystallized from methanol to obtain 20 g of the target compound (m.p. 133–134° C.).

$^1$H-NMR (DMSO-$d_6$) δ (ppm) 2.61 (t, 4H), 2.83 (t, 4H), 3.38 (s, 1H), 6.72 (dd, 4H), 7.20 (dd, 4H), 9.55 (s, 2H)

Example 2

Synthesis of Compound 113

In a 100 ml three-neck flask, Compound 45 (3.2 g) synthesized in Example 1 was dissolved in dimethylacetamide (15 ml), and propionic anhydride (1.4 ml) was dropwise added thereto under ice cooling. The reaction mixture was stirred for 1 hour at room temperature, poured into diluted hydrochloric acid, and extracted with ethyl acetate. The organic layer was washed with saturated brine, dried over magnesium sulfate, and concentrated under reduced pressure. The resulting residue was purified by silica gel column chromatography (ethyl acetate/hexane=7/3-1/1) to obtain 3.58 g of the target compound.

$^1$H-NMR (DMSO-$d_6$) δ (ppm) 0.37 (t, 3H), 2.04 (q, 2H), 2.90 (m, 4H), 3.30 (m, 4H), 6.76 (d, 4H), 7.20 (d, 4H), 9.57 (s, 1H), 9.60 (s, 1H)

Example 3

Synthesis of Compound 61

3-Bromopropylamine hydrobromide (50.0 g) and methylene chloride (300 ml) were put into a 1,000 ml flask provided with a stirrer and a condenser, and triethylamine (46 g) was added thereto at a temperature below 10° C. Then, bromoacetyl chloride (36 g) was added dropwise to the mixture while keeping the temperature of the reaction mixture at 20° C. or below 20° C., and then the mixture was stirred for 1 hour. The organic layer was separated by filtration and concentrated, and the residue was purified by silica gel column chromatography (developing solvent: hexane/ethyl acetate=2:1) to obtain (3-bromopropyl)-1-bromoacetamide (yield: 24%). Thiohydroquinone (5.0 g) and (3-bromopropyl)-1-bromoacetamide (5.8 g) were added to methanol (50 ml), and 28% sodium methoxide (7.6 g) was added thereto with stirring and the mixture was stirred at 40° C. for 2 hours. Water (200 ml) was added to the reaction mixture, the mixture was extracted with ethyl acetate, and the organic phase was dried. The product obtained after evaporation of the solvent was treated with acetonitrile to obtain crystals (m.p. 122–124° C.).

Example 4

Synthesis of Compound 1

2,6-Dichloromethylpyridine (3.5 g), and thiohydroquinone (5.0 g) were put into a 100 ml flask provided with a stirrer and a condenser, and methanol (20 ml) and a 28% solution (7.7 g) of sodium methoxide in methanol were added thereto at room temperature. The mixture was warmed to 60° C., and stirred for 1 hour at the same temperature. After the methanol was evaporated, the organic phase was extracted with ethyl acetate. The organic phase was dried and concentrated to obtain crystals of the target compound. The product was recrystallized from acetonitrile to obtain the target compound (yield: 70%, m.p. 140–140.5° C.).

Example 5

Synthesis of Compound 27

Methanol (40 ml) was put into a flask provided with a stirrer, thiohydroquinone (0.08 mol) and 48% aqueous NaOH (0.084 mol) were added thereto, and then bis-2-chloroethyl ether (0.04 mol) was dropwise added thereto with stirring at room temperature. The mixture was maintained at 40° C. for 4 hours, then added to water (300 ml) and extracted with ethyl acetate. The organic phase was washed with water and dried, and the solvent was evaporated to obtain crude crystals of the target compound. The crystals were recrystallized from benzene to obtain the target compound (yield: 82%, m.p. 91–92° C.).

Example 6

Synthesis of Compound 162

β,β'-Dichlorodiethylformal was synthesized according to the method of Vinokurov D. M. The target compound was obtained in the same manner as in Example 5 except that the above-obtained compound was used as a halide starting material. The target compound was obtained through recrystallization from a mixed solvent of water and methanol (yield: 81%, m.p. 108–110° C.)

Example 7

Synthesis of Compound 124

Compound 45 (10.0 g) obtained in Example 1 was put into a 500 ml flask provided with a stirrer and a calcium chloride tube, and dimethylacetamide (100 ml) was added thereto for dissolution. To this solution was added triethylamine (7.78 ml) and 4-morpholinecarbonyl chloride (4.17 g), the mixture was stirred for 2 hours, then water was added thereto and the mixture was further made neutral with hydrochloric acid. The organic layer was extracted with ethyl acetate, washed with water (3 times) and with saturated brine (2 times), then dried and concentrated to obtain 8.30 g of Compound 124 (semi-solid).

$^1$H-NMR (DMSO-$d_6$) δ (ppm) 2.86 (t, 4H), 2.87 (t, 4H), 3.20 (t, 4H), 3.33 (t, 4H), 6.74(d, 4H), 7.23 (d, 4H), 9.61(s, 2H)

Example 8

Synthesis of Compound 97

Compound 45 (964 mg) obtained in Example 1 was put into a 20 ml flask provided with a calcium chloride tube, and dimethylformamide (5 ml) was added thereto for dissolution. To this solution was added sodium hydrogen carbonate (1 g), potassium iodide (166 mg) and chloroacetamide (300 mg), and the mixture was stirred at 80° C. for 2 hours. The reaction mixture was added to water, the mixture was extracted with ethyl acetate, and the organic layer was washed with water (3 times) and saturated brine (2 times), then dried and concentrated. The residue was purified by silica gel chromatography (eluent: methylene chloride/ethyl acetate=2I3), and the solvent was concentrated. The residue was crystallized by adding hexane, filtered, washed and dried to obtain 900 mg of Compound 97 (m.p. 105–106° C.).

$^1$H-NMR (CD$_3$OD) δ (ppm) 2.72 (t, 4H), 2.82 (t, 4H), 3.10 (s, 2H), 6.80 (d, 4H), 7.30 (d, 4H)

Example 9

Synthesis of Compound 190

2-Fluorophenol (4.05 g), water (50 ml), copper sulfate pentahydrate (18.0 g), and ammonium thiocyanate (11.0 g) were successively put into a 300 ml flask provided with a stirrer, and the mixture was stirred for 4 hours on a water bath (50° C.). The solid was removed by filtration, and the filtrate was extracted with ethyl acetate, then dried and concentrated. The residue was purified by silica gel chromatography (eluent: hexane/ethyl acetate=10/1.5) to obtain 1.61 g of 3-fluoro-4-hydroxybenzothiocyanate.

$^1$H-NMR (CDCl$_3$)δ (ppm) 5.79 (s, 1H), 7.07 (dd, 1H), 7.28 (dd, 1H), 7.36 (dd, 1H)

The resulting 3-fluoro-4-hydroxybenzothiocyanate (0.45 g) was put into a nitrogen-purged 50 ml flask provided with a stirrer, and dissolved in tetrahydrofuran (5.0 ml). The solution was cooled to 0° C., aluminium lithium hydride (0.10 g) was added thereto, and then the mixture was stirred at room temperature for 20 minutes. To the mixture was then added ethyl acetate and saturated aqueous ammonium chloride, and the mixture was neutralized with diluted hydrochloric acid. The organic layer was extracted with ethyl acetate, dried and concentrated. The residue was purified by silica gel chromatography (eluent: hexane/ethyl acetate=10/1.5) to obtain 0.13 g of 3-fluoro-4-hydroxythiophenol.

$^1$H-NMR (CDCl$_3$)δ (ppm) 3.42 (s, 1H), 5.52 (s, 1H), 6.88 (dd, 1H), 7.00 (dd, 1H), 7.08 (dd, 1H)

The 3-fluoro-4-hydroxythiophenol (0.13 g) obtained above was put into a 50 ml flask provided with a stirrer, and dissolved in methanol (5.0 ml). The solution was bubbled with nitrogen gas for about 15 minutes for deairing, sodium methoxide (28%, 0.20 ml) and bis(2-chloroethyl) ether (0.52 ml) were added thereto, and then the mixture was stirred for 2 hours (40° C.). The mixture was neutralized with diluted hydrochloric acid, and the organic layer was extracted with ethyl acetate, dried and concentrated. The residue was purified by silica gel chromatography (eluent: hexane/ethyl acetate=5/1) to obtain 56 mg of Compound 190 (m.p. 87–88° C.).

1H-NMR (CDCl$_3$) δ (ppm) 2.95 (t, 4H), 3.55 (t, 4H), 6.89 (dd, 1H), 7.03 (dd, 1H), 7.12 (dd, 1H)

Example 10

Synthesis of Compound 191

5-Norbornene-2-dicarboxylic acid anhydride (1.30 g), 2-(4-hydroxyphenylthio)propylamine (3.66 g), and triethylamine (2.02 g) were put into a 200 ml flask provided with a stirrer and a condenser, dimethylformamide (50 ml) was added thereto for dissolution, and then the solution was stirred at room temperature for 17 hours. To the reaction mixture was added water, and the mixture was extracted with ethyl acetate. The organic layer was washed with 1 N hydrochloric acid and then with saturated aqueous sodium hydrogen carbonate, dried over anhydrous sodium sulfate, and concentrated under reduced pressure. The residue was purified by silica gel chromatography (eluent: dichloromethane/ethyl acetate=2/8) to obtain 1.76 g of Compound 191 as a semi-solid substance.

$^1$H-NMR (DMSO-d$_6$) δ (ppm) 1.20 (s, 2H), 1.51 (t, 4H), 2.72 (t, 4H), 2.90 (s, 2H), 2.98 (q, 4H), 3.03 (s, 2H), 6.07 (s, 2H), 6.72 (d, 4H), 7.34 (d, 2H), 9.56 (s, 2H)

Example 11

Synthesis of Compound 192

1-Cyclopentane diacetic acid (0.93 g) was put into a 100 ml flask provided with a stirrer and a condenser and tetrahydrofuran (35 ml) was added thereto for dissolution. Then, to the solution was added dicyclohexylcarbodiimide (2.06 g) and 2-(4-hydroxyphenylthio)propylamine (1.83 g), and the mixture was stirred at 40° C. for 6 hours. Insoluble materials were removed from the reaction mixture by suction filtration, and the filtrate was concentrated under reduced pressure. The residue was purified by silica gel chromatography (eluent: hexane/ethyl acetate=1/1) to obtain 1.09 g of Compound 192 as a semi-solid substance.

$^1$H-NMR (DMSO-d$_6$) δ (ppm) 1.18 (t, 2H), 1.58 (m, 4H), 2.13 (s, 2H), 2.76 (t, 2H), 3.14 (dd, 2H), 6.72 (d, 2H), 7.20 (d, 2H), 8.08 (t, 1H), 9.55 (s, 1H)

Example 12

Synthesis of Compound 100

Compound 45 (1.79 g) obtained in Example 1 was put into a 50 ml flask provided with a calcium chloride tube and dimethylformamide (15 ml) was added thereto for dissolution. To this solution was added sodium hydrogen carbonate (1.68 g) and 2-chloromethylpyridine hydrochloride (820 mg), and the mixture was stirred at 70° C. for 4 hours. The reaction mixture was added to water and the mixture was extracted with ethyl acetate. The extract was washed with water (3 times) and saturated brine (2 times), dried, and then concentrated. The residue was purified by silica gel chromatography (eluent: methylene chloride/methanol=20/1), the solvent was concentrated, and the residue was crystallized by adding hexane, and then filtered to obtain 1.57 g of Compound 100 (m.p. 80–81° C.).

1H-NMR (DMSO-d$_6$) δ (ppm) 2.60 (t, 4H), 2.85 (t, 4H), 3.68 (s, 2H), 6.68 (d, 4H), 7.15 (d, 4H), 7.25 (t, 1H), 7.41 (d, 1H), 7.70 (t, 1H), 8.42 (d, 1H), 9.55 (s, 2H)

Example 13

Synthesis of Compound 193

Compound 97 (1.00 g) obtained in Example 8 was put into a 100 ml flask provided with a calcium chloride tube at room temperature, and acetonitrile (10 ml) was added thereto for dissolution. To this solution was added pyridine (2.1 ml) and acetic anhydride (0.75 ml), and the mixture was stirred at room temperature for 4.5 hours. The reaction mixture was concentrated under reduced pressure. The residue was dissolved in ethyl acetate (100 ml), and then washed with 1 N hydrochloric acid (50 ml×2). The organic layer was separated, and dried over anhydrous sodium sulfate, and then the solvent was evaporated to obtain 1.17 g of the target compound (yield: 89%, m.p. 139–142° C.).

$^1$H-NMR (CD$_3$OD) δ (ppm) 2.30 (s, 6H), 3.15–3.50 (m, 8H), 4.12 (s, 2H), 7.12 (d, 4H), 7.50 (d, 4H)

Example 14

Synthesis of Compound 71

The reaction of Example 12 was repeated by using 940 mg of ethyl iodide instead of 2-chloromethylpyridine hydrochloride, and the product was purified by silica gel chromatography (eluent: methylene chloride/methanol=20/1) to obtain Compound 71 (1.49 g) as oil.

$^1$H-NMR (DMSO-d$_6$) δ (ppm) 0.89 (t, 3H), 2.48 (q, 2H), 2.60 (t, 4H), 2.80 (t, 4H), 6.78 (d, 4H), 7.25 (d, 4H), 9.62 (s, 2H)

Example 15

Syntheses of Compounds 72 to 81, Compounds 84 to 88, Compound 95, Compounds 102 to 103, Compounds 107 to 111, Compound 194, Compounds 197 to 201, Compounds 203 to 211 and Compound 213

The title compounds were synthesized in the same manner as in Example 14 by allowing Compound 45 obtained in Example 1 to react with corresponding alkylating agents.

Example 16

Syntheses of Compounds 89 to 91, Compounds 98 to 99, Compound 101, Compounds 105 to 106 and Compound 196

The title compounds were synthesized in the same manner as in Example 12 by allowing Compound 45 obtained in Example 1 to react with corresponding arylmethyl halides or heteroarylmethyl halides.

Example 17

Synthesis of Compound 92

Compound 92 was synthesized in accordance with the following synthetic scheme.

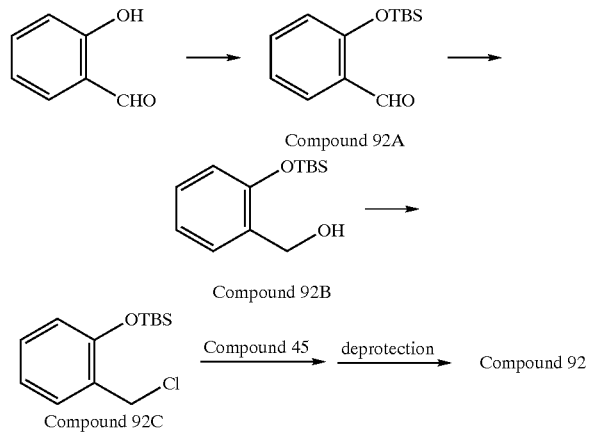

Salicyl aldehyde (12.2 g), imidazole (7.2 g), and dimethylformamide (70 ml) were put into a 200 ml three-neck flask for dissolution, tert-butyldimethylsilyl chloride (16 g) was added thereto at room temperature and the mixture was stirred at room temperature for 1 hour. Then, the reaction mixture was poured into water, and the mixture was extracted with ethyl acetate. The organic layer was washed with saturated brine, dried over magnesium sulfate, and concentrated under reduced pressure to obtain Compound 92A (23.5 g) as oil. The resulting Compound 92A was used for the subsequent reaction without further purification.

Compound 92A (18.9 g) was dissolved in 120 ml of methanol, and sodium borohydride (760 mg) was added thereto. The reaction mixture was stirred at room temperature for 1 hour, and then poured into water and the mixture was extracted with ethyl acetate. The organic layer was washed with saturated brine, dried over magnesium sulfate, and concentrated under reduced pressure to obtain Compound 92B (18.8 g) as oil. The resulting Compound 92B was used for the subsequent reaction without further purification.

Compound 92B (9.5 g), triethylamine (5.6 ml), and N,N-dimethylaminopyridine (500 mg) were dissolved in acetonitrile (50 ml), and methanesulfonyl chloride (4.6 g) was dropwise added thereto. The reaction mixture was left standing at room temperature overnight. The produced triethylamine hydrochloride was filtered, and the filtrate was concentrated under reduced pressure. To the residue was added hexane, and insoluble materials were removed by filtration. Then, the filtrate was washed with aqueous citric acid, water, and then saturated brine, then, dried over magnesium sulfate and concentrated under reduced pressure. The resulting residue was purified by silica gel column chromatography (eluent: hexane) to obtain Compound C (7.0 g) as oil.

Compound 45 (4.8 g) synthesized in Example 1 and dimethylacetamide (40 ml) were put into a 100 ml three-neck flask for dissolution, and Compound 92B (4.1 g) was added thereto. The reaction mixture was stirred at 80° C. for 1 hour, and then poured into water and the mixture was extracted with ethyl acetate. The organic layer was washed with saturated brine, dried over magnesium sulfate, and concentrated under reduced pressure. The residue was dissolved in methylene chloride (70 ml), 10 ml of 1 M solution of tetrabutylammonium fluoride in tetrahydrofuran was added thereto, and then the mixture was allowed to react at room temperature for 1 hour. The reaction mixture was poured into water, and the mixture was extracted with methylene chloride. The organic layer was washed with saturated brine, dried over magnesium sulfate, and concentrated under reduced pressure. The resulting residue was purified by silica gel column chromatography (eluent: methylene chloride/methanol=100/3) to obtain Compound 92 (4.93 g) as an amorphous.

Example 18

Syntheses of Compound 93 and Compound 94

The title compounds were synthesized in the same manner as in Example 17 by allowing Compound 45 obtained in Example 1 to react with benzyl chloride substituted with corresponding protected hydroxyl group, and then deprotecting the product.

Example 19

Syntheses of Compound 50, Compound 51 and Compound 54

The title compounds were synthesized in the same manner as in Example 2 by allowing Compound 45 obtained in Example 1 to react with a corresponding acid anhydride.

Example 20

Synthesis of Compound 53

Compound 45 (2.0 g) obtained in Example 1, formic acid (290 mg), and dicyclohexylamide (1.4 g) were stirred in a mixed solvent of chloroform (20 ml) and dimethyl sulfoxide (20 ml) at room temperature for 4 hours. The reaction mixture was filtered, and the residue was washed with ethyl acetate. Then, the filtrate and the washing filtrate were combined, and washed with water, saturated aqueous sodium hydrogen carbonate, and then saturated brine. The organic layer was dried over sodium sulfate, and concentrated under reduced pressure. The resulting residue was purified by silica gel column chromatography to obtain 2.1 g of the target compound.

$^1$H-NMR (DMSO-$d_6$) δ (ppm) 2.87 (m, 2H), 2.95 (m, 2H), 3.30 (m, 2H), 3.37 (m, 2H), 6.75 (d, 4H), 7.22 (d, 4H), 7.90 (s, 1H), 9.58 (broad, 2H)

Example 21

Synthesis of Compound 114

Compound 45 (9.64 mg) synthesized in Example 1, pyridine (0.25 ml), and dimethylacetamide (5 ml) were added to a 30 ml three-neck flask for dissolution. To the solution was added dropwise benzoyl chloride (5.34 mg) under ice cooling, and the mixture was stirred for 30 minutes under ice cooling, and then for 1 hour at room temperature. The reaction mixture was poured into diluted hydrochloric acid, and the mixture was extracted with ethyl acetate. The organic layer was washed with saturated brine, dried over magnesium sulfate, and then concentrated under reduced pressure. The resulting residue was purified by silica gel column chromatography (eluent: methylene chloride/methanol=10014), and crystallized by adding hexane to obtain 510 mg of the target compound.

Example 22

Syntheses of Compound 115, Compound 116 and Compound 117

The title compounds were synthesized in the same manner as in Example 22 by allowing Compound 45 obtained in Example 1 to react with a corresponding acid chloride, and purifying the product with a silica gel column.

Example 23

Synthesis of Compound 125

The title compound was synthesized in the same manner as in Example 7 by allowing Compound 45 obtained in Example 1 to react with piperidinocarbonyl chloride.

Example 24

Synthesis of Compound 214

Compound 45 (1.29 g) obtained in Example 1 and D-mannose (1.01 g) were stirred in ethanol (5 ml) at 100° C. for 4 hours on an oil bath. To the reaction mixture was added ethyl acetate (50 ml), the mixture was subjected to suction filtration, and then the filtrate was concentrated. The resulting residue was purified by silica gel column chromatography (methylene chloride/methanol=911) to obtain 1.05 g of the target compound.

$^1$H-NMR (DMSO-$d_6$) δ (ppm) 2.73 (m, 4H), 2.83 (m, 4H), 3.55–3.80 (m, 3H), 4.30–4.50 (m, 3H), 5.13 (s, 1H), 6.76 (d, 4H), 7.22 (d, 4H), 9.55 (s, 2H)

Example 25

Syntheses of Compounds 215 to 219

The title compounds were synthesized in the same manner as in Example 24 by allowing Compound 45 obtained in Example 1 to react with a corresponding saccharide.

Example 26

Synthesis of Compound 59

Compound 45 (500 mg) obtained in Example 1, N-{2-(p-toluenesulfonyloxy)ethyl}phthalimide (537 mg), potassium iodide (258 mg), and sodium hydrogen carbonate (131 mg) were stirred in dimethylformamide (8 ml) at 150° C. for 28 hours. The reaction mixture was extracted with ethyl acetate, and the organic layer was washed with saturated aqueous sodium hydrogen carbonate, dried over magnesium sulfate, and concentrated under reduced pressure. The resulting residue was purified by silica gel column chromatography to obtain 260 mg of phthalimide compound.

The above phthalimide compound (260 mg) and hydrazine monohydrate (31.58 mg) were stirred in ethanol (3 ml) with heating for 3 hours. The reaction mixture was extracted with ethyl acetate, and the organic layer was washed with saturated aqueous sodium hydrogen carbonate, dried over magnesium sulfate, and concentrated under reduced pressure. The resulting residue was purified by silica gel column chromatography (chloroform/methanol=1/1) to obtain 97 mg of the target compound.

$^1$H-NMR (DMSO-$d_6$) δ (ppm) 2.10 (m, 2H), 2.50–3.00 (m, 10H), 6.87 (d, 4H), 7.27 (d, 4H)

Example 27

Syntheses of Compounds 82 to 83, Compound 195 and Compound 202

The title compounds were synthesized by allowing Compound 59 obtained in Example 26 to react with sodium isocyanate, acetic anhydride, methanesulfonyl chloride and 3,5-dimethylpyrazole-1-carboxyamidine nitrate, respectively.

Example 28

Synthesis of Compound 48

4-(2-Bromoethylthio)phenol (1.2 g) was dissolved in dimethylformamide (10 ml) under nitrogen atmosphere, to this solution was added imidazole (1.5 g) and tert-butyldimethylsilyl chloride (2.45 g), and the mixture was stirred at room temperature for one and a half hours. To the reaction mixture was added water, the mixture was extracted with chloroform, and then the organic layer was dried over sodium sulfate, and concentrated under reduced pressure. The resulting residue was purified by silica gel column chromatography to obtain 1.4 g of silyl compound.

The above silyl compound (1.4 g) and hydroxylamine hydrochloride (150 mg) were mixed in ethanol (10 ml), sodium carbonate (400 mg) was added thereto, and the mixture was refluxed by heating for 8 hours. The reaction mixture was filtered, and the residue obtained by concentrating the filtrate under reduced pressure was purified by silica gel column chromatography (ethyl acetate/hexane=1/4) to obtain 506 mg of hydroxylamine compound.

The above hydroxylamine compound (480 mg) was dissolved in chloroform (10 ml), to the solution was added a solution of tetrabutylammonium fluoride in tetrahydrofuran (1 equivalent) and the mixture was stirred at room temperature for 20 minutes. The reaction mixture was concentrated under reduced pressure, and the resulting residue was purified by silica gel column chromatography, and recrystallized from a chloroform-hexane mixed solvent to obtain 320 mg of the target compound.

$^1$H-NMR (DMSO-d$_6$) δ (ppm) 2.85 (m, 6H), 3.00 (m, 2H), 6.77 (d, 4H), 7.22 (d, 4H), 8.98 (broad, 2H)

Example 29

Synthesis of Compound 49

Compounds 45 (200 mg) synthesized in Example 1 and 3,5-dimethylpyrazole-1-carboxyamidine nitrate (125 mg) were dissolved in dimethyl sulfoxide (4 ml). To this solution was added triethylamine (1.5 ml) and the mixture was stirred at 120° C. by heating for 4 hours. The reaction mixture was extracted with ethyl acetate, and the organic layer was washed with saturated aqueous sodium hydrogen carbonate, dried over magnesium sulfate, and concentrated under reduced pressure. The resulting residue was purified by silica gel column chromatography (ethyl acetate/methanol= 95/5) to obtain 30 mg of the target compound.

$^1$H-NMR (DMSO-d$_6$) δ (ppm) 2.33 (s, 3H), 2.72 (m, 4H), 3.13 (m, 4H), 6.53 (d, 4H), 7.03 (d, 4H), 9.42 (s, 2H)

Example 30

Synthesis of Compound 52

In a 100 ml three-neck flask, thiohydroquinone (1.6 g) was dissolved in methanol (15 ml) under nitrogen atmosphere. To this solution was added an aqueous solution (0.7 ml) of sodium hydroxide (0.51 g), N,N-bis(2-chloroethyl)-2-chloropropionamide (1.0 g) was further added, and the mixture was stirred at 50° C. for 2 hours. To the reaction mixture was added ethyl acetate and diluted hydrochloric acid for separation. The organic layer was washed with saturated brine, dried over sodium sulfate, and concentrated under reduced pressure. The resulting residue was purified by silica gel column chromatography (ethyl acetate/hexane= 3/2). The resulting oil was dissolved in methanol, water was added thereto, and then the precipitates produced were collected by filtration, and dried under reduced pressure to obtain 1.2 g of the target compound.

$^1$H-NMR (DMSO-d$_6$) δ (ppm) 2.32 (t, 2H), 2.86 (m, 6H), 3.32 (m, 4H), 6.70 (d, 6H), 7.22 (m, 6H), 9.60 (s, 3H)

Example 31

Synthesis of Compound 212

Compound 71 (0.51 g) synthesized in Example 14 and p-toluenesulfonic acid methyl ester (0.41 g) were stirred at 120° C. for 5 hours on an oil bath. To the reaction mixture was added ethyl acetate and acetone, the mixture was decanted, then to the residue was added a solution of potassium iodide (0.35 g) in acetone-methanol mixed solvent, and the mixture was subjected to suction filtration. The residue obtained by concentrating the filtrate under reduced pressure was purified by silica gel column chromatography (methylene chloride/methanol=9/1-8/2), and the resulting oil was crystallized by treatment with diethyl ether. The crystals were collected by filtration, and dried under reduced pressure to obtain 168 mg of the target compound.

$^1$H-NMR (DMSO-d$_6$) δ (ppm) 1.00 (t, 3H), 2.97 (s, 3H), 3.0–3.5 (m, 10H), 6.80 (d, 4H), 7.32 (d, 4H), 9.80 (s, 2H)

Example 32

Syntheses of Compounds 220 to 223

The title compounds were synthesized by carrying out the esterification in the same manner as in Example 13.

Example 33

Syntheses of Compound 224 and Compound 225

To a solution of Compound 97 (1.0 g) synthesized in Example 8 in acetone (10 ml) were added maleic acid (0.31 g), and further ethyl acetate. The resulting precipitates were separated by filtration, washed with ethyl acetate, and dried under reduced pressure to obtain 1.25 g of the target compound.

$^1$H-NMR (CD$_3$OD) δ (ppm) 2.95 (m, 4H), 3.07 (m, 4H), 3.63 (s, 2H), 6.28 (s, 2H), 6.76 (d, 4H), 7.27 (d, 4H)

In a similar manner, Compound 225 was obtained by using citric acid.

Example 34

Synthesis of Compound 226

Thiohydroquinone (5.05 g), 28% solution of sodium methoxide (8.2 g) in methanol, and methanol (30 ml) were mixed under water cooling. To the resulting solution was added a solution of 1,4-bis(5-bromopentanoyl)piperazine (8.8 g) in methanol (10 ml), and the mixture was stirred at 40° C. for 2 hours. The reaction mixture was cooled to room temperature, and concentrated under reduced pressure. The resulting residue was dissolved in ethyl acetate (200 ml), and washed with saturated brine (×2). The precipitates produced were separated by filtration, and dried under reduced pressure to obtain 9.00 g of the target compound.

$^1$H-NMR (DMSO-d$_6$) δ (ppm) 1.30–1.60 (m, 12H), 2.27 (t, 4H), 2.74 (t, 4H), 3.25–3.46 (m, 8H), 6.72 (d, 4H), 7.18 (d, 4H), 9.53 (s, 2H)

Example 35

Synthesis of Compound 227

Thiohydroquinone (4.0 g) was dissolved in methanol (20 ml). To this solution was added a 28% solution of sodium methoxide (6.7 g) in methanol, the mixture was stirred, a solution of 1,4-bis(2-chloropropionyl)piperazine (3.8 g) in methanol (20 ml) was further added thereto, and the mixture was refluxed by heating for 4 hours. The reaction mixture was cooled to room temperature, diluted hydrochloric acid was added thereto, and the mixture was extracted with ethyl acetate. The organic layer was washed with water, and the resulting precipitates were separated by filtration, and washed with ethyl acetate. These crystals were dried under reduced pressure to obtain 6.0 g of the target compound.

$^1$H-NMR (DMSO-d$_6$) δ (ppm) 2.60 (t, 4H), 2.96 (t, 4H), 3.28–3.56 (m, 8H), 6.76 (d, 4H), 7.23 (d, 4H), 9.62 (s, 2H)

Example 36

Synthesis of Compound 228

The title compound was synthesized in the same manner as in Example 35.

The results of mass spectroscopy (Fast Atom Bombardment Mass Spectroscopy, positive, p-Nitrobenzylalcohol) are described below.

TABLE 5

| Compound No. | Parent peak |
|---|---|
| 45 | 322 |
| 48 | 338 |
| 49 | 364 |
| 50 | 392 |
| 51 | 422 |
| 52 | 502 |
| 53 | 350 |
| 54 | 364 |
| 57 | 481 |
| 58 | 495 |
| 59 | 365 |
| 71 | 350 |
| 72 | 364 |
| 73 | 360 |
| 74 | 362 |
| 75 | 376 |
| 77 | 361 |
| 78 | 393 |
| 79 | 421 |
| 80 | 449 |
| 81 | 378 |
| 82 | 408 |
| 83 | 407 |
| 84 | 368 |
| 85 | 404 |
| 86 | 447 |
| 87 | 396 |
| 88 | 408 |
| 89 | 418 |
| 90 | 402 |
| 91 | 413 |
| 92 | 428 |
| 93 | 428 |
| 94 | 428 |
| 95 | 380 |
| 97 | 379 |
| 98 | 412 |
| 99 | 413 |
| 100 | 413 |
| 101 | 463 |
| 102 | 366 |
| 105 | 430 |
| 106 | 430 |
| 107 | 463 |
| 108 | 461 |
| 109 | 421 |
| 110 | 435 |
| 111 | 433 |
| 113 | 378 |
| 114 | 426 |
| 116 | 427 |
| 118 | 400 |
| 124 | 435 |
| 125 | 433 |
| 191 | 485 |
| 192 | 517 |
| 193 | 464 |
| 194 | 436 |
| 195 | 443 |
| 196 | 402 |
| 197 | 468 |
| 198 | 424 |
| 199 | 410 |
| 200 | 436 |
| 201 | 396 |
| 202 | 407 |
| 203 | 447 |
| 204 | 485 |
| 205 | 453 |
| 206 | 463 |
| 207 | 423 |
| 208 | 467 |
| 209 | 490 |
| 210 | 462 |
| 211 | 457 |
| 212 | 364 |
| 213 | 463 |
| 214 | 484 |
| 215 | 484 |
| 216 | 484 |
| 217 | 494 |
| 218 | 483 |
| 219 | 497 |
| 220 | 524 |
| 221 | 767 |
| 222 | 521 |
| 223 | 721 |
| 224 | 379 |
| 225 | 379 |

Text Example 1

Test of Measurement of RNR Inhibitory Activity (a) Preparation of R1 and R2 subunits of human RNR Starting from a plasmid p3I containing cDNA coding for R1 subunit of human RNR protein (disclosed in Nucleic Asids Research, 19, p.3741, 1991), a DNA was obtained, in which was introduced an Nde I restriction site just before the translation initiation site of R1 subunit and a Bam HI restriction site just after the translation termination site in such a manner that the amino acid sequence of R1 subunit was completely unchanged. The preparation of DNA was carried out by methods of introducing mutations and DNA amplification based on the PCR utilizing synthetic DNA fragments according to the method described in the Molecular Cloning, 2nd Edition. The Nde I/Bam HI restriction fragment containing a region coding for the R1 subunit deriving from the DNA was inserted between the NdeI and Bam HI sites of plasmid pET3a (Novagen) to construct a plasmid pETR1. The plasmid was transformed into Eschelichia coli BL21(λ DE3)plysS strain (Novagen) to construct a BL21(λ DE3)plysSpETR1 strain also according to the method described in the Molecular Cloning, 2nd Edition.

Similarly, a DNA fragment was obtained, from a human cell strain HL60 cDNA library through the methods of introducing mutations and DNA amplification based on the PCR utilizing synthetic DNA fragments, which was introduced with an Nde I restriction site just before the translation initiation site of $R^2$ subunit and a Bam HI restriction site just after the translation termination site in such a manner that the amino acid sequence of R2 subunit were completely unchanged. The Nde I/Bam HI restriction fragment containing the region coding for the R2 subunit deriving from the DNA was inserted between the NdeI and Bam HI sites of plasmid pEt3a (Novagen) to construct a plasmid pETR2. This plasmid was transformed into Eschelichia coli BL21(λ DE3)plysS strain (Novagen) also according to the method described in the Molecular Cloning, 2nd Edition to construct a BL21(λ DE3)plysSpETR2 strain.

By using one loop, the BL21(λ DE3) plysSpETR1 strain was inoculated to 40 ml of Terrific Broth (containing 100 μg/ml of ampicillin and 20 μg/ml of chloramphenicol and free from glycerol, described in Molecular Cloning, 2nd Edition) contained in a 300 ml Erlenmeyer flask, and cultured at 28° C. overnight with shaking. 30 ml of the culture broth was inoculated in 400 ml of the same culture broth contained in a 2 liter Erlenmeyer flask, and cultivation was carried out at 16° C. with shaking. Two hours after the start of the cultivation, IPTG was added to the broth to a final concentration of 0.1 mM, and then the cultivation was continued for 20 hours. Cells were collected from the culture broth by centrifugation at 7,000× g for 10 minutes at 4° C., and the cells collected were suspended in 20 ml of Buffer A [50 mM HEPES-NaOH (pH 7.6), 1 mM $MgCl_2$, 1 mM dithiothreitol, 1 mM PMSF] cooled with ice. This suspension was sonicated to disrupt the cells, and then centrifuged at 12,000×g for 20 minutes at 4° C. The supernatant was collected, streptomycin sulfate was added thereto to a final concentration of 2% (W/V) and the mixture was maintained on ice for 20 minutes, and then centrifuged at 12,000× g for 20 minutes at 4° C. The supernatant was collected, an equal volume of 100% saturated aqueous ammonium sulfate was added thereto with stirring, and then the mixture was maintained on ice overnight. Precipitates were collected by centrifugation at 15,000×g for 20 minutes at 4° C. and dissolved in 2 ml of Buffer A, and then the solution was subjected to desalting and buffer substitution with Buffer A by using PD-10 (Pharmacia Biotech) in a conventional manner.

For all of the subsequent separation and purification steps, FPLC System (Pharmacia Biotech) was used. The desalted fraction was applied to Q-Sepharose FF (Pharmacia Biotech), and separation was carried out under the following conditions: flow rate: 5.0 ml/minute, separation time: 50 minutes, eluent: 0 M to 0.5 M KCl linear gradient in 10 mM potassium phosphate buffer (pH 7.0). The fractions eluted from 10 minutes to 20 minutes were collected and ammonium sulfate was added thereto to a final concentration of 0.5 M. The fractions were applied to Phenyl Sepharose HP (Pharmacia Biotech) and eluted at a flow rate of 3.0 ml/minute with 10 mM potassium phosphate buffer (pH 7.0)/0.5 M ammonium sulfate for 15 minutes, with 10 mM potassium phosphate buffer (pH 7.0) for 15 minutes, and then with 10 mM potassium phosphate buffer (pH 7.0)/0.3% Tween 20 for 15 minutes. The fractions eluted in the last 15 minutes were collected and applied to Resource Q 1 ml (Pharmacia Biotech), washed with 10 mM potassium phosphate buffer (pH 7.0), and eluted at a flow rate of 1 ml/minute with 10 mM potassium phosphate buffer (pH 7.0)/0.3 M KCl for 10 minutes. The fractions eluted in the first 3 minutes were collected, and subjected to desalting and buffer substitution with Buffer A by using PD-10 to obtain a purified R1 preparation.

By using one loop, the BL21($\lambda$ DE3) plysSpETR$^2$ strain was inoculated to 40 ml of Terrific Broth (containing 100 $\mu$g/ml of ampicillin and 20 $\mu$g/ml of chloramphenicol and free from glycerol, described in Molecular Cloning, 2nd Edition) in a 300 ml Erlenmeyer flask, and cultured at 28° C. overnight with shaking. 30 ml of the culture broth was inoculated to 400 ml of the same culture broth in a 2 liter Erlenmeyer flask, and then the cultivation was carried out at 28° C. with shaking. When O.D. (600 nm) reached around 0.8, IPTG was added to the broth to a final concentration of 1 mM, and the cultivation was continued for 6 hours. Cells were collected from the culture broth by centrifugation at 7,000×g for 10 minutes at 4° C., and the cells obtained were suspended in 20 ml of Buffer A cooled with ice. This suspension was sonicated to disrupt the cells, and then centrifuged at 12,000×g for 20 minutes at 4° C. The supernatant was collected, streptomycin sulfate was added thereto to a final concentration of 2% (W/V), and the mixture was maintained on ice for 20 minutes, and then centrifuged at 12,000×g for 20 minutes at 4° C. The supernatant was collected, an equal volume of 100% saturated aqueous ammonium sulfate was added thereto with stirring, and then the mixture was maintained on ice overnight. Precipitates were collected by centrifugation at 15,000× for 20 minutes at 4° C. and dissolved in 2 ml of Buffer A, and then the solution was subjected to desalting and buffer substitution with Buffer A by using PD-10 (Pharmacia Biotech) in a conventional manner.

For all of the subsequent separation and purification steps, FPLC System (Pharmacia Biotech) was used. The desalted fraction was applied to Q-Sepharose FF (Pharmacia Biotech), and separation was carried out under the following conditions: flow rate: 5.0 ml/minute, separation time: 50 minutes, eluent: 0 M to 0.5 M KCl linear gradient in 10 mM potassium phosphate buffer (pH 7.0). The fractions eluted from 10 minutes to 25 minutes were collected, ammonium sulfate was added thereto to a final concentration of 0.5 M, and the mixture was applied to Resource ETH. The fractions were eluted at a flow rate of 0.5 ml/minute with 10 mM potassium phosphate buffer (pH 7.0)/0.5 M ammonium sulfate for 15 minutes, with 10 mM potassium phosphate buffer (pH 7.0) for 15 minutes, and then with 10 mM potassium phosphate buffer (pH 7.0)/0.3% Tween 20 for 15 minutes. The fractions eluted in the last 15 minutes were collected and applied to Resource Q 1 ml (Pharmacia Biotech), and then washed with 10 mM potassium phosphate buffer (pH 7.0)/0.5 M ammonium sulfate at a flow rate of 1 ml/minute for 10 minutes. The fractions were eluted with 10 mM potassium phosphate buffer for 10 minutes. The fractions eluted in the first 3 minutes were collected, and subjected to desalting and buffer substitution with Buffer A by using PD-10 to obtain a purified $R^2$ preparation.

(b) In vitro Measurement of Human RNR Inhibitory Activity

By using the above-obtained human RNR subunits, inhibitory activity on the human RNR was tested in vitro. The composition of the reaction mixture is as follows:

50 mM HEPES-NaOH (pH 7.6)
5 mM $MgCl_2$
10 mM Dithiothreitol
100 $\mu$M CDP
1 mM ATP
40 ng/ml Purified human RNR R1 subunit, and
40 ng/ml Purified human RNR R2 subunit.

The above reaction mixture (25 $\mu$l) containing a test compound at an appropriate final concentration was prepared, and the conversion from CDP to dCDP by RNR was carried out at 37° C. for 30 minutes. The reaction mixture was subjected to a heat treatment at 95° C. for 5 minutes, and centrifuged at 10,000× g for 5 minutes at 4° C. 20 $\mu$l of the supernatant was collected and 5 $\mu$l of 25 mg/ml snake venom (Sigma) was added thereto. Dephosphorylation reaction was carried out at 37° C. for 60 minutes to allow complete conversion of CDP, ATP and dCDP as the reaction product present in the reaction mixture into CR, AR and CdR, respectively. The reaction mixture was subjected to a heat treatment at 95° C. for 5 minutes, and centrifuged at 10,000× g for 5 minutes at 4° C. 180 $\mu$l of acetonitrile was added to 20 $\mu$l of the supernatant, and the mixture was centrifuged again at 10,000× g for 5 minutes at 4° C., and the resulting supernatant was used as a sample for analysis. The analysis was performed by high performance liquid chromatography. Analytical conditions are as follows:

Column: Licrospher NH2 (Merck)
Flow rate: 1.5 ml/min
Detection: 270 nm, and
Eluent: acetonitrile/water (90:10, V/V).

CdR in the analyzed sample was identified and its concentration was determined by comparison with elution time and peak area with those of CdR at known concentration. A concentration of a test compound which inhibited the RNR activity by 50% under the aforementioned conditions was calculated by comparing a CdR concentration in a sample, obtained from the reaction without drug treatment, with a CdR concentration in a sample obtained from the reaction wherein the test compound at a known concentration was added, and the value obtained was determined as $IC_{50}$.

Test Example 2

Test for Growth Inhibition of Hela S3 Cells

HeLa S3 cells prepared at $1\times10^4$ cells/ml in MEM culture medium containing 10% fetal bovine serum and 2 mM glutamine were added to each well of a 96-well microtiter plate (0.1 ml for each well). The cells were cultured at 37° C. in a $CO_2$ incubator for 24 hours, and then 0.05 ml of test compound appropriately diluted with the above medium was added to each well, and then the mixture was cultured at 37° C. in a $CO_2$ incubator for 72 hours. After the culture supernatant was removed, each well was washed with 0.1 ml of PBS buffer twice, and 0.1 ml of the aforementioned medium was added to each well again.

Cell Proliferation Kit II (Boehringer Mennheim) was used for measurement of cell number in each well. After a coloring reaction reagent was added, the plate was warmed to 37° C. in a $CO_2$ incubator for 3 hours. Then, absorbances at 490 nm and 655 nm were measured by a microplate reader, and a value (difference of absorbance) was calculated for each well by subtracting the absorbance at 650 nm from the absorbance at 490 nm. By comparing the differences of absorbance for cells without treatment and cells treated with a test compound at a known concentration, a concentration of test compound which inhibited the cell growth by 50% was calculated, and the value obtained was determined as $IC_{50}$. The values of RNR inhibitory activity obtained in Example 8, and the values of cell growth inhibitory activity obtained in Example 9 are shown in the following tables (the compound numbers used in the tables correspond to the compound numbers shown in the aforementioned tables).

TABLE 6

| Compound No. | RNR Inhibition ($IC_{50}$, μM) | Cell growth inhibition ($IC_{50}$, μM) |
| --- | --- | --- |
| 1 | 4.26 | 5.15 |
| 7 | 4.82 | >101 |
| 8 | 4.38 | 6.50 |
| 27 | 0.50 | 1.53 |
| 45 | 3.64 | 5.64 |
| 48 | 1.73 | 5.16 |
| 49 | 5.45 | 16.04 |
| 50 | 3.97 | 3.81 |
| 52 | 4.38 | 6.50 |
| 53 | 1.05 | 1.71 |
| 54 | 0.48 | 4.63 |
| 55 | 6.87 | 7.78 |
| 57 | 0.73 | 14.44 |
| 58 | 4.76 | 18.59 |
| 59 | 5.73 | 5.81 |
| 60 | 2.75 | 7.67 |
| 61 | 3.77 | 13.40 |
| 71 | 1.23 | 3.94 |
| 72 | 1.19 | 2.18 |
| 73 | 0.60 | 1.61 |
| 74 | 0.82 | 2.00 |
| 75 | 1.66 | 3.56 |
| 77 | 0.06 | 2.38 |
| 78 | 0.31 | 1.61 |
| 79 | 1.37 | 3.06 |
| 80 | 0.74 | 1.43 |
| 81 | 0.29 | 1.23 |
| 82 | 1.42 | 1.30 |
| 83 | 2.95 | 5.17 |
| 84 | 2.74 | 11.99 |

TABLE 6-continued

| Compound No. | RNR Inhibition ($IC_{50}$, μM) | Cell growth inhibition ($IC_{50}$, μM) |
| --- | --- | --- |
| 85 | 0.61 | 2.50 |
| 86 | 3.14 | 3.78 |
| 87 | 1.01 | 2.57 |
| 88 | 1.79 | 3.22 |
| 89 | 1.46 | 4.66 |
| 90 | 2.03 | 6.38 |
| 91 | 1.69 | 2.72 |
| 92 | 0.89 | 2.14 |
| 93 | 0.63 | 9.04 |
| 94 | 0.46 | 4.00 |
| 95 | 0.88 | 3.56 |
| 97 | 0.17 | 0.88 |
| 98 | 3.36 | 14.97 |
| 99 | 2.79 | 5.80 |
| 100 | 1.58 | 4.97 |
| 101 | 5.05 | 12.88 |
| 102 | 0.69 | 1.42 |
| 103 | 2.11 | 1.74 |
| 104 | 2.11 | 1.74 |
| 105 | 3.99 | 9.07 |
| 106 | 4.64 | 6.77 |
| 107 | 4.20 | 24.86 |
| 108 | 0.64 | 2.64 |
| 109 | 2.36 | 38.89 |
| 111 | 1.85 | 11.39 |
| 113 | 4.77 | 3.80 |
| 114 | 3.44 | 2.74 |
| 115 | 4.14 | 6.14 |
| 116 | 4.13 | 3.02 |
| 117 | 1.69 | 2.72 |
| 118 | 6.87 | 7.78 |
| 124 | 0.09 | 3.68 |
| 125 | 0.91 | 4.55 |
| 131 | 6.59 | 127.70 |
| 132 | 3.50 | 45.55 |
| 133 | 2.27 | 14.51 |
| 134 | 0.68 | 2.05 |
| 135 | 0.43 | 6.02 |
| 136 | 0.69 | 9.14 |
| 137 | 0.87 | 5.45 |
| 138 | 2.29 | 18.28 |
| 152 | 5.14 | 17.96 |
| 156 | 2.27 | 5.45 |
| 158 | 1.42 | 12.72 |
| 159 | 0.69 | 6.89 |
| 160 | 0.95 | 20.09 |
| 161 | 1.13 | 34.19 |
| 162 | 1.70 | 3.70 |
| 163 | 2.10 | 5.17 |
| 165 | 3.98 | 50.14 |
| 166 | 3.09 | 31.25 |
| 171 | 8.01 | 30.03 |
| 172 | 2.64 | 19.48 |
| 173 | 3.63 | 12.93 |
| 183 | 0.42 | 10.42 |
| 184 | 0.30 | 2.46 |
| 186 | 11.93 | 56.03 |
| 190 | 1.38 | 16.86 |
| 191 | 1.36 | 4.78 |
| 192 | 2.85 | 4.51 |
| 193 | N.T. | 0.36 |
| 194 | 0.84 | 11.71 |
| 195 | 0.55 | 3.16 |
| 196 | 1.52 | 7.08 |
| 197 | 3.24 | 4.06 |
| 198 | 4.86 | 4.85 |
| 199 | 3.99 | 5.14 |
| 200 | 4.20 | 4.13 |
| 201 | 2.49 | 4.29 |
| 202 | 1.87 | 42.64 |
| 203 | 3.18 | 3.45 |
| 204 | 1.50 | 3.38 |
| 205 | 1.19 | 7.32 |
| 206 | 1.13 | 3.31 |
| 207 | 0.87 | 1.71 |
| 208 | 3.46 | 5.93 |

TABLE 6-continued

| Compound No. | RNR Inhibition (IC$_{50}$, μM) | Cell growth inhibition (IC$_{50}$, μM) |
|---|---|---|
| 209 | 2.67 | 3.09 |
| 210 | 5.91 | 2.82 |
| 211 | 3.24 | 3.04 |
| 213 | 2.06 | 179.95 |
| 214 | 2.69 | 7.73 |
| 215 | 3.68 | 12.72 |
| 216 | 3.63 | 11.54 |
| 218 | 4.97 | 23.18 |
| 219 | 3.51 | 25.20 |
| 220 | 5.20 | 0.29 |
| 222 | 0.43 | 0.36 |
| 224 | 0.42 | 0.40 |
| 225 | 0.63 | 0.55 |

N.T.: Not tested.

Test Example 3

Antineoplastic Effect Against Human Ovary Cancer A2780 Cells 2 mm cubes (tumor fragments of 8 mm$^3$) of human ovary cancer A2780 cells were subcutaneously transplanted to nude mice BALB/cAJcl-nu (CLEA JAPAN) in the abdomens. When the tumor volume reached to from 50 to 300 mm$^3$ after the transplantation, the mice were arbitrarily divided into groups each consisting of 5 mice, and intraperitoneally administered with a drug solution once a day for 5 days. After weighing compounds, the drug solution was prepared before use by dissolving the drug in 99.5% ethanol (final concentration: 5%, analytical grade, Kanto Kagaku) or N,N-dimethylacetamide (final concentration: 5%, analytical grade, Kanto Kagaku), adding CREMOPHOR EL (a derivative of caster oil and ethylene oxide, final concentration: 10%, Sigma Chemical) to the solution, and suspending the solution in physiological saline (Otsuka Physiological Saline for Injection, Otsuka Pharmaceutical). For evaluation of the effect, a tumor volume was calculated in accordance with Equation 1, a ratio of tumor volume (V) after the administration of drug solution to tumor volume (V$_0$) before the administration of drug solution was calculation (V/V$_0$), and the ratio was compared with that for the untreated group to determine T/C (Equation 2). The results are shown in the table set out below. In the table, administration dose, T/C and evaluation day are shown.

Equation 1:

Tumor volume (mm$^3$) = Length (mm) × Width (mm) × Width (mm) × 1/2

Equation 2:

$T/C = (V/V_0$ for drug-administered group$)/$
$(V/V_0$ for untreated group$)$

TABLE 7

| Compound No. | Dose mg/kg/day | Antitumor activity T/C | Evaluation day* |
|---|---|---|---|
| 27 | 500 | 0.46 | 7 |
| 48 | 500 | 0.54 | 7 |
| 72 | 500 | 0.50 | 4 |

TABLE 7-continued

| Compound No. | Dose mg/kg/day | Antitumor activity T/C | Evaluation day* |
|---|---|---|---|
| 77 | 500 | 0.54 | 4 |
| 78 | 500 | 0.53 | 4 |
| 79 | 500 | 0.40 | 4 |
| 91 | 500 | 0.48 | 4 |
| 94 | 500 | 0.53 | 7 |
| 97 | 500 | 0.43 | 7 |
| 102 | 500 | 0.47 | 7 |
| 103 | 500 | 0.50 | 4 |
| 193 | 250 | 0.46 | 4 |
| 209 | 500 | 0.50 | 7 |
| 211 | 500 | 0.37 | 9 |
| 177 | 500 | 0.54 | 4 |
| 227 | 500 | 0.53 | 7 |

*Days after the first administration of test compound

Test Example 4

Antineoplastic Effect Against Human Lung Cancer Lu-65 Cells 2 mm cubes (tumor fragments of 8 mm$^3$) of human lung cancer Lu-65 cells were subcutaneously transplanted to nude mice BALB/cAJcl-nu (CLEA JAPAN) on their abdomens. When the tumor volume reached to from 50 to 300 mm$^3$ after the transplantation, the mice were arbitrarily divided into groups each consisting of 5 mice, and intraperitoneally administered with a drug solution twice a day for 5 days. After weighing compounds, the drug solution was prepared before use by dissolving the drug in 99.5% ethanol (final concentration: 5%, analytical grade, Kanto Kagaku), adding CREMOPHOR EL (a derivative of caster oil and ethylene oxide, final concentration: 10%, Sigma Chemical) to the solution, and suspending the solution in physiological saline (Otsuka Physiological Saline for Injection, Otsuka Pharmaceutical). For evaluation of the effect, a tumor volume was calculated in accordance with Equation 1, a ratio of tumor volume (V) after the administration of drug solution to tumor volume (V$_0$) before the administration of drug solution was calculated (V/V$_0$), and the ratio was compared with that for the untreated group to determine T/C (Equation 2). The results are shown in the table set out below.

Equation 1:

Tumor volume (mm$^3$) = Length (mm) × Width (mm) × Width (mm) × 1/2

Equation 2:

$T/C = (V/V_0$ for drug-administered group$)/$
$(V/V_0$ for untreated group$)$

TABLE 8

| Compound No. | Dose mg/kg/day | Antitumor activity T/C | Evaluation day* |
|---|---|---|---|
| 27 | 1000 (500 × 2) | 0.25 | 7 |

*Days after the first administration of test compound

INDUSTRIAL AVAILABILITY

The compounds of the aforementioned formula (I) or (II), which are the active ingredient of the medicament of the present invention, can inhibit ribonucleotide reductase, and selectively inhibit proliferation of cancer cells. Therefore, the medicament of the present invention is useful, for example, as an agent for cancer treatment. The novel compounds represented by the aforementioned formula (XII) provided by the present invention are useful as active ingredients of medicaments such as medicaments for cancer treatment.

What is claimed is:

1. A method for inhibiting ribonucleotide reductase comprising administering to a subject in need thereof an effective amount of a compound represented by formula (I), or a physiologically acceptable salt thereof:

$$Ar^1—S—R^1—S—Ar^2 \quad (I)$$

wherein $R^1$ represents a nonmetal bridging group selected from —$C_2H_4$—S—$C_2H_4$—, —$C_2H_4$—S—$C_3H_6$—, —$C_2H_4$—S—$C_4H_4$—, —$C_2H_4$—S—$C_4H_6$—, —$C_2H_4$S—$C_4H_8$—, —$C_3H_6$—S—$C_3H_6$—, —$C_3H_6$—S—$C_4H_6$—, —$C_3H_6$—S—$C_4H_8$—, —$C_4H_8$—S—$C_4H_8$—, —$CH_2CO$—S—$C_2H_4$—, —$CH_2CO$—S—$C_3H_6$—, —$CH_2CO$—S—$C_4H_8$—, —$CH_2CO$—S—$C_4H_6$—, —$CH_2CO$—S—$C_4H_4$—, —$CH(CH_3)CO$—S—$C_2H_4$—, —$C_2H_4CO$—S—$CH_2CH(OH)CH_2$—, —$CH_2CO$—S—$C_2H_4NHCOCH_2$—, —$C_2H_4CO$—S—$C_2H_4NHCOC_2H_4$—, —$C_2H_4O$—$C_2H_4$—, —$C_2H_4$—O—$C_3H_6$—, —$C_2H_4$—O—$C_4H_4$—, —$C_2H_4$—O—$C_4H_6$—, —$C_2H_4$—O—$C_4H_8$—, —$C_3H_6$—O—$C_3H_6$—, —$C_3H_6$—O—$C_4H_6$—, —$C_3H_6$—O—$C_4H_8$—, —$C_4H_8$—O—$C_4H_8$—, —$CH_2CO$—O—$C_2H_4$—, —$CH_2CO$—O—$C_3H_6$—, —$CH_2CO$—O—$C_4H_8$—, —$CH_2CO$—O—$C_4H_6$—, —$CH_2CO$—O—$C_4H_4$—, —$CH(CH_3)CO$—O—$C_2H_4$—, —$C_2H_4CO$—O—$CH_2CH(OH)CH_2$—, —$CH_2CO$—O—$C_2H_4NHCOCH_2$—, —$C_2H_4CO$—O—$C_2H_4NHCOC_2H_4$—; —$R^2$—N($R^4$)—$R^3$—, wherein $R^2$, $R^3$ and $R^4$ are defined as follows:

| $R^2$ | $R^3$ | $R^4$ |
|---|---|---|
| —$C_2H_4$— | —$C_2H_4$— | —H— |
| —$C_3H_6$— | —$C_3H_6$— | —H— |
| —$C_4H_8$— | —$C_4H_8$— | —H— |
| —$C_2H_4$— | —$C_2H_4$— | —OH— |
| —$C_2H_4$— | —$C_2H_4$— | —C(=NH)$NH_2$ |
| —$C_2H_4$— | —$C_2H_4$— | —$COC_3H_7$ |
| —$C_2H_4$— | —$C_2H_4$— | —$COCH_2CH_2CO_2H$ |
| —$C_2H_4$— | —$C_2H_4$— | —$COCH_2CH_2S$—Ph—OH-p |
| —$C_2H_4$— | —$C_2H_4$— | —CHO |
| —$C_2H_4$— | —$C_2H_4$— | —$COCH_3$ |
| —$C_2H_4$— | —$C_2H_4$— | —$SO_2CH_3$ |
| —$C_3H_6$— | —$C_3H_6$— | —CHO |
| —$C_2H_4$— | —$C_2H_4$— | —$CH_2CH_2NH_2$ |
| —$CH_2CO$— | —$C_2H_4$— | —H |
| —$CH_2CO$— | —$C_3H_6$— | —H |
| —$CH_2CO$— | —$C_4H_8$— | —H |
| —$CH_2CO$— | —$C_4H_6$— | —H |
| —$CH_2CO$— | —$C_4H_4$— | —H |
| —$CH_2CO$— | —$C_4H_4$— | —CHO |
| —$CH(CH_3)CO$— | —$C_2H_4$— | —H |
| —$CH(CH_3)CO$— | —$C_2H_4$— | —$C_2H_4OH$ |
| —$C_2H_4CO$— | —$CH_2CH(OH)CH_2$— | —$C_2H_4OH$ |
| —$CH_2CO$— | —$C_2H_4NHCOCH_2$— | —H |
| —$C_2H_4CO$— | —$C_2H_4NHCOC_2H_4$— | —H |
| —$C_2H_4$— | —$C_2H_4$— | —$C_2H_5$ |
| —$C_2H_4$— | —$C_2H_4$— | —$C_3H_7$ |
| —$C_2H_4$— | —$C_2H_4$— | —$CH_2$—C≡CH |
| —$C_2H_4$— | —$C_2H_4$— | —$CH_2$—CH=$CH_2$ |
| —$C_2H_4$— | —$C_2H_4$— | —$CH_2$-cyclopropyl |

| $R^2$ | $R^3$ | $R^4$ |
|---|---|---|
| —$C_2H_4$— | —$C_2H_4$— | —$CH_2$—$SO_2NH_2$ |
| —$C_2H_4$— | —$C_2H_4$— | —$CH_2$—CN |
| —$C_2H_4$— | —$C_2H_4$— | —$C_2H_4$—CO—$NH_2$ |
| —$C_2H_4$— | —$C_2H_4$— | —$C_2H_4CO$—N($CH_3$)$_2$ |
| —$C_2H_4$— | —$C_2H_4$— | —$C_2H_4CO$—N($C_2H_5$)$_2$ |
| —$C_2H_4$— | —$C_2H_4$— | —$CH_2$—CO—$CH_3$ |
| —$C_2H_4$— | —$C_2H_4$— | —$C_2H_4$—NH—CO—$NH_2$ |
| —$C_2H_4$— | —$C_2H_4$— | —$C_2H_4$—NH—CO—$CH_3$ |
| —$C_2H_4$— | —$C_2H_4$— | —$CH_2F$ |
| —$C_2H_4$— | —$C_2H_4$— | —$CF_3$ |
| —$C_2H_4$— | —$C_2H_4$— | —$C_2H_4$-(N-succinimido) |
| —$C_2H_4$— | —$C_2H_4$— | —$C_2H_4$—S—$CH_3$ |
| —$C_2H_4$— | —$C_2H_4$— | —$CH_2$-ethyleneacetal |
| —$C_2H_4$— | —$C_2H_4$— | —$CH_2$-(2-thienyl) |
| —$C_2H_4$— | —$C_2H_4$— | -furfuryl |
| —$C_2H_4$— | —$C_2H_4$— | —$CH_2$-(4-pyridyl) |
| —$C_2H_4$— | —$C_2H_4$— | -o-hydroxybenzyl |
| —$C_2H_4$— | —$C_2H_4$— | -m-hydroxybenzyl |
| —$C_2H_4$— | —$C_2H_4$— | -p-hydroxybenzyl |
| —$C_2H_4$— | —$C_2H_4$— | —($CH_2$)$_3$—OH |
| —$C_2H_4$— | —$C_2H_4$— | —$CH_2$—NH—CO—$CH_3$ |
| —$C_2H_4$— | —$C_2H_4$— | —$CH_2$—CO—$NH_2$ |
| —$C_2H_4$— | —$C_2H_4$— | -benzyl |
| —$C_2H_4$— | —$C_2H_4$— | —$CH_2$-(3-pyridyl) |
| —$C_2H_4$— | —$C_2H_4$— | —$CH_2$-(2-pyridyl) |
| —$C_2H_4$— | —$C_2H_4$— | —$CH_2$-(2-quinolinyl) |
| —$C_2H_4$— | —$C_2H_4$— | —$C_2H_4$—OH |
| —$C_2H_4$— | —$C_2H_4$— | —($CH_2$)$_3$—$OCH_3$ |
| —$C_2H_4$— | —$C_2H_4$— | —$C_2H_4$—$OCH_3$ |
| —$C_2H_4$— | —$C_2H_4$— | -o-fluorobenzyl |
| —$C_2H_4$— | —$C_2H_4$— | -p-fluorobenzyl |
| —$C_2H_4$— | —$C_2H_4$— | —$C_2H_4$—CO-(N-morpholino) |
| —$C_2H_4$— | —$C_2H_4$— | —$C_2H_4$—CO-(1-piperidyl) |
| —$C_2H_4$— | —$C_2H_4$— | —$C_2H_4$—N($C_2H_5$)$_2$ |
| —$C_2H_4$— | —$C_2H_4$— | —$C_2H_4$-(N-morpholino) |
| —$C_2H_4$— | —$C_2H_4$— | —$C_2H_4$-(1-piperidyl) |
| —$C_2H_4$— | —$C_2H_4$— | —CO—$CH_3$ |
| —$C_2H_4$— | —$C_2H_4$— | —CO—$C_2H_5$ |
| —$C_2H_4$— | —$C_2H_4$— | —CO—$C_6H_5$ |
| —$C_2H_4$— | —$C_2H_4$— | —CO-(2-pyridyl) |
| —$C_2H_4$— | —$C_2H_4$— | —CO-(3-pyridyl) |
| —$C_2H_4$— | —$C_2H_4$— | —CO-(4-pyridyl) |
| —$C_2H_4$— | —$C_2H_4$— | —$SO_2$—$CH_3$ |
| —$C_2H_4$— | —$C_2H_4$— | —$SO_2$—$C_6H_5$ |
| —$C_2H_4$— | —$C_2H_4$— | —CO—$NH_2$ |
| —$C_2H_4$— | —$C_2H_4$— | —CO—NH($CH_3$) |
| —$C_2H_4$— | —$C_2H_4$— | —CO—N($CH_3$)$_2$ |
| —$C_2H_4$— | —$C_2H_4$— | —CO—N($C_2H_5$)$_2$ |
| —$C_2H_4$— | —$C_2H_4$— | —CO-(N-morpholino) |
| —$C_2H_4$— | —$C_2H_4$— | —CO-(1-piperidyl) |
| —$C_2H_4$— | —$C_2H_4$— | —CO—NH—$C_6H_5$ |
| —$C_2H_4$— | —$C_2H_4$— | —CO—NH-(2-pyridyl) |
| —$C_2H_4$— | —$C_2H_4$— | —$SO_2$—$NH_2$ |
| —$C_2H_4$— | —$C_2H_4$— | —$SO_2$—N($C_2H_5$)$_2$ |
| —$C_2H_4$— | —$C_2H_4$— | —$SO_2$-(N-morpholino); |

—$CH_2$—, —$C_2H_4$—, —$C_3H_6$—, —$C_4H_8$—, —$C_5H_{10}$—, —$C_6H_{12}$—, —$C_7H_{14}$—, —$C_8H_{16}$—, —$C_9H_{18}$—, —$C_{10}H_{20}$—, —$C_{11}H_{22}$, —$C_2H_4$—$SO_2$—$C_2H_4$—$SO_2$—$C_2H_4$—, —CH($CH_3$), —CH($C_2H_5$)—, CH(n—$C_3H_7$)—, —CH($C_6H_5$)—, —C($CH_3$)$_2$—, —CH(COOH)—, CH($C_2H_4$OH)—, —CH($CH_3$)—$CH_2$—, —CH($C_2H_4$OH)—$CH_2$—, —CH(COOH)—$CH_2$—, —CH($C_2H_5$)—$CH_2$—, —$CH_2$—CH(OH)—$CH_2$—, —$CH_2$—C($CH_2$B)$_2$—$CH_2$, wherein B is p-hydroxyphenylthio, $CH_2$—S—$CH_2$—, —$CH_2$—CH=CH—$CH_2$—, —$CH_2$—C≡C—$CH_2$—, —$CH_2$—$C_6H_4$—$CH_2$— wherein —$C_6H_4$—, is an o-phenylene group, —$C_2H_4$—O—$CH_2$—O—$C_2H_4$—, —$C_2H_4$—O—$C_2H_4$—O—$C_2H_4$—, —$CH_2$—COO—$C_2H_4$—OCOCH$_2$—, —$CH_2$—COO—$C_3H_6$—OCOCH$_2$—, —$CH_2$CH(OH)$CH_2$—O—$C_2H_4$—O—$CH_2$CH(OH)$CH_2$—, —($C_2H_4$O)$_2$—CO—$CH_2$—CO—($C_2H_4$O)$_2$—, —($C_2H_4$O)$_2$—CO—(trans)CH=CH—CO—($C_2H_4$O)$_2$—, —$CH_2$—COO—($C_2H_4$O)$_3$—CO—$CH_2$—, —$CH_2$—COO—

93
$(C_2H_4O)_4-CO-CH_2-$, $-(C_2H_4O)_3-C_2H_4-$,
$-(C_2H_4O)_4-C_2H_4-$, $-(C_2H_4O)_5-C_2H_4-$,
$-(C_2H_4O)_3-CO-(C_2H_4O)_3-$, $-(C_2H_4O)_2-CO-C_2H_4-CO-(C_2H_4O)_2-$, $-CH_2-CO-CO-CH_2-$,
$-CO-CH_2-CO-$,
94
-continued
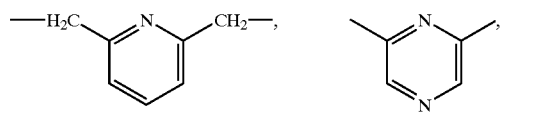
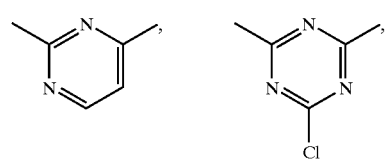
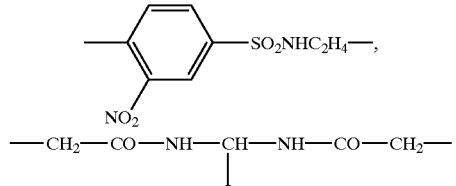
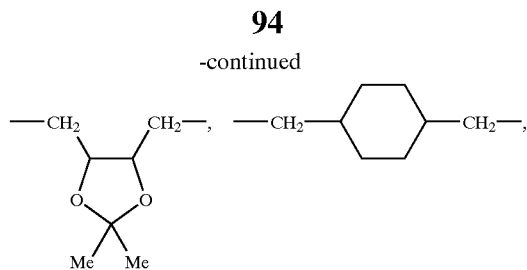
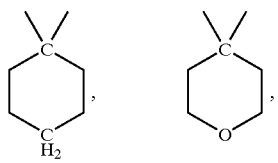
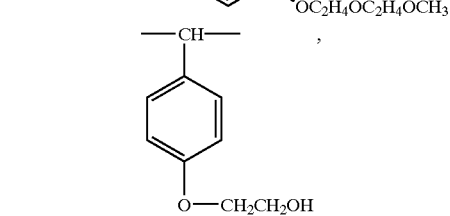
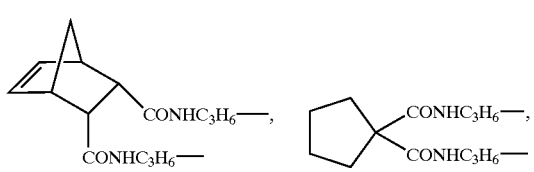
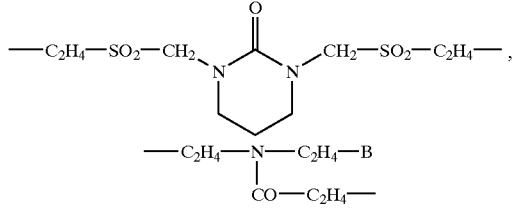
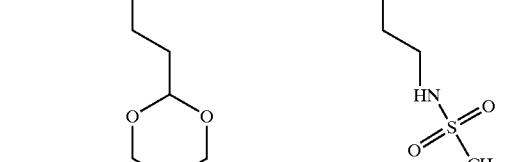
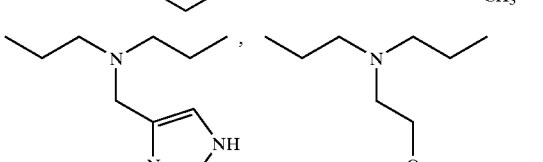
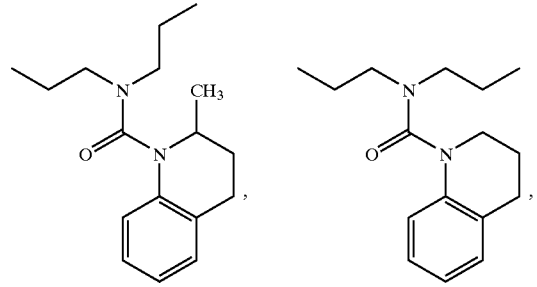
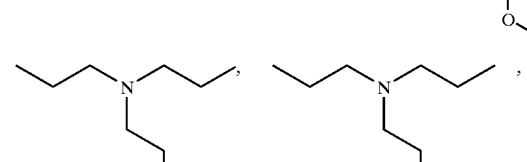
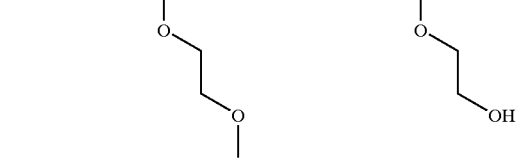
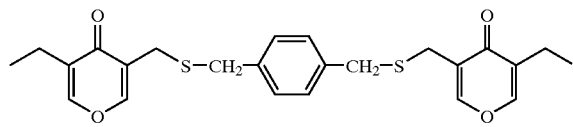
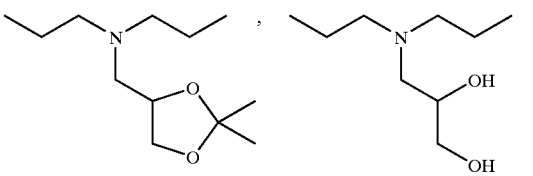

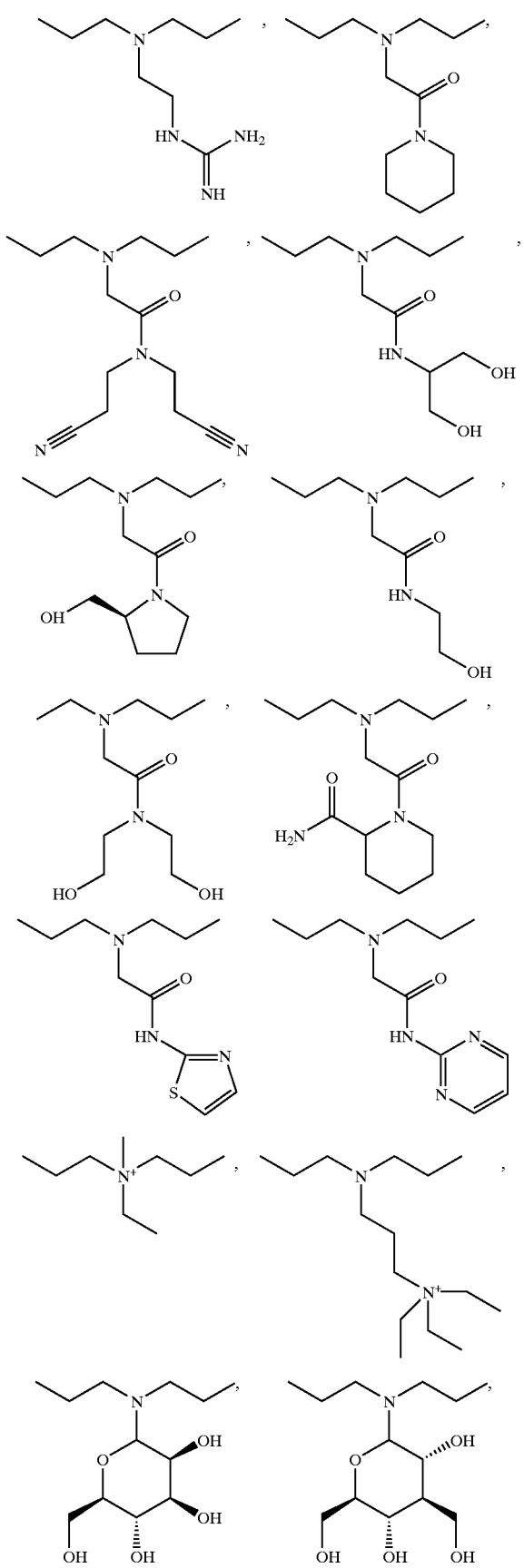

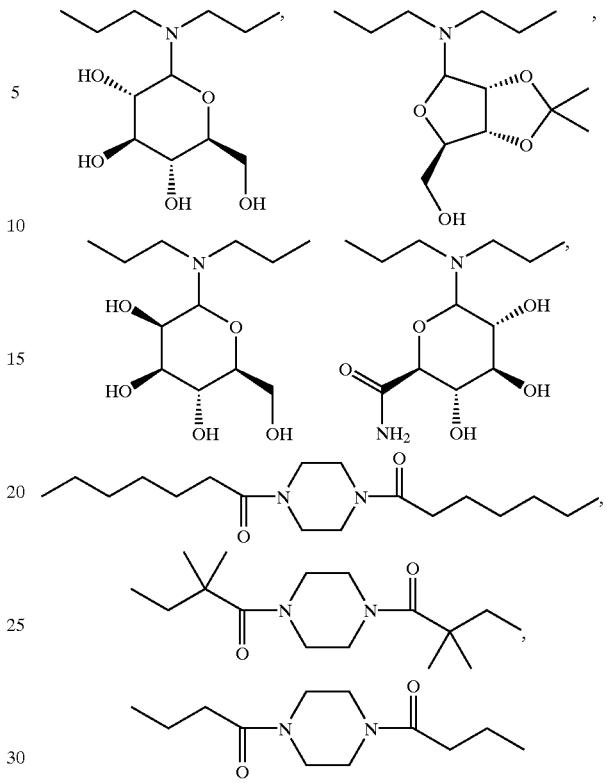

and $Ar^1$ and $Ar^2$ each represents a nonsubstituted 4-hydroxyphenyl group.

2. The method according to claim 1 wherein the compound of formula (I) is the active ingredient in a pharmaceutical composition comprising said compound and a pharmaceutically acceptable carrier or diluent.

3. A method for selectively inhibiting cancer cell proliferation by inhibiting ribonucleotide reductase comprising administering to a subject in need thereof an effective amount of a compound represented by formula (I), or a physiologically acceptable salt thereof:

$$Ar^1—S—R^1—S—Ar^2 \qquad (I)$$

wherein $R^1$ represents a nonmetal bridging group selected from —$C_2H_4$—S—$C_2H_4$—, —$C_2H_4$—S—$C_3H_6$—, —$C_2H_4$—S—$C_4H_4$—, —$C_2H_4$—S—$C_4H_6$—, —$C_2H_4S$—$C_4H_8$—, —$C_3H_6$—S—$C_3H_6$—, —$C_3H_6$—S—$C_4H_6$—, —$C_3H_6$—S—$C_4H_8$—, —$C_4H_8$—S—$C_4H_8$—, —$CH_2CO$—S—$C_2H_4$—, —$CH_2CO$—S—$C_3H_6$—, —$CH_2CO$—S—$C_4H_8$—, —$CH_2CO$—S—$C_4H_6$—, —$CH_2CO$—S—$C_4H_4$—, —$CH(CH_3)CO$—S—$C_2H4$—, —$C_2H_4CO$—S—$CH_2CH(OH)CH_2$—, —$CH_2CO$—S—$C_2H_4NHCOCH_2$—, —$C_2H_4CO$—S—$C_2H_4NHCOC_2H_4$—, —$C_2H_4O$—$C_2H_4$—, —$C_2H_4$—O—$C_3H_6$—, —$C_2H_4$—O—$C_4H_4$—, —$C_2H_4$—O—$C_4H_6$—, —$C_2H_4$—O—$C_4H_8$—, —$C_3H_6$—O—$C_3H_6$—, —$C_3H_6$—O—$C_4H_6$—, —$C_3H_6$—O—$C_4H_8$—, —$C_4H_8$—O—$C_4H_8$—, —$CH_2CO$—O—$C_2H_4$—, —$CH_2CO$—O—$C_3H_6$—, —$CH_2CO$—O—$C_4H_8$—, —$CH_2CO$—O—$C_4H_6$—, —$CH_2CO$—O—$C_4H_4$—, —$CH(CH_3)CO$—O—$C_2H_4$—, —$C_2H_4CO$—O—$CH_2CH(OH)CH_2$—, —$CH_2CO$—O—$C_2H_4NHCOCH_2$, —$C_2H_4CO$—O—$C_2H_4NHCOC_2H_4$—; —$R^2$—N($R^4$)—$R^3$—, wherein $R^2$, $R^3$ and $R^4$ are defined as follows:

| $R^2$ | $R^3$ | $R^4$ |
|---|---|---|
| —$C_2H_4$— | —$C_2H_4$— | —H— |
| —$C_3H_6$— | —$C_3H_6$— | —H— |
| —$C_4H_8$— | —$C_4H_8$— | —H— |
| —$C_2H_4$— | —$C_2H_4$— | —OH— |
| —$C_2H_4$— | —$C_2H_4$— | —C(=NH)$NH_2$ |
| —$C_2H_4$— | —$C_2H_4$— | —COC$_3H_7$ |
| —$C_2H_4$— | —$C_2H_4$— | —COCH$_2$CH$_2$CO$_2$H |
| —$C_2H_4$— | —$C_2H_4$— | —COCH$_2$CH$_2$S—Ph—OH-p |
| —$C_2H_4$— | —$C_2H_4$— | —CHO |
| —$C_2H_4$— | —$C_2H_4$— | —COCH$_3$ |
| —$C_2H_4$— | —$C_2H_4$— | —SO$_2$CH$_3$ |
| —$C_3H_6$— | —$C_3H_6$— | —CHO |
| —$C_2H_4$— | —$C_2H_4$— | —CH$_2$CH$_2$NH$_2$ |
| —CH$_2$CO— | —$C_2H_4$— | —H |
| —CH$_2$CO— | —$C_3H_6$— | —H |
| —CH$_2$CO— | —$C_4H_8$— | —H |
| —CH$_2$CO— | —$C_4H_6$— | —H |
| —CH$_2$CO— | —$C_4H_4$— | —H |
| —CH$_2$CO— | —$C_2H_4$— | —CHO |
| —CH(CH$_3$)CO— | —$C_2H_4$— | —H |
| —CH(CH$_3$)CO— | —$C_2H_4$— | —C$_2H_4$OH |
| —$C_2H_4$CO— | —CH$_2$CH(OH)CH$_2$— | —C$_2H_4$OH |
| —CH$_2$CO— | —C$_2H_4$NHCOCH$_2$— | —H |
| —$C_2H_4$CO— | —C$_2H_4$NHCOC$_2H_4$— | —H |
| —$C_2H_4$— | —$C_2H_4$— | —$C_2H_5$ |
| —$C_2H_4$— | —$C_2H_4$— | —$C_3H_7$ |
| —$C_2H_4$— | —$C_2H_4$— | —CH$_2$—C≡CH |
| —$C_2H_4$— | —$C_2H_4$— | —CH$_2$—CH=CH$_2$ |
| —$C_2H_4$— | —$C_2H_4$— | —CH$_2$-cyclopropyl |
| —$C_2H_4$— | —$C_2H_4$— | —CH$_2$—SO$_2$NH$_2$ |
| —$C_2H_4$— | —$C_2H_4$— | —CH$_2$—CN |
| —$C_2H_4$— | —$C_2H_4$— | —C$_2H_4$—CO—NH$_2$ |
| —$C_2H_4$— | —$C_2H_4$— | —C$_2H_4$CO—N(CH$_3$)$_2$ |
| —$C_2H_4$— | —$C_2H_4$— | —C$_2H_4$CO—N(C$_2H_5$)$_2$ |
| —$C_2H_4$— | —$C_2H_4$— | —CH$_2$—CO—CH$_3$ |
| —$C_2H_4$— | —$C_2H_4$— | —C$_2H_4$—NH—CO—NH$_2$ |
| —$C_2H_4$— | —$C_2H_4$— | —C$_2H_4$—NH—CO—CH$_3$ |
| —$C_2H_4$— | —$C_2H_4$— | —CH$_2$F |
| —$C_2H_4$— | —$C_2H_4$— | —CF$_3$ |
| —$C_2H_4$— | —$C_2H_4$— | —C$_2H_4$-(N-succinimido) |
| —$C_2H_4$— | —$C_2H_4$— | —C$_2H_4$—S—CH$_3$ |
| —$C_2H_4$— | —$C_2H_4$— | —CH$_2$-ethyleneacetal |
| —$C_2H_4$— | —$C_2H_4$— | —CH$_2$-(2-thienyl) |
| —$C_2H_4$— | —$C_2H_4$— | -furfuryl |
| —$C_2H_4$— | —$C_2H_4$— | —CH$_2$-(4-pyridyl) |
| —$C_2H_4$— | —$C_2H_4$— | -o-hydroxybenzyl |
| —$C_2H_4$— | —$C_2H_4$— | -m-hydroxybenzyl |
| —$C_2H_4$— | —$C_2H_4$— | -p-hydroxybenzyl |
| —$C_2H_4$— | —$C_2H_4$— | —(CH$_2$)$_3$—OH |
| —$C_2H_4$— | —$C_2H_4$— | —CH$_2$—NH—CO—CH$_3$ |
| —$C_2H_4$— | —$C_2H_4$— | —CH$_2$—CO—NH$_2$ |
| —$C_2H_4$— | —$C_2H_4$— | -benzyl |
| —$C_2H_4$— | —$C_2H_4$— | —CH$_2$-(3-pyridyl) |
| —$C_2H_4$— | —$C_2H_4$— | —CH$_2$-(2-pyridyl) |
| —$C_2H_4$— | —$C_2H_4$— | —CH$_2$-(2-quinolinyl) |
| —$C_2H_4$— | —$C_2H_4$— | —$C_2H_4$—OH |
| —$C_2H_4$— | —$C_2H_4$— | —(CH$_2$)$_3$—OCH$_3$ |
| —$C_2H_4$— | —$C_2H_4$— | —$C_2H_4$—OCH$_3$ |
| —$C_2H_4$— | —$C_2H_4$— | -o-fluorobenzyl |
| —$C_2H_4$— | —$C_2H_4$— | -p-fluorobenzyl |
| —$C_2H_4$— | —$C_2H_4$— | —$C_2H_4$—CO-(N-morpholino) |
| —$C_2H_4$— | —$C_2H_4$— | —$C_2H_4$—CO-(1-piperidyl) |
| —$C_2H_4$— | —$C_2H_4$— | —$C_2H_4$—N(C$_2H_5$)$_2$ |
| —$C_2H_4$— | —$C_2H_4$— | —$C_2H_4$-(N-morpholino) |
| —$C_2H_4$— | —$C_2H_4$— | —$C_2H_4$-(1-piperidyl) |
| —$C_2H_4$— | —$C_2H_4$— | —CO—CH$_3$ |
| —$C_2H_4$— | —$C_2H_4$— | —CO—C$_2H_5$ |
| —$C_2H_4$— | —$C_2H_4$— | —CO—C$_6H_5$ |
| —$C_2H_4$— | —$C_2H_4$— | —CO-(2-pyridyl) |
| —$C_2H_4$— | —$C_2H_4$— | —CO-(3-pyridyl) |
| —$C_2H_4$— | —$C_2H_4$— | —CO-(4-pyridyl) |
| —$C_2H_4$— | —$C_2H_4$— | —SO$_2$—CH$_3$ |
| —$C_2H_4$— | —$C_2H_4$— | —SO$_2$—C$_6H_5$ |
| —$C_2H_4$— | —$C_2H_4$— | —CO—NH$_2$ |
| —$C_2H_4$— | —$C_2H_4$— | —CO—NH(CH$_3$) |
| —$C_2H_4$— | —$C_2H_4$— | —CO—N(CH$_3$)$_2$ |
| —$C_2H_4$— | —$C_2H_4$— | —CO—N(C$_2H_5$)$_2$ |

-continued

| $R^2$ | $R^3$ | $R^4$ |
|---|---|---|
| —$C_2H_4$— | —$C_2H_4$— | —CO-(N-morpholino) |
| —$C_2H_4$— | —$C_2H_4$— | —CO-(1-piperidyl) |
| —$C_2H_4$— | —$C_2H_4$— | —CO—NH—C$_6H_5$ |
| —$C_2H_4$— | —$C_2H_4$— | —CO—NH-(2-pyridyl) |
| —$C_2H_4$— | —$C_2H_4$— | —SO$_2$—NH$_2$ |
| —$C_2H_4$— | —$C_2H_4$— | —SO$_2$—N(C$_2H_5$)$_2$ |
| —$C_2H_4$— | —$C_2H_4$— | —SO$_2$-(N-morpholino); |

—CH$_2$—, —C$_2H_4$—, —C$_3H_6$—, —C$_4H_8$—, —C$_5H_{10}$—, —C$_6H_{12}$—, —C$_7H_{14}$—, —C$_8H_{16}$—, —C$_9H_{18}$—, —C$_{10}H_{20}$—, —C$_{11}H_{22}$—, —C$_2H_4$—SO$_2$—C$_2H_4$—SO$_2$—C$_2H_4$—, —CH(CH$_3$), —CH(C$_2H_5$)—, CH(n—C$_3H_7$)—, —CH(C$_6H_5$)—, —C(CH$_3$)$_2$—, —CH(COOH)—, CH(C$_2H_4$OH)—, —CH(CH$_3$)—CH$_2$—, —CH(C$_2H_4$OH)—CH$_2$—, —CH(COOH)—CH$_2$—, —CH(C$_2H_5$)—CH$_2$—, —CH$_2$—CH(OH)—CH$_2$—, —CH$_2$—C(CH$_2$B)$_2$—CH$_2$, wherein B is p-hydroxyphenylthio, CH$_2$—S—CH$_2$—, —CH$_2$—CH=CH—CH$_2$—, —CH$_2$—C≡C—CH$_2$—, —CH$_2$—C$_6H_4$—CH$_2$— wherein —C$_6H_4$—, is an o-phenylene group, —C$_2H_4$—O—CH$_2$—O—C$_2H_4$—, —C$_2H_4$—O—C$_2H_4$—O—C$_2H_4$—, —CH$_2$—COO—C$_2H_4$—OCOCH$_2$—, —CH$_2$—COO—C$_3H_6$—OCOCH$_2$—, —CH$_2$CH(OH)CH$_2$—O—C$_2H_4$—O—CH$_2$CH(OH)CH$_2$—, —(C$_2H_4$O)$_2$—CO—CH$_2$—CO—(C$_2H_4$O)$_2$, —(C$_2H_4$O)$_2$—CO—(trans)CH=CH—CO—(C$_2H_4$O)$_2$—, —CH$_2$—COO—(C$_2H_4$O)$_3$—CO—CH$_2$—, —CH$_2$—COO—(C$_2H_4$O)$_4$—CO—CH$_2$—, —(C$_2H_4$O)$_3$—C$_2H_4$—, —(C$_2H_4$O)$_4$—C$_2H_4$—, —(C$_2H_4$O)$_5$—C$_2H_4$—, —(C$_2H_4$O)$_3$—CO—(C$_2H_4$O)$_3$—, —(C$_2H_4$O)$_2$—CO—C$_2H_4$—CO—(C$_2H_4$O)$_2$, —CH$_2$—CO—CO—CH$_2$—, —CO—CH$_2$—CO—,

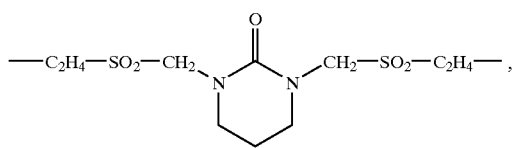
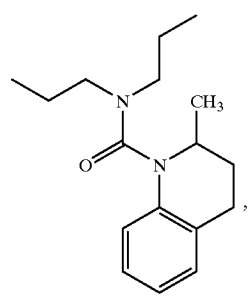
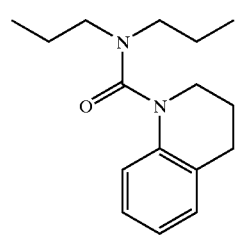
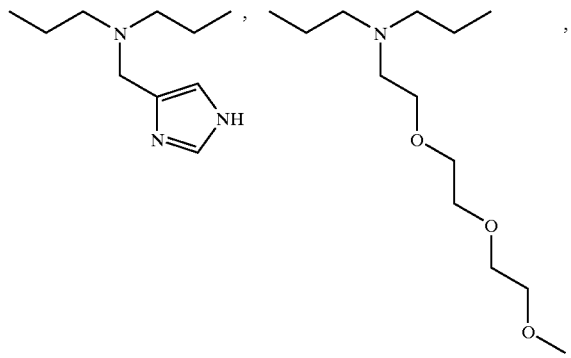
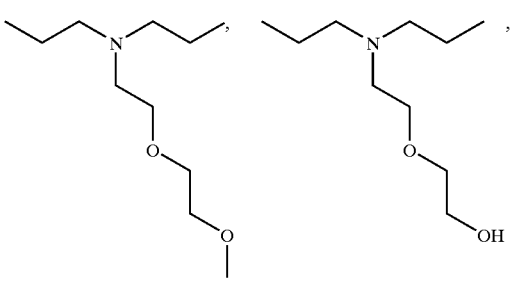
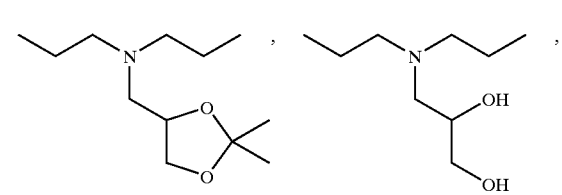
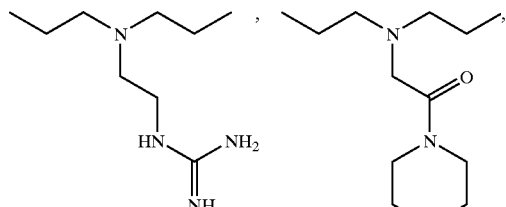
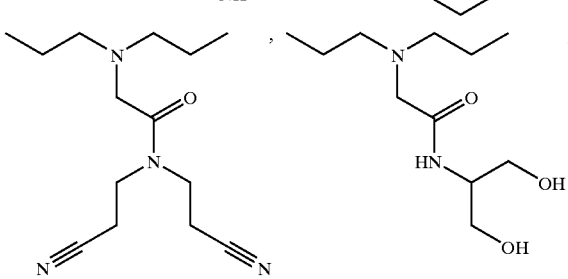
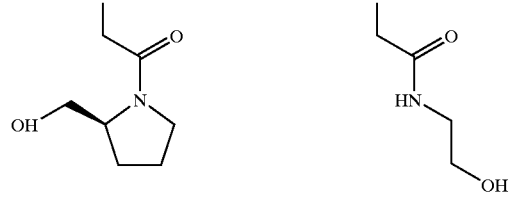

101
-continued

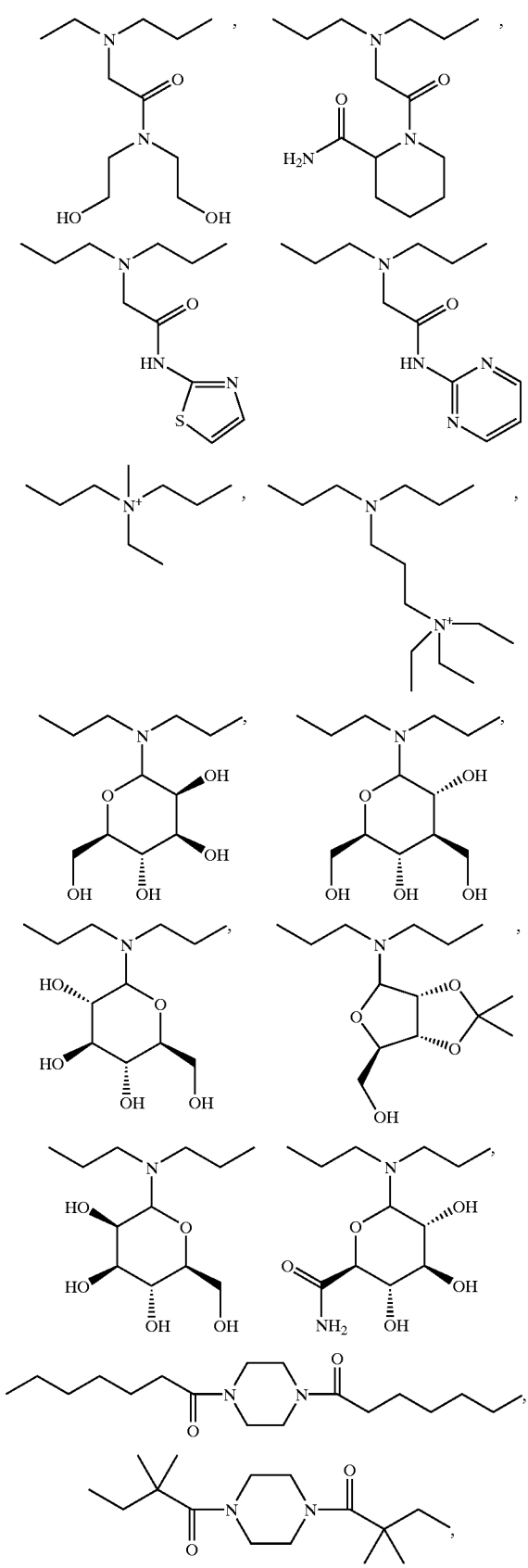

102
-continued

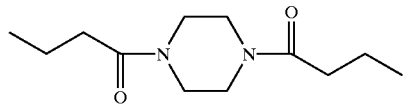

and $Ar^1$ and $Ar^2$ each represents a nonsubstituted 4-hydroxyphenyl group.

4. A method for treatment of ovarian or lung cancer comprising administering to a subject in need of treatment an effective amount of a compound represented by formula (I), or a physiologically acceptable salt thereof:

$$Ar^1\text{—S—}R^1\text{—S—}Ar^2 \qquad (I)$$

wherein $R^1$ represents a nonmetal bridging group selected from —$C_2H_4$—S—$C_2H_4$—, —$C_2H_4$—S—$C_3H_6$—, —$C_2H_4$—S—$C_4H_4$—, —$C_2H_4$—S—$C_4H_6$—, —$C_2H_4$S—$C_4H_8$—, —$C_3H_6$—S—$C_3H_6$—, —$C_3H_6$—S—$C_4H_6$—, —$C_3H_6$—S—$C_4H_8$—, —$C_4H_8$—S—$C_4H_8$—, —$CH_2CO$—S—$C_2H_4$—, —$CH_2CO$—S—$C_3H_6$—, —$CH_2CO$—S—$C_4H_8$—, —$CH_2CO$—S—$C_4H_6$—, —$CH_2CO$—S—$C_4H_4$—, —$CH(CH_3)CO$—S—$C_2H_4$—, —$C_2H_4CO$—S—$CH_2CH(OH)CH_2$—, —$CH_2CO$—S—$C_2H_4NHCOCH_2$—, —$C_2H_4CO$—S—$C_2H_4NHCOC_2H_4$—, —$C_2H_4O$—$C_2H_4$—, —$C_2H_4$—O—$C_3H_6$—, —$C_2H_4$—O—$C_4H_4$—, —$C_2H_4$—O—$C_4H_6$—, —$C_2H_4$—O—$C_4H_8$—, —$C_3H_6$—O—$C_3H_6$—, —$C_3H_6$—O—$C_4H_6$—, —$C_3H_6$—O—$C_4H_8$—, —$C_4H_8$—O—$C_4H_8$—, —$CH_2CO$—O—$C_2H_4$—, —$CH_2CO$—O—$C_3H_6$—, —$CH_2CO$—O—$C_4H_8$—, —$CH_2CO$—O—$C_4H_6$—, —$CH_2CO$—O—$C_4H_4$—, —$CH(CH_3)CO$—O—$C_2H_4$—, —$C_2H_4CO$—O—$CH_2CH(OH)CH_2$—, —$CH_2CO$—O—$C_2H_4NHCOCH_2$, —$C_2H_4CO$—O—$C_2H_4NHCOC_2H_4$—; —$R^2$—$N(R^4)$—$R^3$—, wherein $R^2$, $R^3$ and $R^4$ are defined as follows:

| $R^2$ | $R^3$ | $R^4$ |
|---|---|---|
| —$C_2H_4$— | —$C_2H_4$— | —H— |
| —$C_3H_6$— | —$C_3H_6$— | —H— |
| —$C_4H_8$— | —$C_4H_8$— | —H— |
| —$C_2H_4$— | —$C_2H_4$— | —OH— |
| —$C_2H_4$— | —$C_2H_4$— | —C(=NH)$NH_2$ |
| —$C_2H_4$— | —$C_2H_4$— | —$COC_3H_7$ |
| —$C_2H_4$— | —$C_2H_4$— | —$COCH_2CH_2CO_2H$ |
| —$C_2H_4$— | —$C_2H_4$— | —$COCH_2CH_2$S—Ph—OH-p |
| —$C_2H_4$— | —$C_2H_4$— | —CHO |
| —$C_2H_4$— | —$C_2H_4$— | —$COCH_3$ |
| —$C_2H_4$— | —$C_2H_4$— | —$SO_2CH_3$ |
| —$C_3H_6$— | —$C_3H_6$— | —CHO |
| —$C_2H_4$— | —$C_2H_4$— | —$CH_2CH_2NH_2$ |
| —$CH_2CO$— | —$C_2H_4$— | —H |
| —$CH_2CO$— | —$C_3H_6$— | —H |
| —$CH_2CO$— | —$C_4H_8$— | —H |
| —$CH_2CO$— | —$C_4H_6$— | —H |
| —$CH_2CO$— | —$C_4H_4$— | —H |
| —$CH_2CO$— | —$C_4H_4$— | —CHO |
| —$CH(CH_3)CO$— | —$C_2H_4$— | —H |
| —$CH(CH_3)CO$— | —$C_2H_4$— | —$C_2H_4OH$ |
| —$C_2H_4CO$— | —$CH_2CH(OH)CH_2$— | —$C_2H_4OH$ |
| —$CH_2CO$— | —$C_2H_4NHCOCH_2$— | —H |
| —$C_2H_4CO$— | —$C_2H_4NHCOC_2H_4$— | —H |
| —$C_2H_4$— | —$C_2H_4$— | —$C_2H_5$ |
| —$C_2H_4$— | —$C_2H_4$— | —$C_3H_7$ |
| —$C_2H_4$— | —$C_2H_4$— | —$CH_2$—C≡CH |
| —$C_2H_4$— | —$C_2H_4$— | —$CH_2$—CH=$CH_2$ |
| —$C_2H_4$— | —$C_2H_4$— | —$CH_2$-cyclopropyl |

-continued

| R² | R³ | R⁴ |
|---|---|---|
| —C₂H₄— | —C₂H₄— | —CH₂—SO₂NH₂ |
| —C₂H₄— | —C₂H₄— | —CH₂—CN |
| —C₂H₄— | —C₂H₄— | —C₂H₄—CO—NH₂ |
| —C₂H₄— | —C₂H₄— | —C₂H₄CO—N(CH₃)₂ |
| —C₂H₄— | —C₂H₄— | —C₂H₄CO—N(C₂H₅)₂ |
| —C₂H₄— | —C₂H₄— | —CH₂—CO—CH₃ |
| —C₂H₄— | —C₂H₄— | —C₂H₄—NH—CO—NH₂ |
| —C₂H₄— | —C₂H₄— | —C₂H₄—NH—CO—CH₃ |
| —C₂H₄— | —C₂H₄— | —CH₂F |
| —C₂H₄— | —C₂H₄— | —CF₃ |
| —C₂H₄— | —C₂H₄— | —C₂H₄-(N-succinimido) |
| —C₂H₄— | —C₂H₄— | —C₂H₄—S—CH₃ |
| —C₂H₄— | —C₂H₄— | —CH₂-ethyleneacetal |
| —C₂H₄— | —C₂H₄— | —CH₂-(2-thienyl) |
| —C₂H₄— | —C₂H₄— | -furfuryl |
| —C₂H₄— | —C₂H₄— | —CH₂-(4-pyridyl) |
| —C₂H₄— | —C₂H₄— | -o-hydroxybenzyl |
| —C₂H₄— | —C₂H₄— | -m-hydroxybenzyl |
| —C₂H₄— | —C₂H₄— | -p-hydroxybenzyl |
| —C₂H₄— | —C₂H₄— | —(CH₂)₃—OH |
| —C₂H₄— | —C₂H₄— | —CH₂—NH—CO—CH₃ |
| —C₂H₄— | —C₂H₄— | —CH₂—CO—NH₂ |
| —C₂H₄— | —C₂H₄— | -benzyl |
| —C₂H₄— | —C₂H₄— | —CH₂-(3-pyridyl) |
| —C₂H₄— | —C₂H₄— | —CH₂-(2-pyridyl) |
| —C₂H₄— | —C₂H₄— | —CH₂-(2-quinolinyl) |
| —C₂H₄— | —C₂H₄— | —C₂H₄—OH |
| —C₂H₄— | —C₂H₄— | —(CH₂)₃—OCH₃ |
| —C₂H₄— | —C₂H₄— | —C₂H₄—OCH₃ |
| —C₂H₄— | —C₂H₄— | -o-fluorobenzyl |
| —C₂H₄— | —C₂H₄— | -p-fluorobenzyl |
| —C₂H₄— | —C₂H₄— | —C₂H₄—CO-(N-morpholino) |
| —C₂H₄— | —C₂H₄— | —C₂H₄—CO-(1-piperidyl) |
| —C₂H₄— | —C₂H₄— | —C₂H₄—N(C₂H₅)₂ |
| —C₂H₄— | —C₂H₄— | —C₂H₄-(N-morpholino) |
| —C₂H₄— | —C₂H₄— | —C₂H₄-(1-piperidyl) |
| —C₂H₄— | —C₂H₄— | —CO—CH₃ |
| —C₂H₄— | —C₂H₄— | —CO—C₂H₅ |
| —C₂H₄— | —C₂H₄— | —CO—C₆H₅ |
| —C₂H₄— | —C₂H₄— | —CO-(2-pyridyl) |
| —C₂H₄— | —C₂H₄— | —CO-(3-pyridyl) |
| —C₂H₄— | —C₂H₄— | —CO-(4-pyridyl) |
| —C₂H₄— | —C₂H₄— | —SO₂—CH₃ |
| —C₂H₄— | —C₂H₄— | —SO₂—C₆H₅ |
| —C₂H₄— | —C₂H₄— | —CO—NH₂ |
| —C₂H₄— | —C₂H₄— | —CO—NH(CH₃) |
| —C₂H₄— | —C₂H₄— | —CO—N(CH₃)₂ |
| —C₂H₄— | —C₂H₄— | —CO—N(C₂H₅)₂ |
| —C₂H₄— | —C₂H₄— | —CO-(N-morpholino) |
| —C₂H₄— | —C₂H₄— | —CO-(1-piperidyl) |
| —C₂H₄— | —C₂H₄— | —CO—NH—C₆H₅ |
| —C₂H₄— | —C₂H₄— | —CO—NH-(2-pyridyl) |
| —C₂H₄— | —C₂H₄— | —SO₂—NH₂ |
| —C₂H₄— | —C₂H₄— | —SO₂—N(C₂H₅)₂ |
| —C₂H₄— | —C₂H₄— | —SO₂-(N-morpholino); |

—CH₂—, —C₂H₄—, —C₃H₆—, —C₄H₈—, —C₅H₁₀—, —C₆H₁₂—, —C₇H₁₄—, —C₈H₁₆—, —C₉H₁₈—, —C₁₀H₂₀—, —C₁₁H₂₂, —C₂H₄—SO₂—C₂H₄—SO₂—C₂H₄—, —CH(CH₃), —CH(C₂H₅)—, CH(n—C₃H₇)—, —CH(C₆H₅)—, —C(CH₃)₂—, —CH(COOH)—, CH(C₂H₄OH)—, —CH(CH₃)—CH₂—, —CH(C₂H₄OH)—CH₂—, —CH(COOH)—CH₂—, —CH(C₂H₅)—CH₂—, —CH₂—CH(OH)—CH₂—, —CH₂—C(CH₂B)₂—CH₂, wherein B is p-hydroxyphenylthio, CH₂—S—CH₂—, —CH₂—CH=CH—CH₂—, —CH₂—C≡C—CH₂—, —CH₂—C₆H₄—CH₂— wherein —C₆H₄—, is an o-phenylene group, —C₂H₄—O—CH₂—O—C₂H₄—, —C₂H₄—O—C₂H₄—O—C₂H₄—, —CH₂—COO—C₂H₄—OCOCH₂—, —CH₂—COO—C₃H₆—OCOCH₂—, —CH₂CH(OH)CH₂—O—C₂H₄—O—CH₂CH(OH)CH₂—, —(C₂H₄O)₂—CO—CH₂—CO—(C₂H₄O)₂, —(C₂H₄O)₂—CO—(trans)CH=CH—CO—(C₂H₄O)₂—, —CH₂—COO—(C₂H₄O)₃—CO—CH₂—, —CH₂—COO—(C₂H₄O)₄—CO—CH₂—, —(C₂H₄O)₃—C₂H₄—, —(C₂H₄O)₄—C₂H₄—, —(C₂H₄O)₅—C₂H₄—, —(C₂H₄O)₃—CO—(C₂H₄O)₃—, —(C₂H₄O)₂—CO—C₂H₄—CO—(C₂H₄O)₂, —CH₂—CO—CO—CH₂—, —CO—CH₂—CO—,

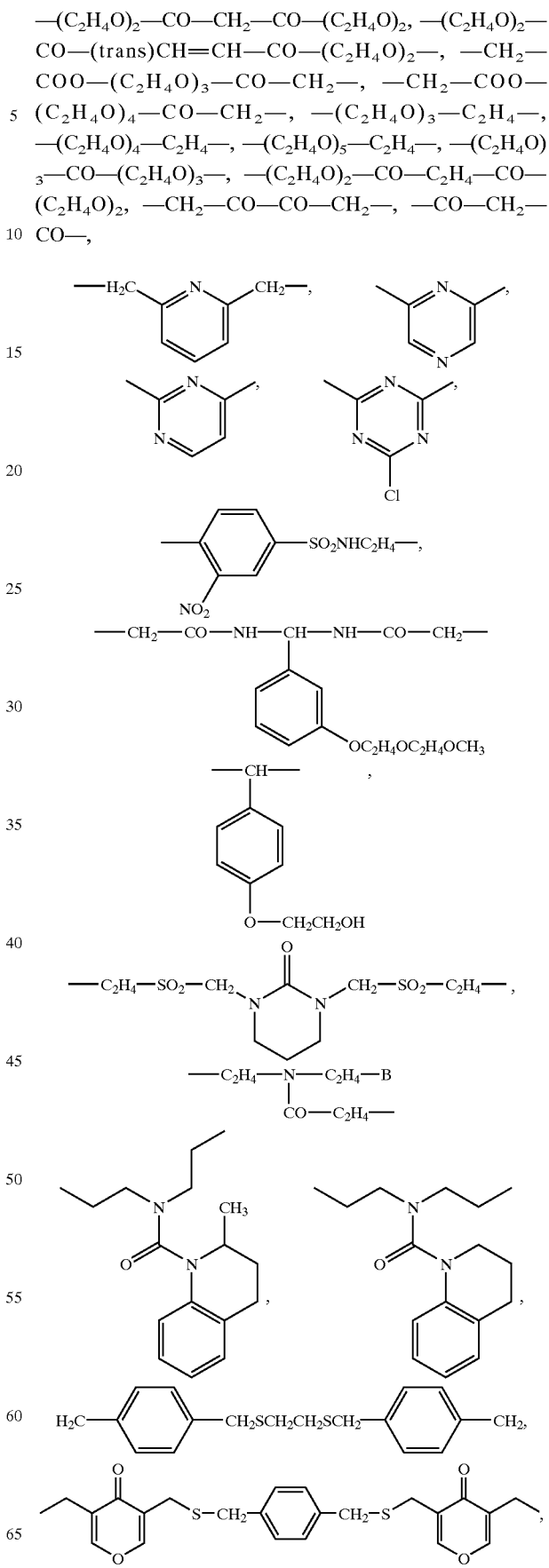

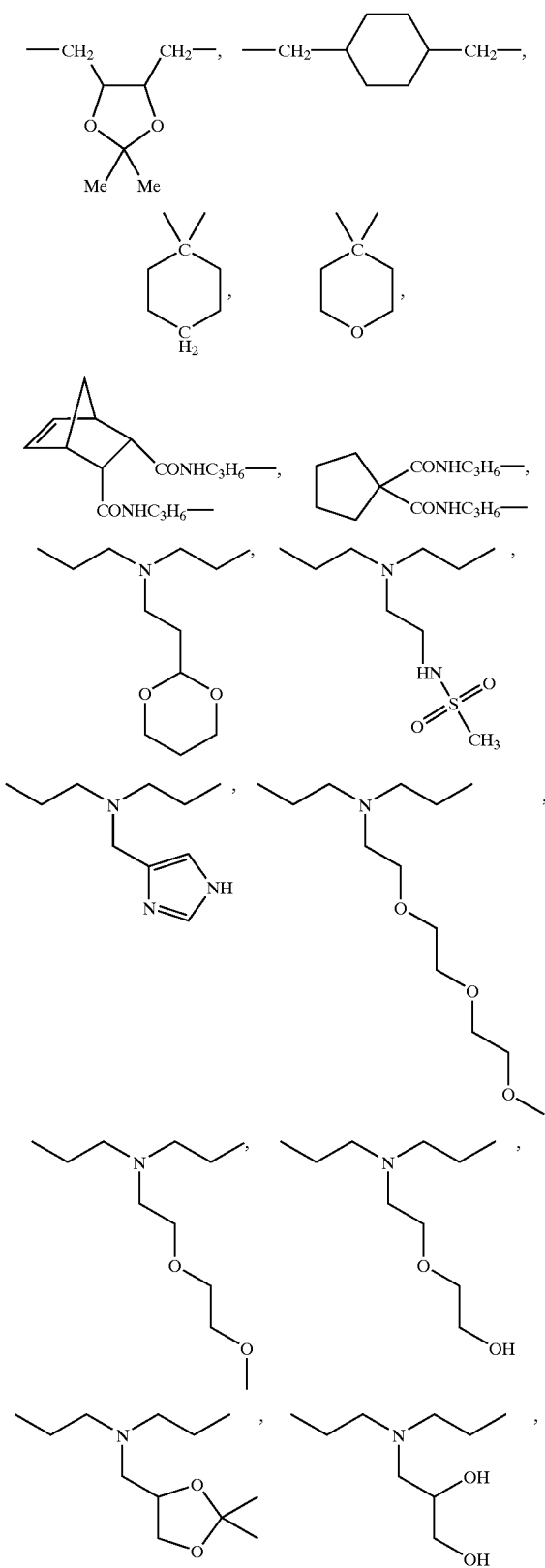
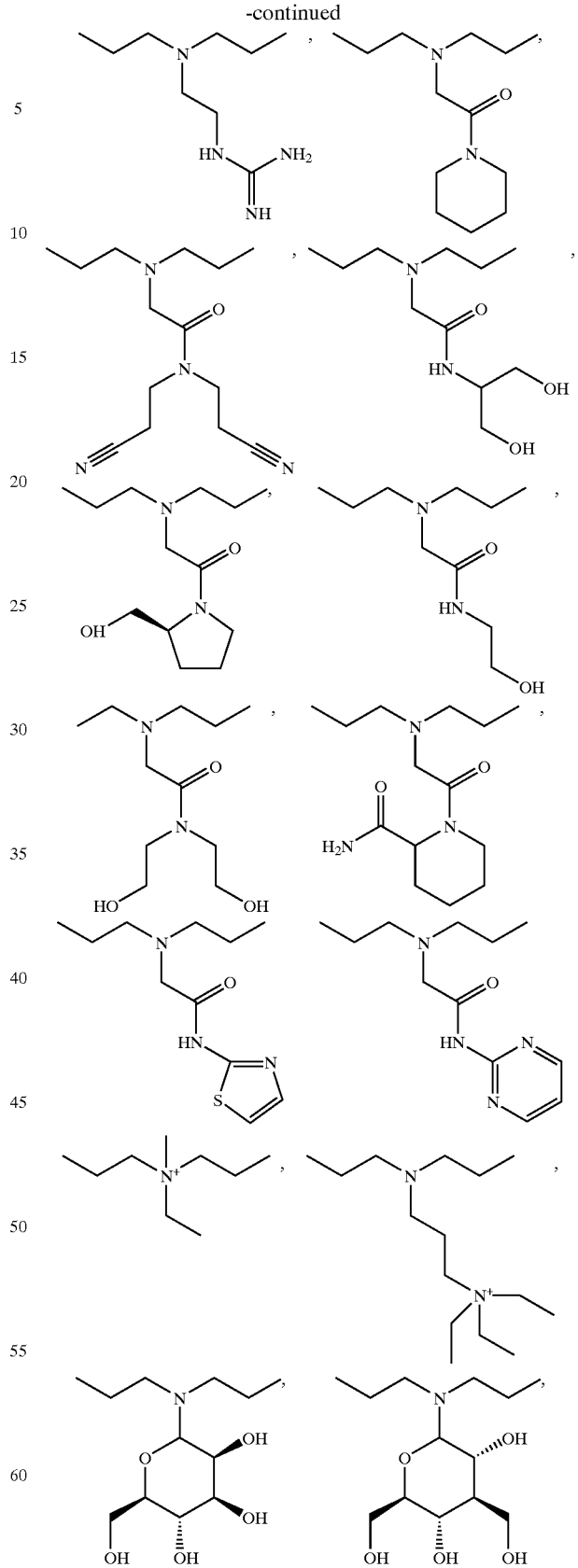

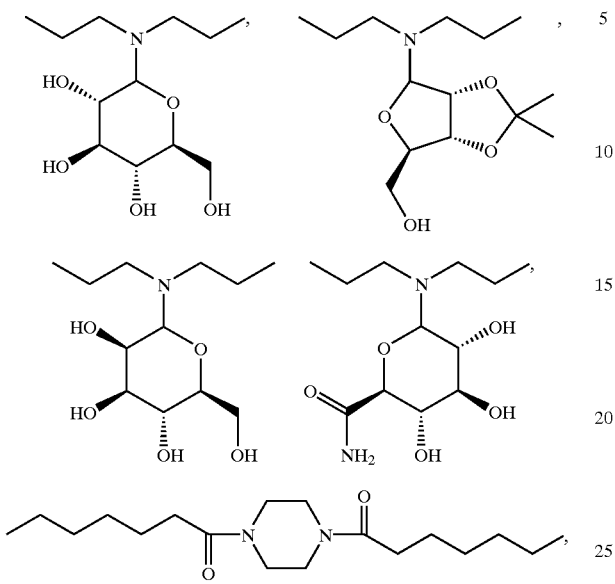
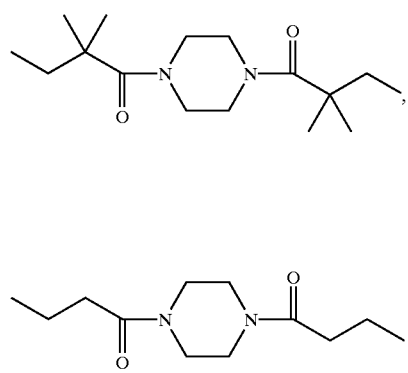
and Ar[1] and Ar[2] each represents a nonsubstituted 4-hydroxyphenyl group.
* * * * *